(12) United States Patent
Gershoni et al.

(10) Patent No.: US 11,862,303 B1
(45) Date of Patent: Jan. 2, 2024

(54) COLLECTION OF DIGITAL HEALTH HUBS WITH ARTIFICIAL INTELLIGENCE

(71) Applicant: Telemedicine Health, Inc., Weston, FL (US)

(72) Inventors: Daniel Gershoni, Weston, FL (US); Farhad David Nosrati, Encino, CA (US)

( * ) Notice: Subject to any disclaimer, the term of this patent is extended or adjusted under 35 U.S.C. 154(b) by 107 days.

(21) Appl. No.: 16/385,175

(22) Filed: Apr. 16, 2019

Related U.S. Application Data

(60) Provisional application No. 62/659,767, filed on Apr. 19, 2018.

(51) Int. Cl.
| | |
|---|---|
| *G16H 10/60* | (2018.01) |
| *G16H 50/30* | (2018.01) |
| *G16H 80/00* | (2018.01) |
| *H04L 67/12* | (2022.01) |
| *G06N 3/006* | (2023.01) |
| *H04L 12/18* | (2006.01) |

(52) U.S. Cl.
CPC ............ *G16H 10/60* (2018.01); *G06N 3/006* (2013.01); *G16H 50/30* (2018.01); *G16H 80/00* (2018.01); *H04L 12/185* (2013.01); *H04L 67/12* (2013.01)

(58) Field of Classification Search
CPC ........ G16H 10/60; G16H 50/30; G16H 80/00; G06N 3/006; H04L 12/185; H04L 67/12
See application file for complete search history.

(56) References Cited

U.S. PATENT DOCUMENTS

| | | |
|---|---|---|
| 5,507,277 A | 4/1996 | Rubsamen et al. |
| 6,336,900 B1 | 1/2002 | Alleckson et al. |
| 6,439,422 B1 | 8/2002 | Papp et al. |
| 6,749,566 B2 | 6/2004 | Russ |
| 6,848,593 B2 | 2/2005 | Papp |

(Continued)

FOREIGN PATENT DOCUMENTS

| | | |
|---|---|---|
| JP | 2014533997 A | 3/2017 |
| WO | WO2002011778 A1 | 2/2002 |
| WO | WO2002094234 A1 | 11/2002 |

OTHER PUBLICATIONS

Health Tap unveils dr. A.I. (2017). Professional Services Close-Up (Year: 2017).*

*Primary Examiner* — Sheetal R Paulson
(74) *Attorney, Agent, or Firm* — Allen D. Hertz, P.A.; Allen D. Hertz

(57) ABSTRACT

The present invention HUB relates generally to a collection of digital health hubs (HH) with artificial intelligence and wireless connectivity to autonomously communicate with each other to create a fully automated digital health social network, that can operate both autonomously with no interaction from human element, as well as through multiple layers of outside individuals and care facilities, including but not limited to family members, caregivers and medical care providers. The present invention HUB performs various tasks to monitor, record, diagnose and communicate health and safety of individuals. The HUB additionally triages users and analyzes their recorded health data to autonomously create public and private social groups, communicate packets of general and detailed information on their users' database within HH groups. HHs can join (dock into) or exit (un-dock) from one or more public or private social HH groups.

21 Claims, 32 Drawing Sheets

(56) References Cited

U.S. PATENT DOCUMENTS

| | | | |
|---|---|---|---|
| 7,978,062 | B2 | 7/2011 | LaLonde et al. |
| 8,918,085 | B2 | 12/2014 | Lew et al. |
| 9,436,645 | B2 | 9/2016 | Al-Ali et al. |
| 9,582,055 | B2 * | 2/2017 | De Jong .............. G06F 13/4081 |
| 9,712,468 | B2 | 7/2017 | Patel |
| 10,181,013 | B2 | 1/2019 | Portney et al. |
| 2002/0184415 | A1 | 12/2002 | Naghavi |
| 2005/0055242 | A1 | 3/2005 | Bello |
| 2006/0157491 | A1 | 7/2006 | Whittle et al. |
| 2007/0260491 | A1 | 11/2007 | Palmer et al. |
| 2010/0251117 | A1 * | 9/2010 | Baughman ............. G06N 3/006 |
| | | | 703/11 |
| 2014/0195263 | A1 | 7/2014 | Santos |
| 2016/0180044 | A1 | 6/2016 | Delisle |
| 2017/0098051 | A1 * | 4/2017 | Balram ................. G16H 50/20 |
| 2017/0231870 | A1 | 8/2017 | Stachler et al. |
| 2018/0028408 | A1 | 2/2018 | Li et al. |
| 2018/0110939 | A1 | 4/2018 | Lanzkowsky |
| 2018/0218126 | A1 * | 8/2018 | Salazar ................. G16H 50/30 |
| 2019/0279767 | A1 * | 9/2019 | Bates .................... G16H 15/00 |

* cited by examiner

COLLECTION OF DIGITAL HEALTH HUBS WITH ARTIFICIAL INTELLIGENCE

CROSS-REFERENCE TO RELATED APPLICATIONS

The present Application claims the benefit of U.S. Provisional Patent Application Ser. No. 62/659,767 entitled "Smart Personal Emergency Response System", filed on Apr. 19, 2018, the contents of which are incorporated in this disclosure by reference in their entirety.

FIELD OF THE INVENTION

The present invention generally relates to a collection of digital Health Hubs (HH) with artificial intelligence and wireless connectivity to autonomously communicate with each other in order to create a fully automated digital health social network, that can operate both autonomously with no interaction from Human element, as well as through multiple layers of outside individuals and care facilities, including but not limited to family members, caregivers and medical care providers.

BACKGROUND OF THE INVENTION

The system disclosed herein, in general refers to a collection of digital Health Hubs (HH) with Artificial Intelligence and wireless connectivity to autonomously communicate with each other, and more particularly, the system disclosed herein relates to a collection of Health Hubs (HH) capable of creating a fully automated digital health social network, that can operate both autonomously (exclusive of any interaction from Human element), as well as through multiple layers of outside individuals and care facilities, including but not limited to, family members, caregivers, and medical care providers. Each digital Health Hubs (HH) can perform various tasks to monitor, record, diagnose and communicate health and safety of individuals. Health Hubs can triage users and analyze their recorded health data to autonomously create public and private social groups, communicate packets of general and detailed information on their users' database within digital Health Hub (HH) Groups. The digital Health Hubs (HH) can join (dock into) or exit (un-dock) from one or more public or private social digital Health Hubs (HH) Groups.

Nowadays, there are modern healthcare solutions that address real world challenges. There are solutions for electronic medical records management and patient engagement, offering a better way to enable doctors and other medical services provider's staff to interact with patients in a secure and friendly environment.

For the reason of convenience, where practicable, it is often preferable for a patient to make health parameter measurements. It is advantageous in allowing patients to perform such measurements and report the data to the clinician. To this end, health monitoring systems need to be developed to provide such measurement and reporting functions. In the past, health monitoring required patients to take these measurements manually and report the results either by telephone or by recording them on paper. The human involvement in this process results in the potential for error in reporting the measurement data. Also, a significant effort is required to record and manage the patient data by the clinician. Cost effective, secure and confidential remote connections between patients and their clinicians can help to prevent serious, episodic, expensive clinical courses and provide a better quality of life for remotely managed patients.

Because clinicians rely on the data to diagnose and advise the patients, the system should present the necessary health data information in an easily understandable format. Also, it will be beneficial for the system to be versatile so as to provide patient information to a variety of related professionals. For example, patients that need attention and follow up need to be flagged using limits for each patient previously provided by the patient's clinician. Individual patient review of measurements provided in a unified view may be needed to provide dependable patient management.

Furthermore, the system should be reliable. A system that fails to report data when measurements are taken or fails to receive the transmitted data when the data are communicated from the measurement device will compromise the effectiveness of a program that monitors the health and well-being of the patient. Although both the clinician and the patient may have the desire to monitor the health parameters of the patient consistently, the patient, being impaired physically, may find it a challenge to perform measurement procedures. Therefore, a system that is complex and requires extensive deftness and multiple steps of manipulation to operate will discourage the patient from complying with a monitoring program prescribed by the clinician. There is a need for a health monitoring system that is easy to use.

Today's patient monitoring environments are crowded with sophisticated sand often electronic medical devices servicing a wide variety of monitoring and treatment endeavors for a given patient. Generally, many if not all of the devices are from differing manufactures, and many may be portable devices. The devices may not communicate with one another and each may include its own control, display, alarms, configurations and the like. Complicating matters, caregivers often desire to associate all types of measurement and use data from these devices to a specific patient. Thus, patient information entry often occurs at each device. Sometimes, the disparity in devices leads to a need to simply print and store paper from each device in a patients file for caregiver review.

Meanwhile, in a traditional health hub where the system connects to medical sensory devices to collect health data. In one example, a wearable platform embodied in a belt or patch provides physiological monitoring of soldiers during field operations or trauma victims at accident sites and makes health state assessments. The platform includes sensors for heart rate, body motion, respiration rate and intensity, and temperature and further contains a microprocessor and short range transmitter. A rule based processing engine having an evaluation algorithm is capable of making a medical evaluation of subject condition and determines a confidence level for the evaluation. The rules are subject to variation depending upon the subject population. The information is communicated wirelessly to a local hub for relay to a remote monitor.

U.S. Pat. No. 6,749,566, issued to Russ on Jun. 15, 2004, describes a system that allows patient monitoring data obtained by patient connected devices to be transferred by wireless signals to another device such as a patient monitoring processor. The same patient connected devices are used to transfer data to the patient monitor processor or a central station depending upon a location of the patient. A single device is used for both a personal area network and a telemetry/transport application. The same wireless technology is used in both situations and eliminates the need to deploy more than one antenna/receiver system. Existing wireless transfer protocols such as Bluetooth are used, thereby reducing transmission power when the two communicating devices are in close proximity. The disclosure shows that it does not provide an automated solution for: a) collect patient monitoring data, b) categories the data in one or more related categories, c) cross match patient categorized data with other patients and form one or more health social groups between patients with common categorical data. Furthermore, the prior art does not provide any means to create links to new secondary "private" health groups for patients with specific needs and goals such as prevention, adherence, etc.

U.S. Pat. No. 9,712,468 issued to Patel on Jul. 18, 2017 describes a social networking device and method that creates a new virtual private network and interface for family members that have shared interests in each other's health, finances, travel, calendars, special events, debts, and physical access to assets. Fundamental to these interests are their individual respective commitments to help one another, and need for automation to assist them with the means needed to be made aware and the tools needed to be effective. A generic family-hub mobile app is downloaded to corresponding mobile devices and independently used by each family member to invite others to join a new family-hub VPN, enroll, share personal information, and access graphical user interfaces (GUI). Several dashboards in the GUI are included with scoreboards for the health, finances, travel, calendars, special events, debts, and physical access to assets of the other enrolled family members. In analyzing this invention, the invention lacks the novel ability for the hub to interact with user and "autonomously" gather health related info from the user, and then utilize that through a unique priority level matching technique to then from Public Hubs with users having common health status. Further, there is also a need provide a proprietor solution for creation of secondary private Hub social groups to address specific needs such as prevention, adherence, etc.

Moreover, the other aspect of traditional health hub is the relay of the collected data to a physician or caregiver. For instance, U.S. Pat. No. 7,978,062 issued to LaLonde et al. on Jul. 12, 2011, discloses a Portable Patient Communicator (PPC) includes a portable housing that supports a processor coupled to memory for storing medical firmware and wireless radio firmware, first and second radios, a processor, and a power source. Communications between a Patient Implantable Medical Device (PIMD) and the first radio of the Portable Patient Communicator (PPC) are effected in accordance with program instructions of the medical firmware, and communications between the second radio of the Portable Patient Communicator (PPC) and the wireless network are effected in accordance with program instructions of the wireless radio firmware. Data from the Patient Implantable Medical Device (PIMD) is received via the first radio to which a priority level is assigned, such as in a tiered manner. A data transport mechanism is selected among disparate data transport mechanisms based at least in part on the priority level. Data from the Patient Implantable Medical Device (PIMD) is transmitted to the wireless network using the selected transport mechanism via the second radio.

Meanwhile, a mobile healthcare hub is described in US Pre-Grant Publication Number 2016/0180044 by Delisle, published on Jun. 23, 2016 includes a processor, memory coupled to the processor and a display coupled to the processor. A communications module includes a mobile communication device configured to communicate with one or more monitoring devices. The one or more monitoring devices are configured to store measurement data and/or historic data for a particular patient. The mobile communications device is connected to the one or more monitoring devices upon entering a communication envelope. An information monitoring module is configured to receive, consolidate and process the measurement data and/or historic data for the particular patient from the one or more monitoring devices based upon relevance and context. A display formatting module is configured to receive the measurement data and/or historic data for the particular patient and format the measurement data and/or historic data for display on the display.

Further, for a medical monitoring hub, described in Japan Patent JP2014533997A, issued to Masimo Corporation on Mar. 29, 2017, describes a medical monitoring hub as a center of the monitoring of the monitored patient. The hub includes configurable medical and serial ports for communication with other medical devices in the vicinity of the patient. In addition, the hub is in communication with the patient monitor of the portable. When the hub is docked to the hub, the hub acts as a monitor presenting a first display graphic. When the hub is not docked, the hub presents a different display; such a display graphic contains anatomical information. In many cases, the hub collects a large amount of electronic medical data associated with the monitored patient. In some embodiments, the hub can be used to communicate data to the medical records associated with the patient.

Another device to communicate data received from a medical device is disclosed in US Pre-Grant Publication 2002/0184415 by Naghavi, published on Dec. 5, 2002. The disclosed device comprises a hosting assembly; an input data port accessible through the hosting assembly and capable of acquiring medical data from a medical device; an output data port accessible through the hosting assembly; and a bi-directional data buffer operatively connected to the plurality of input data ports and the output data port.

Further, an apparatus for reporting a patient's health parameter to a remote data management center was described in U.S. Pat. No. 6,336,900, issued to Alleckson on Jan. 8, 2002. The apparatus includes measurement units and a home hub. A measurement unit includes a sensor for sensing measurements of a health parameter and a transmitter for transmitting wirelessly data derived from the measurements. The home hub receives the wireless transmission of measurement data, processes the measurement unit data for efficient transfer, and transmits selectively data processed by thereby via a public data transmission network to a health data management unit.

Another invention disclosure, described in U.S. Pat. No. 9,436,645, issued to Al-Ali on Sep. 6, 2016, also includes a medical monitoring hub as the center of monitoring for a monitored patient. The hub includes configurable medical ports and serial ports for communicating with other medical devices in the patient's proximity. Moreover, the hub communicates with a portable patient monitor. The monitor, when docked with the hub provides display graphics different from when undocked, the display graphics including anatomical information. The hub assembles the often vast amount of electronic medical data, associates it with the monitored patient, and in some embodiments, communicates the data to the patient's medical records.

Moreover, another system and method is disclosed in US Pre-Grant Publication 2005/0055242 by Bello, published on Mar. 10, 2005 for a remote multi-purpose user interface for medical devices and systems within a healthcare/medication delivery system and/or medication information technology system. The multi-purpose user interface includes a housing, a processor, a memory, a communications interface for providing communication between the user interface and a medical device/controller and for providing communications between the user interface and a first central computer, and a display for displaying a medical prompt and for displaying medical information received from the first central computer. A system and method is also disclosed for medical data tracking, analyzing and reporting within a healthcare system. The disclosed system can further integrate vital signs and infusion pump monitoring and reporting, and allow for enhanced provision of medical care through interface screens which combine this functionality. The system can also provide for control from a central interface screen utilizing this integrated functionality.

Furthermore, a medical sensing system was described in U.S. Pat. No. 9,582,055, issued to De Jong on Feb. 28, 2017. The disclosed medical sensing system includes a data acquisition module operable to receive patient data from a medical sensing device; the data acquisition module being operable to packetize the patient data, a processing module operable to process the packetized first patient data, a user interface module operable to present the processed packetized patient data within a graphical user interface, and a message queue module in communication with the data acquisition module, processing module, and user interface module, the message queue module being operable to receive the packetized patient data from the modules, temporarily store the packetized patient data, and make the packetized patient data available for retrieval by the modules.

Several embodiments of a personal health data hub (PHDH) are described in US Pre-Grant Publication 2014/0195263 by Santos, published on Jul. 10, 2014. The Personal Health Data Hub (PHDH) may include a device that receives health data from Personal Health Devices (PHDs), stores the health data, and sends them to personal health records. Health data may be received by the Personal Health Data Hub (PHDH) using multiple communication technologies, such as Bluetooth, Bluetooth Low Energy, ANT+, Universal Serial Bus (USB), etc. The Personal Health Data Hub (PHDH may be used by different users such as multiple user sessions. Users may access and control the Personal Health Data Hub (PHDH) through different User Interface (UI) mechanisms. The Personal Health Data Hub (PHDH) may interact with users, such as by indicating states and/or events using light and/or sound indicators. The Personal Health Data Hub (PHDH) may use a wireless collector accessory enabled peripheral device to receive health data from a Personal Health Device (PHD). The WCA-enabled device may communicate personal health data to the Personal Health Data Hub (PHDH) on behalf of the Personal Health Device (PHD).

In analyzing the prior art related to the present invention, the limitations and shortcomings of these traditional health hubs is as follows: The traditional method is limited, as the traditional methods rely heavily on the Physician and his/her ability to reliably diagnose the patient's health condition. The disadvantages of traditional health hubs are outlined as follows:

(a) Limited knowledge and information processing by Physicians: One primary factor for above limitations is that the Physician's faculty of "Intellect" and "Knowledge" cannot simultaneously network with other physician's intellect to jointly process data on multiple patients with common symptoms in order to diagnose patients more accurately.

(b) Limited access to information and patient data: Another limitation has to do with the fact that each physician has access to, and can monitor and treat a finite number of patients at a time.

(c) Limited expandability & scalability: Current systems severely limit the ability to expand and scale diagnoses and treatment processes to manage a large number of patients.

(d) Autonomous: The current systems fail to offer an autonomous method to automatically interact with the patient, triage the patient, obtain patient health data and then utilize the obtained information to from health social group with other health hubs sharing a similar health condition.

(e) Vulnerability and dependencies: In the currently known health diagnosis and treatment systems, pulling the human factor (example: Physician or nurse) out of the equation can bring the entire process to a halt.

(f) Self-preventive: The current systems lack any automated, self-preventative methods or solutions to diagnose and treat a patient.

(g) Adaptive: The current systems lack any automated adaptive methods or solutions to diagnose and treat a patient.

(h) Adherence: The current system lack any automated adherence methods or solutions to diagnose and treat a patient.

While there is known technology which describe various forms of health hubs, it is apparent that the known technology lacks any system or method that provides an automated solution to: a) collect patient monitoring data, b) categories the data in one or more related categories, c) cross match patient categorized data with other patients and form one or more health social groups between patients with common categorical data. Furthermore, the known prior art fails to describe any means to create links to new secondary "private" health groups for patients with specific needs and goals such as prevention, adherence.

The system and method described herein provide an innovative and useful solution in this field of digital health hubs.

BRIEF SUMMARY OF THE INVENTION

The present invention is a hub, which generally relates to a collection of digital Health Hubs (HH's) which employs artificial intelligence and wireless connectivity to autonomously communicate with each other to create a fully automated digital health social network. The fully automated digital health social network can operate both (a) autonomously with no interaction from the human element, as well as (b) through multiple layers of outside individuals and care facilities, including but not limited to family members, caregivers and medical care providers.

An autonomous Health Hub (HH) described herein includes a display unit, a microphone, a speaker, multiple sensors, an interactive communication unit, a non-transitory computer readable storage medium, a wireless communication module and at least one data analytics processor in signal communication with the non-transitory computer readable storage medium.

Creation of an Eco-System:

In one object of the present invention, the autonomous Health Hub (HH) creates an Eco-system where the autonomous Health Hubs (HH's) can provide a healthcare environment to triage patients, diagnose patients, and treat patients, without any interaction with medical providers, including: physicians, nurses and caregivers.

The present invention further provides a solution enabling the Health Hubs (HH's) to communicate a) with their users and b) with other Health Hubs (HH's) to form social health groups where one or more Health Hubs (HH's) can join and communicate and share current and historical health information of their corresponding users such as symptoms, medications and historical data, in order for each Health Hub (HH) to better diagnose and treat its individual user. A unique aspect of this approach is the fact that all of the above process to manage the user health care is done by Health Hubs (HH's) without any interaction or assistance from human element such a physician or caregiver.

The present invention additionally provides a fully scalable system of health care with automatic access to an enormous amount of relevant data for diagnosing and treating patients, and as stated above, exclusive of any dependencies on the human factor such as physician.

Interaction with the Autonomous Health Hub User:

The initial step in the creation of the healthcare eco-system is a system which provides interactions between the autonomous Health Hub (HH) and the patient (alternatively referred to as the user herein).

The Health Hub (HH) utilizes various Artificial Intelligence (AI) technologies to communicate with the user in a human-friendly environment.

The Health Hub (HH) then utilizes a built-in microphone to receive and record the user conversation.

Next, the Health Hub (HH) utilizes its built-in Speech To Text (STT) technology to convert user's spoken words into text information, which will result in a collection of words and sentences describing the user conversation.

Following the Speech To Text (STT) process, the Health Hub (HH) utilizes built-in, Natural Language Processing (NLP) algorithms in conjunction with series of pre-stored data bases in its internal storage memory to analyze and understand the user conversation.

Once the user conversation is understood by the autonomous Health Hub (HH), the Health Hub (HH) then accesses a $2^{nd}$ set of internally stored databases to identify the appropriate text responses to communicate back to the user.

Next, the Health Hub (HH) utilizes its built-in Text To Speech (TTS) technology to convert the above mentioned text responses to voice (or speech).

Finally, the Health Hub (HH) utilizes a built-in speaker to communicate the resulting voice responses to the user.

Triaging the Autonomous Health Hub User:

Once a human-friendly method of communication has been established between the autonomous Health Hub (HH) and it's user or users, the Health Hub (HH) then accesses another set of internal data bases to retrieve the necessary question & answer information to guide the Health Hub (HH) to triage the user and obtain data on user's well being. The obtained data is then logged in the internal storage memory of the Health Hub (HH).

Following the initial triage process, the Health Hub (HH) then wirelessly communicates with one or more wireless medical sensors and devices, including but not limited to any wearable wireless device, such as an Electrocardiograph (ECG), a blood monitor, a pulse oximeter, a glucometer, a Thermometer and a digital weight scale, to collect further health data on a condition of the user.

Analyzing the Obtained User Data and Identifying his/her Health Categories:

The autonomous Health Hub (HH) then analyzes the obtained health data of the user, including symptoms of the medical condition of the user in order to identify one or more categories relating to various aspects of the user's health and assigned a pre-determined code to each category. Example of such categories would be a Health Code (HC) representing the user health issue, a Health Level (HL) representing the severity of the above mentioned health issue, an Age Group (AG) referring to a pre-defined general age category which the user falls into, and a Gender Code (GC) representing a gender affiliation of the user. As stated above, this entire process is managed by the autonomous Health Hub (HH), with no interaction or assistance from a Human factor, such as a physician or caregiver.

Creating Data Packets and Assigning Health Priority Levels:

Among the unique objectives of the autonomous Health Hub (HH), is the formation of General Data Packets (GDP) and assignment of Health Priority Levels (HPL) associated with the autonomous Health Hub (HH) and the associated user.

The above mentioned Health Categories within the Health Eco-system are utilized to form one or more General Data Packets (GDP) repressing the General Health status of the user.

All autonomous Health Hubs (HH's) within the Health Eco-system network then communicate their user's General Data Packets (GDP) to a Central Health Hub (CHH) within the health system. Central Health Hub (CHH) analyzes each General Data Packet (GDP) received and assigns a Health Priority Level (HPL) to each Health Hub (HH) relative to other Health Hubs (HH's) within the network. The Health Priority Level (HPL) is determined by assigning an "importance value" to each of the categories within the General Data Packet (GDP). Highest value will get assigned to the most critical categories. A binary system is then utilized to calculate and assign the appropriate Health Priority Level (HPL) to each Health Hub (HH). Once again, as stated above, this entire process is managed by the autonomous Health Hub (HH), with no interaction or assistance from Human factor, such as a physician or caregiver.

Formation of Social Health Groups:

Yet, another objective within the autonomous Health Hub (HH) is the formation of Public Social Health Groups for various Health Hubs (HH's) to join and communicate with each other to better diagnose and treat their user base.

The above established Health Priority Level (HPL) enables autonomous Health Hubs to identify one or more Health Hubs (HH's) within the network with their users having similar General Data Packets (GDP) information, meaning their users sharing similar medical issue, health severity, age, gender and so on. The identified Health Hubs (HH's) then communicate with either to form a public social health group. Once the social health group is formed, each individual Health Hub (HH) can gain access to valuable current and historical data on similar patients as its own user. With the above described system being automatically scalable as more and more Health Hubs (HH's) join the network, the autonomous Health Hub (HH) will have the unique ability to diagnose and treat its user by having instantaneous access to massive amount of relevant information. Again, as stated above, this entire process is managed by current invention, autonomous Health Hub (HH), with no interaction or assistance from the human factor, such as a physician or caregiver.

Formation of Special Purpose Social Health Groups.

Another novel object within the current invention is the ability to form special purpose social health groups to address specific needs within the healthcare process. One example of such social groups is a preventive social health group.

Autonomous Health Hubs can utilize the above-established Health Priority Level (HPL) to identify and communicate with other Health hubs within the network with users sharing the same medical issues, however having a higher severity of health or Health Level (HL), or being in a higher Age Group (AG) and so on. The identified Health Hubs (HH) can then form a Preventive Social Health Group together. This enables the member Health Hubs (HH) to access and analyze current and historical health data such as, symptoms, medications and treatment history of more Sevier patients in the group in order to better identify a treatment method for preventing a more sever health outcome. Once again, as stated above, this entire process is managed by current invention, autonomous Health Hub, with no interaction or assistance from the Human factor, such as a physician or caregiver.

It is another object of the present invention to provide an autonomous Health Hub (HH) capable of interactively communicating with the user by utilizing Text To Speech (TTS), Speech To Text (STT) and Natural Language Processing (NLP) technologies.

It is another object of the present invention to interactively utilize the above the Text To Speech (TTS), Speech To Text (STT) and Natural Language Processing (NLP) to triage the user and gather and record information on the user's health status, treatments and medications being taken.

It is another object of the present invention to communicate with one or more medical sensory devices including but not limited to a blood monitor, pulse oximeter, glucometer and electrocardiograph device to collect and record further detail information on the patient health status.

It is another object of the present invention to organize the collected user data into one or more categories, including but not limited to user health (Health Code) category, severity of health condition (Health Level) category, age (Age Group) category and gender (Gender Code).

It is another object of the present invention to access a pre-defined category code database of codes and assign the corresponding category code to each of the user health categories.

It is yet another object of the present invention to create General Data Packets (GDP) comprising of the assigned category codes for the user.

It is yet another object of the present invention to determine a Health Priority Level (HPL) for autonomous Health Hubs (HH's) as related to other Health Hubs (HH's) within the system, based on the commonality (overlap) of their assigned category codes within their General Data Packets (GDP).

It is another object of the present invention is the formation of one or more Public Health Groups, each comprising one or more autonomous Health Hubs (HH's) based on their Health Priority Level (HPL) as related to each autonomous Health Hub (HH) in the system. Public Health Groups comprising of Health Hubs (HH's) with the most common category codes to the autonomous Health Hub (HH) will be assigned the highest priority Public Health Group (PHG).

It is another object of the present invention for the autonomous Health Hubs (HH's) ability to automatically form one or more special purpose Private Health Groups based on the information contained within the General Data Packet (GDP).

It is another object of the present invention for the autonomous Health Hubs (HH's) ability to form adherence private health group with one or more health Hubs (HH's) that having the same priority health level. The autonomous Health Hubs (HH's) within the same adherence private health group share common a health category and a health severity and can assist each other's users to comply with medication schedules and reminders.

It is another object of the present invention for the autonomous Health Hubs (HH's) ability to form preventive private health group with one or more Health Hubs (HH's) that having higher priority health level. Within a preventive private health group, an autonomous Health Hub (HH) can access historical data, treatments and treatment results of health hub users with more severe health issues (higher health priority level), in order to more accurately forecast their future health improvement and prevent downfalls.

It is another object of the present invention for the autonomous Health Hubs (HH's) ability to form private social health groups based on the user-selected categories within the General Data Packet (GDP).

It is another object of the present invention to provide a computer program comprising a set of instructions stored in non-transitory computer readable medium. The computer program instructions are executable by a processor. The computer program instructions comprising instructions for receiving health profile data from a plurality of network members, each network member having a plurality of established data entries within a plurality of categories. The computer program identifies at least one category of a first network member and creates a first data packet based on the data entered for that category; compares the first data packet of the first network member to the other data packets of other network members, ranks the commonalities of each categories by importance and relevancy, and determines and sets a priority level for each of the other data packets in relation to the first data packet. The computer program identifies a grouping of data packets, defining a first subset of the data packets of all network members, wherein the grouping of data packets includes the first data packet and at least one other data packet, the other data packet having the highest priority level. The computer program continues by analyzing the first subset of data packets, determines and diagnoses the current health problems of the members of the first subset, forecasts future health issues of the members of the first subset, creates a course of treatment for current and forecasted health issues; and reports the course of treatment to the first network member.

It is another object of the present invention to provide instructions within the computer program for a second subset of the data packets of all network members. The second subset of the data packets includes the first data packet and at least one other data packet, the other data packet having the same priority level as the first data packet.

It is another object of the present invention to provide instructions within the computer program that enable analyzing the at least one subset of data packets, determining and diagnosing the current health problems of the members of the at least one subset, and assisting with medication and treatment adherence of current health issues of the members of the subset.

It is another object of the present invention to provide a system and method enabling diagnosing and treating members within a network. Each member within the network has a Health Hub (HH) networked to the other Health Hubs (HH's) via a wireless communication, locally or remotely from each other. The system and method includes capabilities of: interacting with a first member associated with a first Health Hub (HH); receiving health profile data of the member; identifying at least one health category of the first member and creating a first data packet based on the data entered for the at least one category. The system and method additionally includes capabilities of: creating similar other data packets for all other network members; comparing the first data packet to the other data packets of the other network members, ranking the commonalities of each category by importance and relevancy, and determining and setting a priority level for each of the other data packets in relation to the first data packet. The system and method further includes capabilities of: identifying a grouping of data packets, defining a first subset of the data packets of all network members that includes the first data packet and at least one other data packet, the other data packet having the highest priority level. The system and method continues with capabilities of: analyzing the first subset of data packets, determining and diagnosing the current health problems of the members of the first subset, forecasting future health issues of the members of the first subset, and creating a course of treatment for current and forecasted health issues; and reporting the course of treatment to the first network member.

It is another object of the present invention to provide a step of interacting with network members.

It is another object of the present invention to provide a step of interacting with network members using at least one technique selected from the group consisting of Speech To Text (STT), Text To Speech (TTS) and Natural Language Processing (NLP).

It is another object of the present invention to provide a step of utilizing an Artificial Intelligence (AI) Avatar virtual assistant to interact with network members.

It is another object of the present invention to provide a step of utilizing Artificial Intelligence (AI) to diagnose and interact with network members.

It is another object of the present invention to provide a step of accessing and utilizing available other wireless medical devices of network members to collect details and additional health data regarding their respective network members.

It is another object of the present invention to provide a step of accessing and utilizing available other wireless devices of network members to collect details and additional health data regarding their respective network members.

It is another object of the present invention to provide a step of accessing and utilizing available other wireless applications of network members to collect details and additional health data regarding their respective network members.

It is another object of the present invention to provide a step of utilizing medical devices outside the Health Hub (HH) of a network member to collect detail health data on the member associated with the Health Hub (HH).

It is another object of the present invention to provide a step of defining a second subset of the data packets of all network members that includes network members having lower priority than that of the first member, analyzing the health data of the second subset, determining preventative treatment methods for the first network member, and reporting the preventative treatments to the first network member.

It is another object of the present invention to provide a step of allowing and facilitating network members to create groups and communicate through the Health Hub (HH) with other network members within the group and individually.

It is another object of the present invention to provide a step of communicating autonomously by the Health Hub (HH) of the first member with the Health Hubs (HH's) of other network members, forming a grouping of a plurality of members having at least one common health condition and having a common priority level, and assisting with the group's members' adherence in taking medications.

It is another object of the present invention to provide a Health Hub (HH) apparatus capable of interacting with a user to triage, collect health data, form data packets related to user health and its severity, autonomously communicate with other Health Hubs (HH's) within a network, and share the collected information with other Health Hubs (HH's), analyze the shared information and determine treatment for the user, the apparatus comprising: a processor; a memory; an interface display; a microphone; a speaker; a speech to text (STT) and text to speech (TTS) processing module, the processing module further having a communicator to communicate with a user. The Health Hub (HH) additionally includes an Artificial Intelligence (AI) module. The Artificial Intelligence (AI) module includes an Avatar, wherein the Avatar is provided to interact with the user; a Natural Language Processing (NLP) module. The Artificial Intelligence (AI) module further having an analyzer for analyzing the user communicated information. At least one health data packet is stored within the Health Hub (HH), the data packet containing at least one user health category and at least one severity level of the user's health. The health Hub (HH) additionally includes a wireless transceiver; the wireless transceiver includes a communication hub, wherein the communication hub enables communication with other Health Hubs (HH's) within a network. The communication enables sharing of collected health information. The health Hub (HH) additionally includes a user interface. The Health Hub (HH) further comprises a health level priority assigner operating on the processor, the health level priority assigner assigns a Health Priority Level (HPL) to the data packet of the user and to data packets of the other Health Hubs (HH's) within the network. The Health Hub (HH) further comprises a first group creator operating on the processor, the first group creator autonomously forms at least one health group from the other Health Hubs (HH's) within the network based on the assigned Health Priority Level (HPL). The Health Hub (HH) further comprises a second group creator operating on the processor, the second group creator having a health identifier which identifies and creates a second health group with network members sharing similar health issues with more severe state. The Health Hub (HH) further comprises a treatment module operating on the processor, the treatment module having a health diagnostics module, a treatment plan module, a preventative treatment module, and a reporting module to report the health diagnosis, the treatment plan, and the preventative treatment plan.

It is another object of the present invention to provide a Health Hub (HH) to utilize one or more wireless medical devices to collect health and vital information from the user associated with each Health Hub (HH).

It is another object of the present invention to provide a proximity sensor, the proximity sensor is provided to detect the presence of an outside wireless computing device.

It is another object of the present invention to provide a biometric scanning device to securely identify the presence of the authorized user.

It is another object of the present invention to enable the wireless transceiver to pair with one or more mobile devices when the paired mobile devices are within close proximity of the health hub.

It is another object of the present invention to provide a treatment monitor, wherein the previously identified health groups comprised of members having the same health issues and the same health severity, utilize the treatment monitor to form adherence health groups for member Health Hubs (HH's) to assist each other in adherence with medications and treatments.

It is another object of the present invention to provide a health forecaster, wherein the health forecaster identifies health groups comprised of members having the same health issues but differ in their age category, to form forecast health groups for member Health Hubs (HH's) to help forecast the impact of medication usage and treatments in younger users as they age.

It is another object of the present invention to provide a health priority module, wherein Health Priority Levels (HPL's) are determined by assigning a unique numeric value to each category of the health data packet, with the more severe health categories assigned a higher numeric value than the less severe ones.

It is another object of the present invention to provide an Artificial Intelligence (AI) module to collect and triage health information of a user.

The following are several examples of use that further illustrate the unique and useful nature of the autonomous Health Hub (HH), as well as the objectives stated above.

Example Case: Arrhythmia Patient

One example presents a patient with cardiovascular health issues. The user has a mild heart problem or Arrhythmia. The Health Hub (HH) uses Text To Speech (TTS), Speech To Text (STT) and Natural Language Processing (NLP) to interactively communicate with the user and help triage him or her. The Health Hub (HH) then creates a new General Data Packet GDP) for the user and saves the General Data Packet GDP) in the internal storage memory of the Health Hub (HH). The Health Hub (HH) assigns a Health Code (HC) associated with mild Arrhythmia to the user. The Health Hub (HH) then performs additional triage on the user, as well as utilizing wireless health diagnostic devices such as an ECG device, to determine severity of user Arrhythmia and assigns the appropriate Health Level (HL) to the User General Data Packet. It utilizes a pre-stored User Age chart to determine appropriate Age Group (AG) for the User and assigns the Age Group (AG) code to the User General Data Packet. The Health Hub (HH) also utilizes a pre-stored User Gender chart to determine appropriate Gender Code (GC) for the User and assigns the appropriate Gender Code (GC) code to the User General Data Packet. The Health Hub (HH) also communicates with the Central Health Hub (CHH) to assign a Unique User ID (UID) Number (if not one assigned yet) for the user and include the assigned Unique User ID (UID) code in the User General Data Packet.

Next, a new Detail Data Packet (DDP) is created for the user. The Health Hub (HH) creates the new Detail Data Packet (DDP) for the user, the Detail Data Packet (DDP) comprising the General Data Packet (GDP) above as its header information. The Health Hub (HH) further utilizes one or more medical diagnostic devices to obtain more specific data on the user's health status to be added to the Detail Data Packet (DDP) which could include a blood pressure monitor, an Electrocardiograph (ECG), and a pulse oximeter. The Detail Data Packet (DDP) further includes information on prescribed medications and treatment plans. The Health Hub (HH) then stores the detail data packet in its internal storage memory.

A next step would be to create and join a Public Health Group (PHG). Following the creation of the General data Packet (GDP) and the Detail Data Packet (DDP), the Health Hub (HH) communicates the user General Data Packets (GDP's) to the Central Health Hub (CHH). The Central Health Hub (CHH) then compares all categories within the user's General Data Packet (GDP). In this example, the General Data Packet (GDP) includes the Health Code (HC), the Health Level (HL), the Age Group (AG) and the Gender Code (GC) to those of other public health group within the entire network. The Central Health Hub (CHH) also obtains the link information for all public groups along with their matching Priority Level (PL) with respect to the requesting Health Hub (HH) and provides that link information to the Health Hub (HH). Finally, the Health Hub (HH) utilizes the link information to communicate with other Health Hubs (HH's) within the determined public health social group.

Next, one or more special purpose private health groups are created. One example of such special private health groups is an "adherence" health group. The autonomous Health Hub (HH) can automatically create an adherence private health group to address the user adherence needs with taking medication and complying with treatment procedures. In the adherence private health hub group, the autonomous Health Hub (HH) communicates with one or more other autonomous Health Hubs (HH's) within its own public health hub group, where all autonomous Health Hubs (HH's) share a similar Health Code (HC), a similar Health Level (HL), a similar Age Group (AG), and a similar Gender Code (GC) and requests other Health Hubs (HH's) to join a private health hub group. In the current example, all autonomous Health Hubs (HH's) represent users with mild heart problem or Arrhythmia and share similar severity of health. The resulting members of the above newly formed private health group can compare and coordinate medications, dosages, medication schedule, symptoms, and their outcome with other autonomous Health Hubs (HH's) in the group and provide reminders to each other to assist with medication and treatment adherence.

Another example of special private health group is a "preventive" health group. In case of the above the user, the autonomous Health Hub (HH) automatically identifies other Public Health Groups (PHG's) in the network with their Health Hub (HH) users being treated for Arrhythmia (similar Health Code (HC) in their General Data Packet (GDP) who are experiencing more severe symptoms (having a higher Priority Level (HL)). To achieve this, (1) the autonomous Health Hub (HH) creates an initial table containing links to all Public Hub Groups (PHG's) with Health Hub (HH) members having an Arrhythmia Health Code (HC), (2) the autonomous Health Hub (HH) then selects links to the Public Hub Groups (PHG's) with the higher Health Level (HL) in their General Data Packet (GDP), and (3) the autonomous Health Hub (HH) then communicates with one or more Health Hubs (HH's) within the selected Public Health Group (PHG) and sends a request to join a private health group. Finally, the autonomous Health Hub (HH) utilizes the above data analysis along with other Health Hub (HH) member's historical health data recordings to determine a preventive treatment course to maintain or reduce user's health priority level (health severity).

Example Case: Artificial Intelligence (AI) Therapy utilizing Virtual Assist for PTSD Treatment:

Following the process of the above example with cardiovascular patients, the autonomous Health Hubs (HH's) can automatically create private health groups assisting veterans dealing with Post-Traumatic Stress Disorder (PTSD). The autonomous Health Hub (HH) interactively communicates with the user, utilizing the Artificial Intelligence (AI) virtual Assistant, and the supported Text To Speech (TTS), Speech To Text (STT) and Natural Language Processing (NLP) technologies. The Speech To Text (STT) technology allows the user to interactively speak to the Artificial Intelligence (AI) virtual assistant Avatar of the autonomous Health Hub (HH) and have the user's speech translated into text information that can then be analyzed and processed through internal database information. Additionally, the Text To Speech (TTS) technology then allows the information accessed and analyzed by the Artificial Intelligence (AI) virtual assist Avatar on the autonomous Health Hub (HH) to be converted to speech and communicated to the user interactively. Utilizing the Natural Language Processing (NLP), this technology allows the Avatar Artificial Intelligence (AI) on the Health Hub (HH) to analyze and "understand" the interactive conversation contents and help triage the user accordingly.

The autonomous Health Hub (HH), through the use of the Artificial Intelligence (AI) virtual assist is capable of providing the "anonymity" factor often required for an effecting therapy. In one configuration, the Artificial Intelligence (AI) virtual therapy session can be created as a single-user session between the Artificial Intelligence (AI) virtual assist and the health hub user, in this case the veteran suffering from PTSD. Yet in another configuration, the Artificial Intelligence (AI) virtual assist can create a "group settings" and provide interactive therapy session for multiple users by utilizing the above mentioned Text To Speech (TTS), Speech To Text (STT) and Natural Language Processing (NLP).

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings, which are the purpose of illustration only and not limitation, and in which.

DETAILED DESCRIPTION OF INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope, and contemplation of the present invention.

It should be noted that references to "an," "one," or "various" embodiments in this disclosure are not necessarily to the same embodiment, and such references contemplate more than one embodiment.

The present invention disclosed herein and illustrated in FIGS. 1 through 31 is a collection of autonomous digital Health Hubs (HH) with Artificial Intelligence (AI) to autonomously communicate with each other to create a fully automated digital health social network.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current good manufacturing practice guidelines.

As used herein the term "Computing Device"" includes a desktop, laptop or tablet computer, as well as a mobile device.

Figure 1:
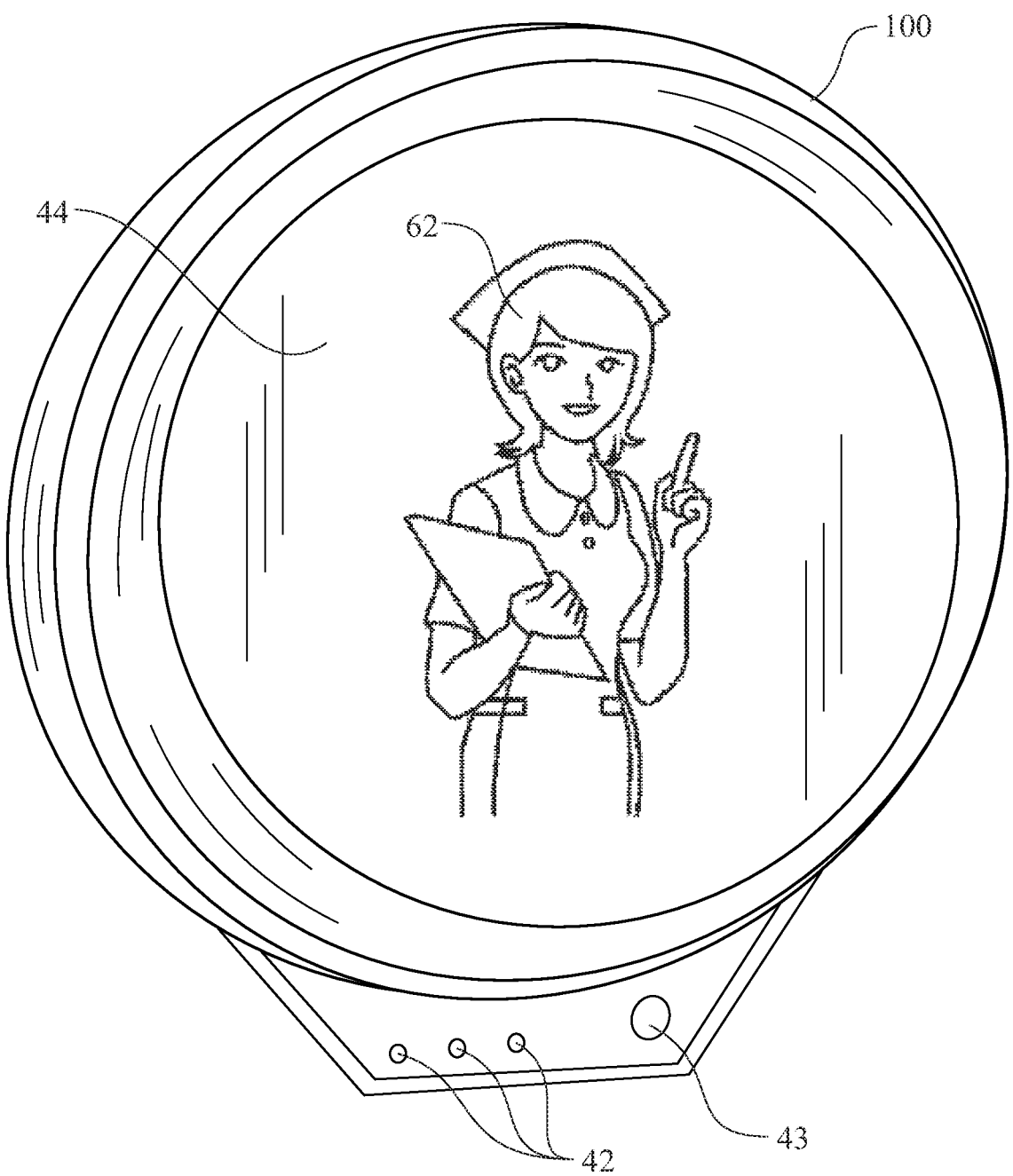
FIG. 1 presents a perspective view of an exemplary autonomous Health Hub (HH)

An autonomous Health Hub (HH) 100 is introduced in FIG. 1. The autonomous Health Hub (HH) 100 includes a display unit 44, a microphone 43, a speaker 42, and an Artificial Intelligence (AI) Avatar virtual assistant 62.

Figure 2:
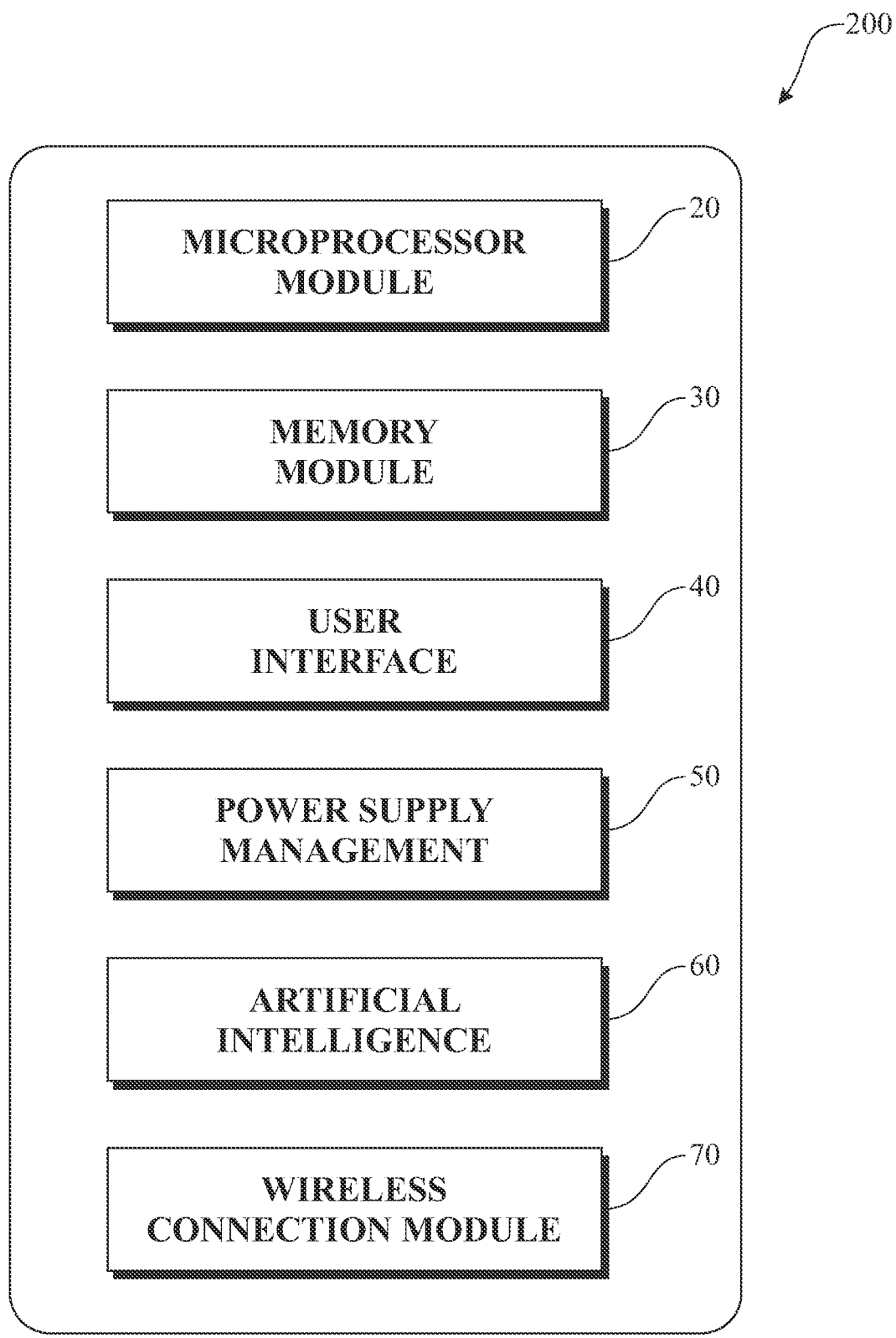
FIG. 2 presents a schematic block diagram of the hardware structure of the autonomous Health Hub (HH) originally introduced in FIG. 1.

A hardware structure 200 of the autonomous Health Hub (HH) 100 is illustrated in FIG. 2. The hardware structure 200 includes a microprocessor module 20, a memory module 30, a user interface 40, a power supply management module 50, an artificial intelligence module 60 and a wireless communications module 70.

Figure 3:
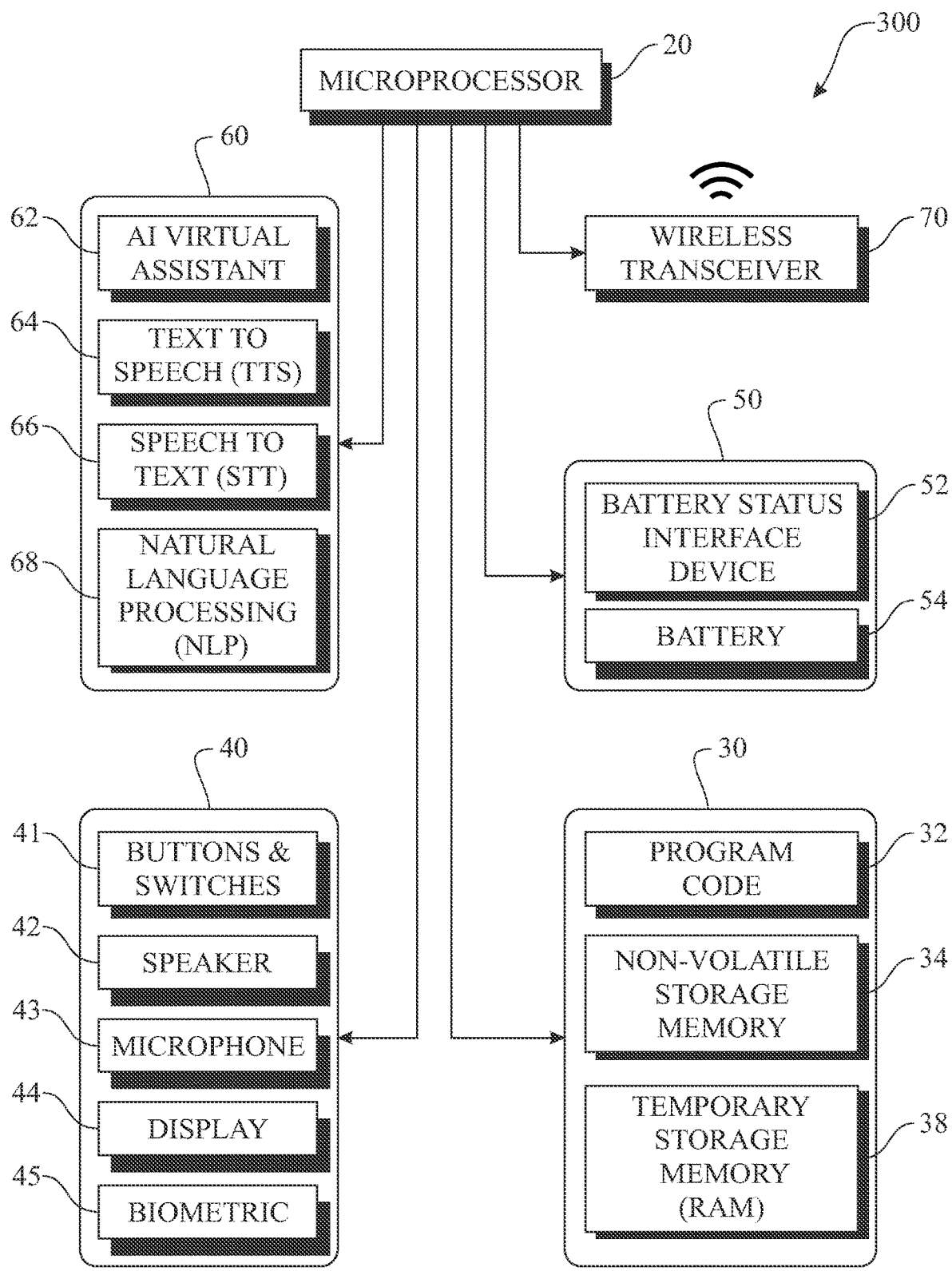
FIG. 3 presents an exemplary hardware flow diagram of the hardware structure of the autonomous Health Hub (HH) originally introduced in FIG. 1.

A more detailed hardware structure 300 of the autonomous Health Hub (HH) 100 is presented in FIG. 3. The hardware architecture 300 is contained within an appropriate housing, an example of one such embodiment is shown in FIG. 1. The autonomous Health Hub 100 includes a microprocessor 20 that provides the computing power, a wireless transceiver 70 that provides communication with outside wireless devices. A user interface module 40 of the autonomous Health Hub (HH) 100 includes a display unit 44 for viewing various prompts and messages. The display unit 44 is further utilized for viewing and interacting with the Artificial Intelligence (AI) virtual assistant 62. The user interface module 40 also includes a plurality of buttons and switches 41, an audio speaker device 42 to prompt the operator, a microphone 43, and a display 44. The user interface module 40 also includes a biometric reader 45 to securely identify an authorized user of the autonomous Health Hub (HH) 100. A battery power management module 50 contains a rechargeable battery 54 that provides power to the autonomous Health Hub (HH) 100, and battery condition supporting circuitry 52 that provides feedback associated with a status of the battery, such as when a charger is available. A memory module 30 provides a digital storage area 32 for internal programming, as well as storing various information related to each patient and each medication container 110, a non-volatile storage memory 34, and a temporary storage memory or Random Access Memory (RAM) 38. An Artificial Intelligence (AI) module 60 includes supporting components for the Artificial Intelligence (AI) Virtual Assistant 62, including: Text To Speech (TTS) 64, Speech To Text (STT) and Natural Language Processing (NLP) 68 support circuitry and components.

Figure 4:
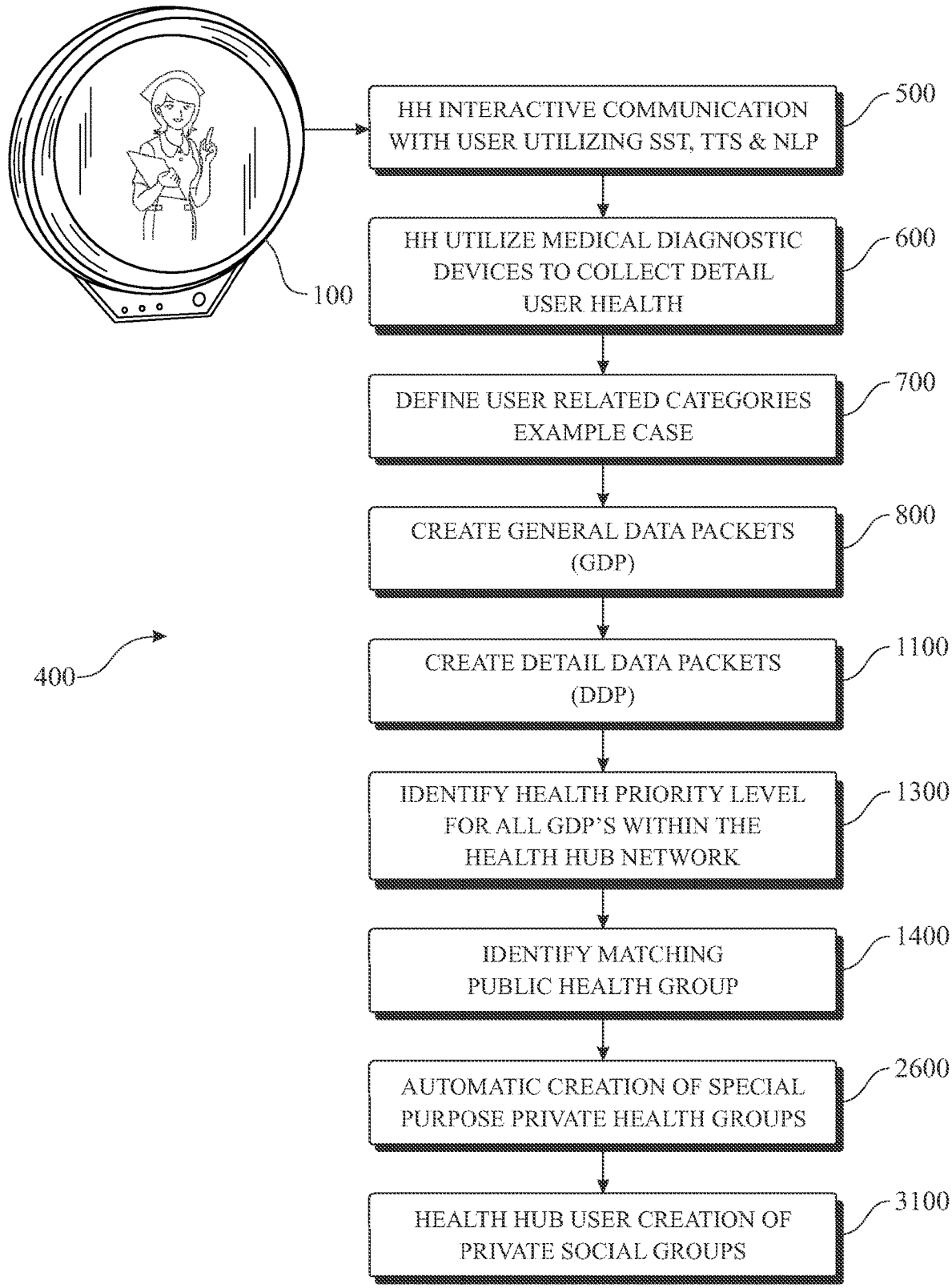
FIG. 4 presents an exemplary flow diagram of a formation of public and private health groups using the autonomous Health Hub (HH) originally introduced in FIG. 1.

An overview of a group formation process 400 for forming an autonomous Health Hub public group and a private Health Group is presented in FIG. 4. The autonomous Health Hub (HH) 100 interactively communicates with the user 99 (FIG. 5), utilizing the Artificial Intelligence (AI) Virtual Assistant 62, and the supported Text To Speech (TTS) 64, Speech To Text (STT) and Natural Language Processing (NLP) 68 modules (step 500, detailed in FIG. 5). Next, the autonomous Health Hub 100 communicates with one or more medical diagnostic devices (step 600, detailed in FIG. 6) to further triage the user 99 and collect detail health data associated with the user 99. One or more category related to the user is then defined as demonstrated in the example case (step 700, detailed in FIG. 7). Utilizing the above mentioned categories, at least one General Data Packet (GDP) 810 is then created (step 800, detailed in FIG. 8) for the user 99. Next, at least one Detail Data Packet (DDP) (step 1110, detailed in FIG. 11) is created. Each Detail Data Packet (DDP) consists of the data stored in the above mentioned General Data Packet (GDP) as its primary header information along with the patient detail recorded health data through the use of medical diagnostic devices. Following the formation of General Data Packet (GDP) and Detail Data Packet (DDP), a Health Priority Level (HPL) 1310 of all General Data Packets (GDP's) within the Health Hub Network is determined (step 1300, detailed in FIG. 13). Following the determination of each General Data Packet's Health Priority Level 1310, at least one public health group 1410 is formed, each group comprising of one or more autonomous Health Hubs (HH's) 100 with matching health priority level (step 1400, detailed in FIG. 14). Next, the autonomous Health Hub (HH) 100 forms one or more special purpose private health groups 2710 with other autonomous Health Hubs (HH's) 100 having either a lower or a higher health priority level (step 2600, detailed in FIG. 26). Finally, each user 99 of the autonomous Health Hub (HH) 100 can create at least one private social group (step 3100, detailed in FIG. 31).

Figure 5:
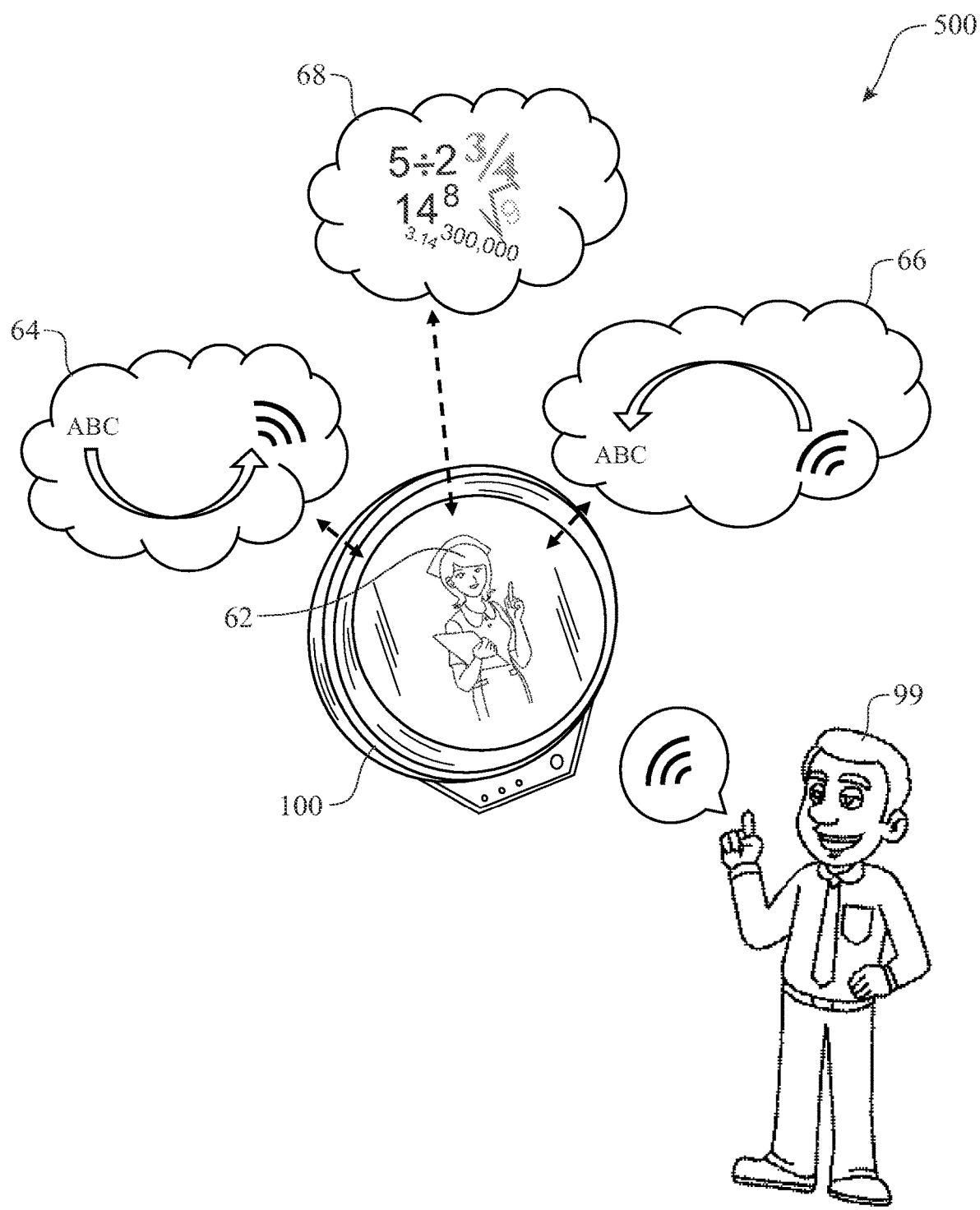
FIG. 5 presents an exemplary functional schematic diagram illustrating interactive communication between a user and the exemplary autonomous Health Hub (HH) originally introduced in FIG. 1.

The autonomous Health Hub (HH) 100 having interactive communication with the user 99, wherein step 500 is illustrated in a schematic format in FIG. 5. The system accesses built-in data base of topics and related question form internal storage. The Artificial Intelligence (AI) Avatar virtual assistant 62 then communicates interactively with the user 99 by utilizing the following: (a) Text To Speech technology (TTS) 64 to provide audible messages for the user 99, (b) Speech To Text technology (STT) 66, to convert voice audio from the user 99 and (c) Natural Language Processing Technology (NLP) 68 to analyze and understand communications from the user 99. The Artificial Intelligence (AI) Avatar virtual assistant 62 then triage the user 99, collects information and stores the collected information in the internal non-volatile storage memory 34.

The Speech To Text (STT) 66 technology allows the user 99 to interactively speak to the Artificial Intelligence (AI) Avatar virtual assistant 62 on the autonomous Health Hub (HH) 100, and have his/her speech translated to text information that can then be analyzed and processed through internal database information. The Text To Speech (TTS) 64 technology then allows the information accessed and analyzed by Artificial Intelligence (AI) Avatar virtual assistant 62 on the autonomous Health Hub 100, to be converted to speech and interactively communicated to the user 99. The Natural Language Processing (NLP) 68 technology allows the Artificial Intelligence (AI) Avatar virtual assistant 62 on the Health Hub to analyze and "understand" the interactive conversation contents and help triage the user 99 accordingly.

Figure 6:
FIG. 6 presents an exemplary functional schematic diagram illustrating employment of various medical diagnostic devices and the exemplary autonomous Health Hub (HH) originally introduced in FIG. 1, wherein the various medical diagnostic devices are employed to collect user health information.

The autonomous Health Hub (HH) 100 is shown utilizing one or more wireless medical devices to triage the user 99, wherein step 600 is illustrated in a schematic format in FIG. 6. The system accesses a built-in data base of topics and a related question from the internal storage 34. The Artificial Intelligence (AI) Avatar virtual assistant 62 then communicates interactively with the user 99 by utilizing Speech To Text (STT) 66, Text To Speech (TTS) 64 and Natural Language Processing (NLP) 68. The autonomous Health Hub (HH) 100 then communicates wirelessly with one or more wireless medical devices 601, 605, 603, 604, 699, triages the user 99, collects detail information through the use of the wireless medical devices 601, 605, 603, 604, 699 and stores the collected information in the internal storage memory 34. Examples of wireless medical devices 601, 605, 603, 604, 699 presented include: a pulse oximeter 601, a blood pressure monitor 602, a scale 603, a glucometer 604, and other medical devices 699.

Figure 7:
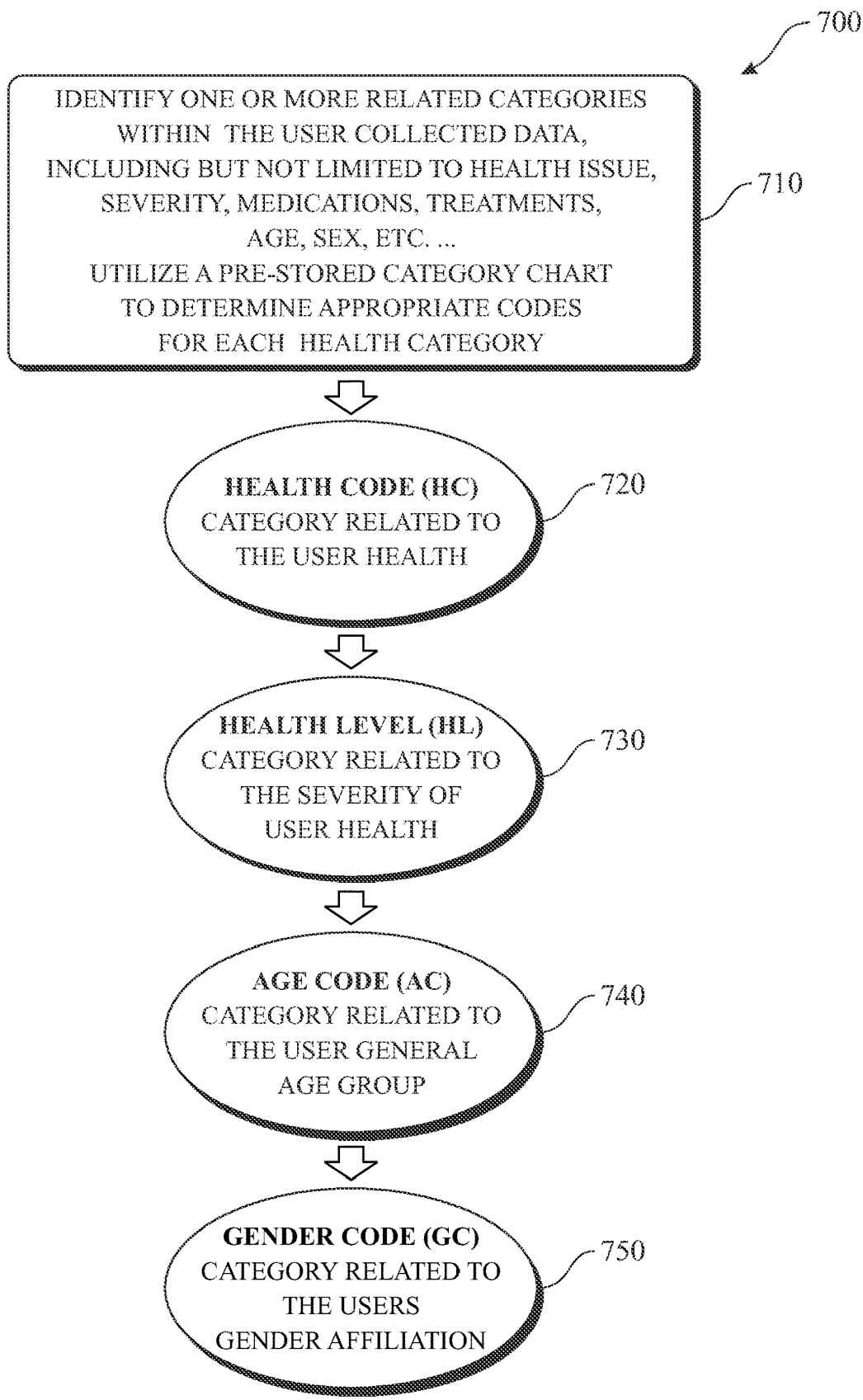
FIG. 7 presents an exemplary flow diagram for defining user related categories.

One or more related categories within the user collected data, including but not limited to: a health issue, severity, medications, treatments, age, sex, etc., are identified in an exemplary schematic diagram representing step 700 presented in FIG. 7. Next a pre-stored category chart in the internal non-volatile storage memory 34 of the autonomous Health Hub (HH) 100 is utilized to determine appropriate codes for each of the health categories. Examples of health categories shown include a general Health Code (HC) 720, a severity of user Health Level (HL) 730, a user's Age Group (AG) 740 and a user's Gender Code (GC) 750.

Figure 8:
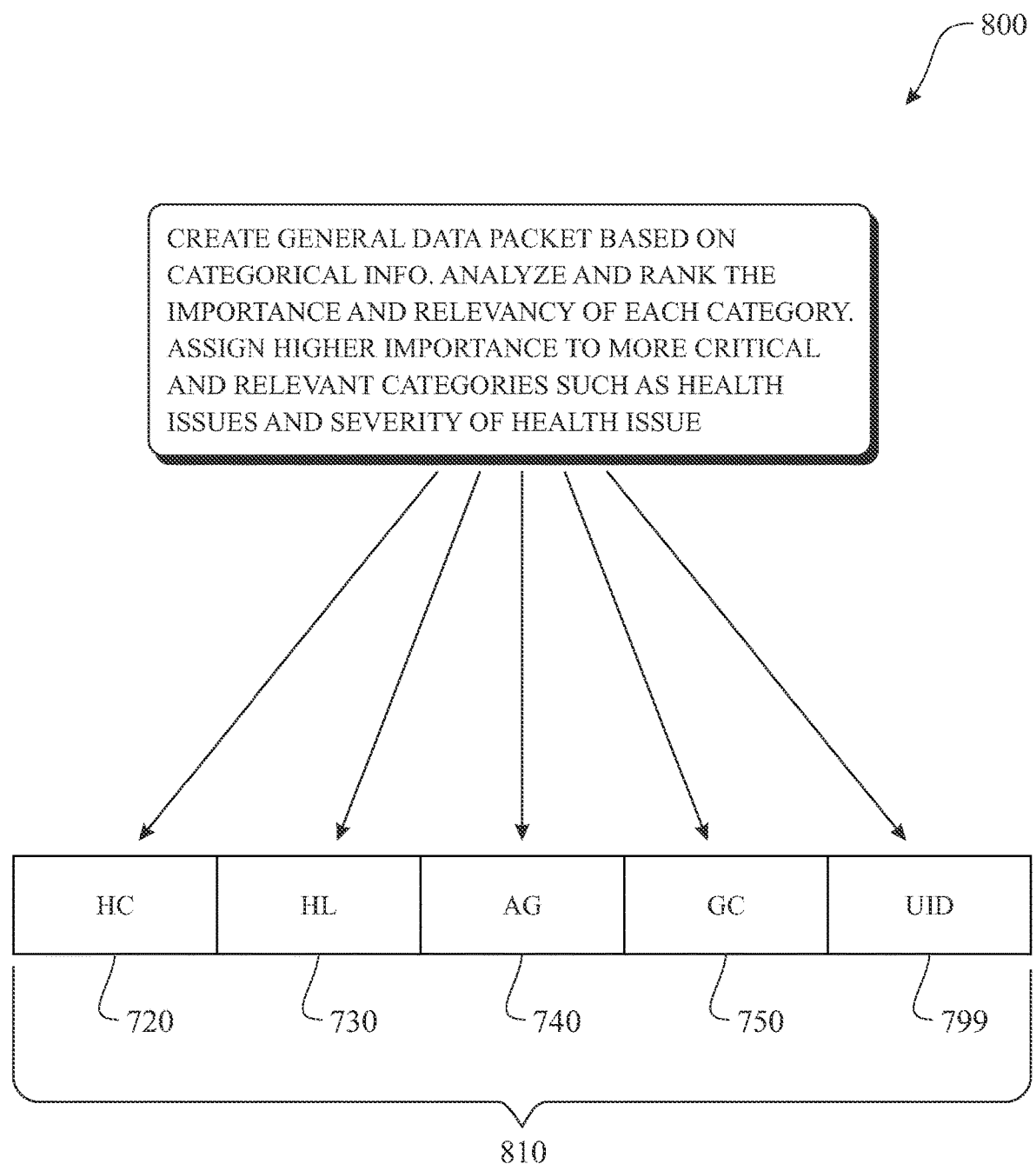
FIG. 8 presents an exemplary block diagram of an exemplary General Data Packet (GDP)

Details pertaining to the General Data Packet (GDP) 810 are provided in a block diagram representing step 800 shown in FIG. 8. The General Data Packet (GDP) 810 is arranged in a block format including one or more components. In the block diagram, the exemplary General Data Packet (GDP) 810 comprises five (5) components: (a) the Health Code (HC) 720, which represents the user health category, such as diabetes, blood pressure, cardiovascular and so on; (b) the Health Level (HL) 730 which represents the general category related to the severity of the health condition of the user within the health category above (as an example for a diabetes patient, the Health Level (HL) 720 can represent Diabetes Type-1 or Type-2); (c) the Age Group (AG) 740 which represents one or more general age category of the user (an example of age categories could be in group ages for infants, 1 to 5 Years, 6 to 12 Years, 13 to 21 years, and 65 years & older); (d) the Gender Code (GC) 750 which represents a users gender affiliation; and (e) the User ID (UID) 799, which is a unique identification number assigned to each user by the Central Health Hub (CHH) 1490.

Figure 9:
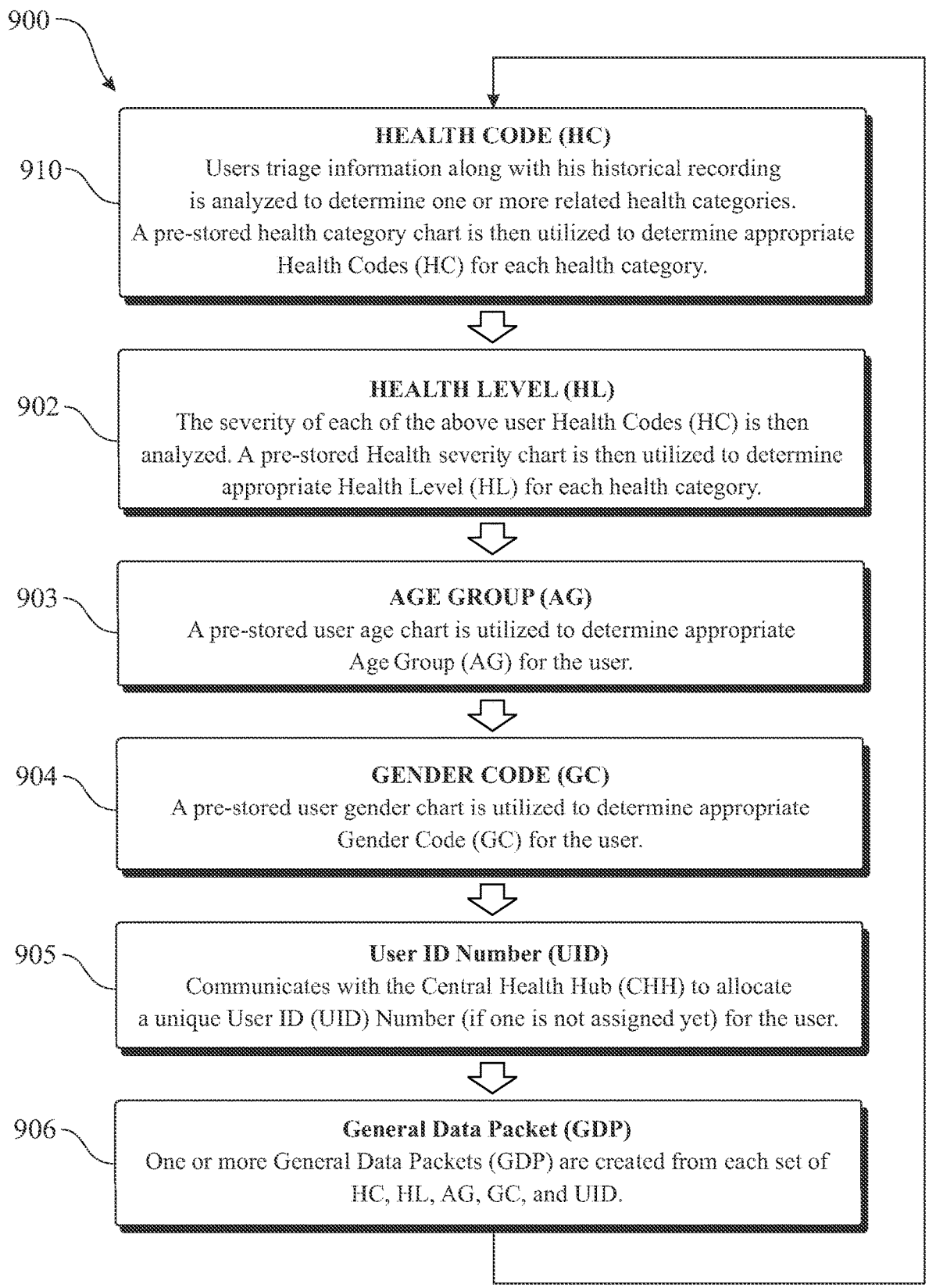
FIG. 9 presents an exemplary flow diagram for creating a General Data Packet (GDP)

A flow chart 900 describes steps for creating the General Data Packet (GDP) 810 is presented in FIG. 9. As illustrated in block 901, user triage information is analyzed to determine at least one health related category which is then identified by a Health Code (HC) 710. In block 902, the severity of each of the above at least one Health Code (HC) 720 is then identified by the associated Health Level (HL) 730. Next, in block 903, a pre-stored user age chart is utilized to determine the appropriate Age Group (AG) 740 associated with the user. As illustrated in block 904, a pre-stored user gender chart is utilized to determine an appropriate Gender Code (GC) 750 for the user. Continuing, as shown in block 905, the autonomous Health Hub (HH) 100 communicates with the Central Health Hub (CHH) 1490 to allocate a unique User ID number (UID) 799 to the User. As a final step in this process, block 906, the General Data Packet (GDP) 810 is constructed, comprising each set of the above detailed categories: Health Code (HC) 710, Health Level (HL) 720, Age Group (AG) 730, Gender Code (GC) 740 and User Unique ID Number (UID) 799.

Figure 10:
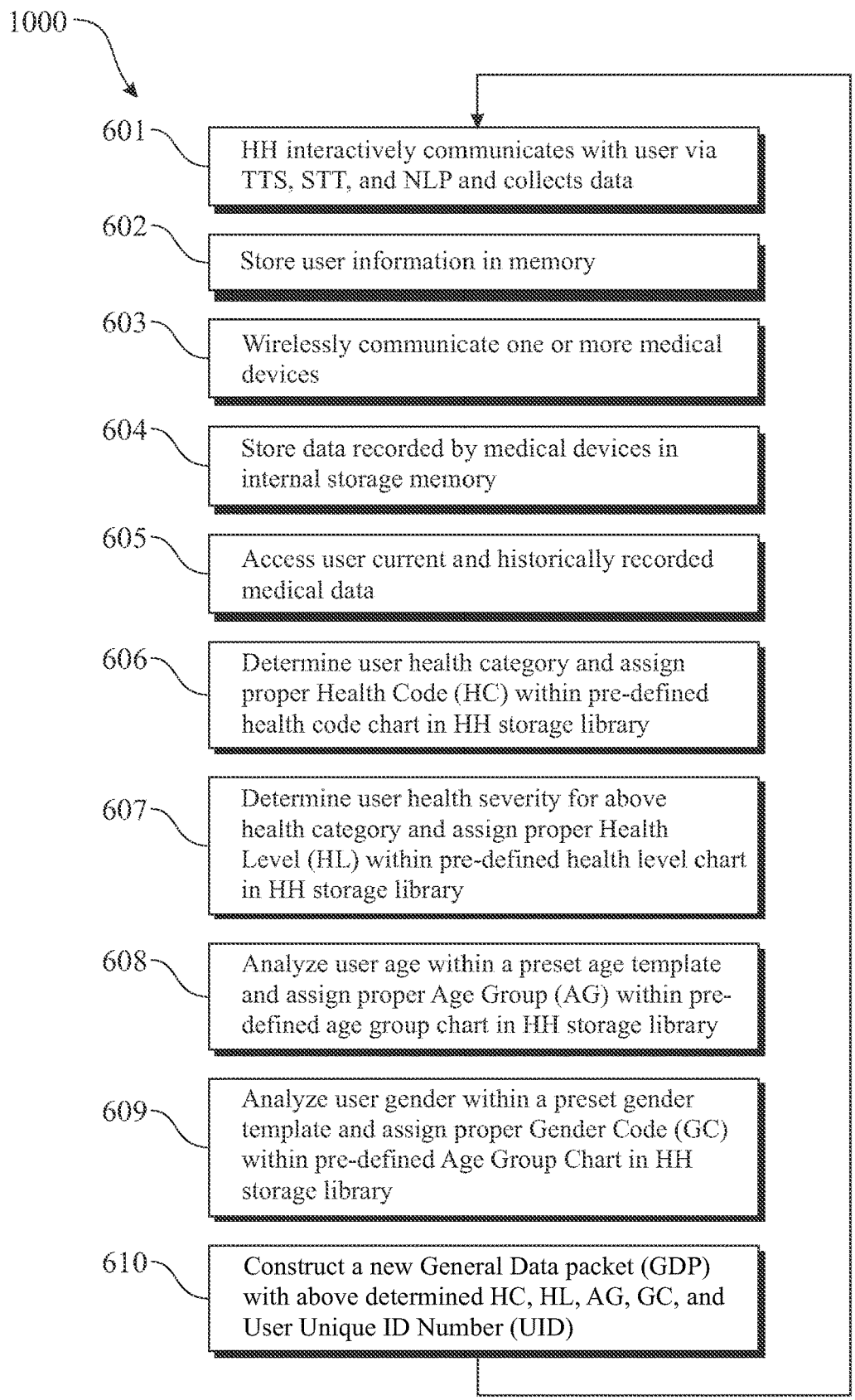
FIG. 10 presents an exemplary flow diagram for constructing a General Data Packet (GDP)

A flow diagram 1000 depicting an exemplary process for constructing the General Data Packet (GDP) 810 is presented in FIG. 10. The process 1000 starts with the autonomous Health Hub (HH) 100 interactively communicating with the user via Text To Speech (TTS) 64, Speech to Text (STT) 66 and Natural Language Processing (NLP) 68 and then collects the data (block 601). The user information is then stored in a memory 38 (block 602). The system then communicates to one or more medical devices 601, 602, 603, 604, 699 (block 603) and stores data recorded by medical devices in the internal storage memory 38 (block 604). The next step is accessing user account and historically recorded medical data (block 605). The user health category is then determined and assigned proper Health Code (HC) within the pre-defined health code chart in a storage library of the autonomous Health Hub (HH) 100 (block 606). The user health severity for the respective health category and assigned a proper Health Level (HL) within a predefined health level chart in the storage library of the autonomous Health Hub (HH) 100 (block 607). The age of the user is then analyzed within a pre-set age template and assigned a proper Age Group (AG) 740 within the predefined age group chart in the storage library of the autonomous Health Hub (HH) 100 (block 608). The user gender is then analyzed within a pre-set gender template and assigned proper Gender Code (GC) 750 within the predefined age group chart in the storage library of the autonomous Health Hub (HH) 100 (block 609). Finally, a new General Data Packet (GDP) 810 with the above determined Health Code (HC) 710, Health Level (HL) 720, Age Group (AG) 730, Gender Code (GC) 740 and User Unique ID Number (UID) 799 is generated (block 610).

Figure 11:
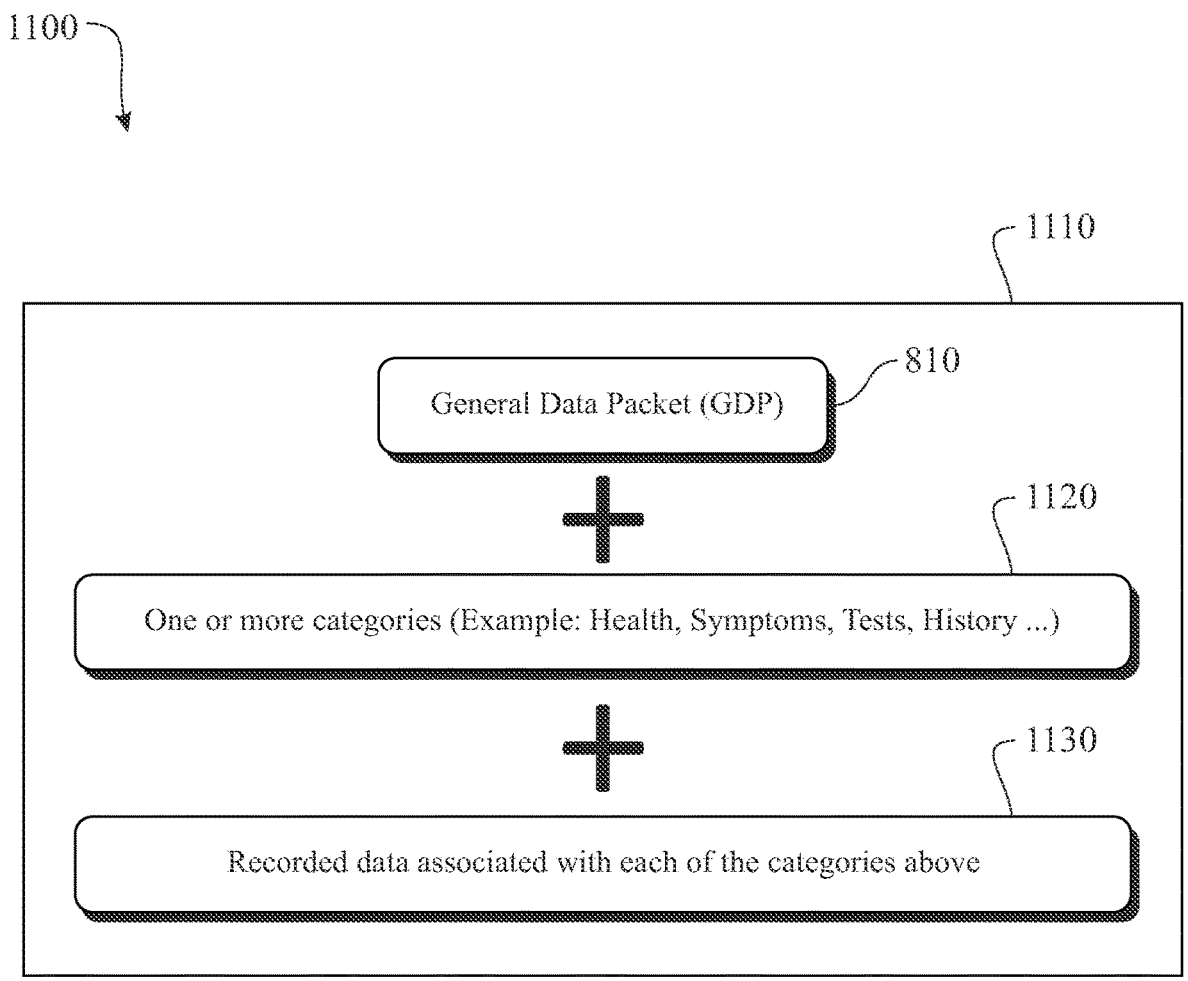
FIG. 11 presents an exemplary block diagram illustrating an arrangement of a Detail Data Packet (DDP)

A structure of a Detail Data Packet (DDP) 1110 is presented in block diagram detailing step 1100 illustrated in FIG. 11. The Detail Data Packet (DDP) 1110 includes a header containing a General Data Packet (GDP) 810. The Detail Data Packet (DDP) 1110 additionally includes one or more health related category items 1120. The category items 1120 of the Detail data Packet (DDP) 1110 include but are not limited to a health category, treatments, symptoms, test related information, and historical events. Each of the above category items 1120 additionally includes recorded data 1130 associated with each respective category. Examples of recoded data 1330 include Electrocardiograph (ECG) recordings, treatment logs, and medication history.

Figure 12:
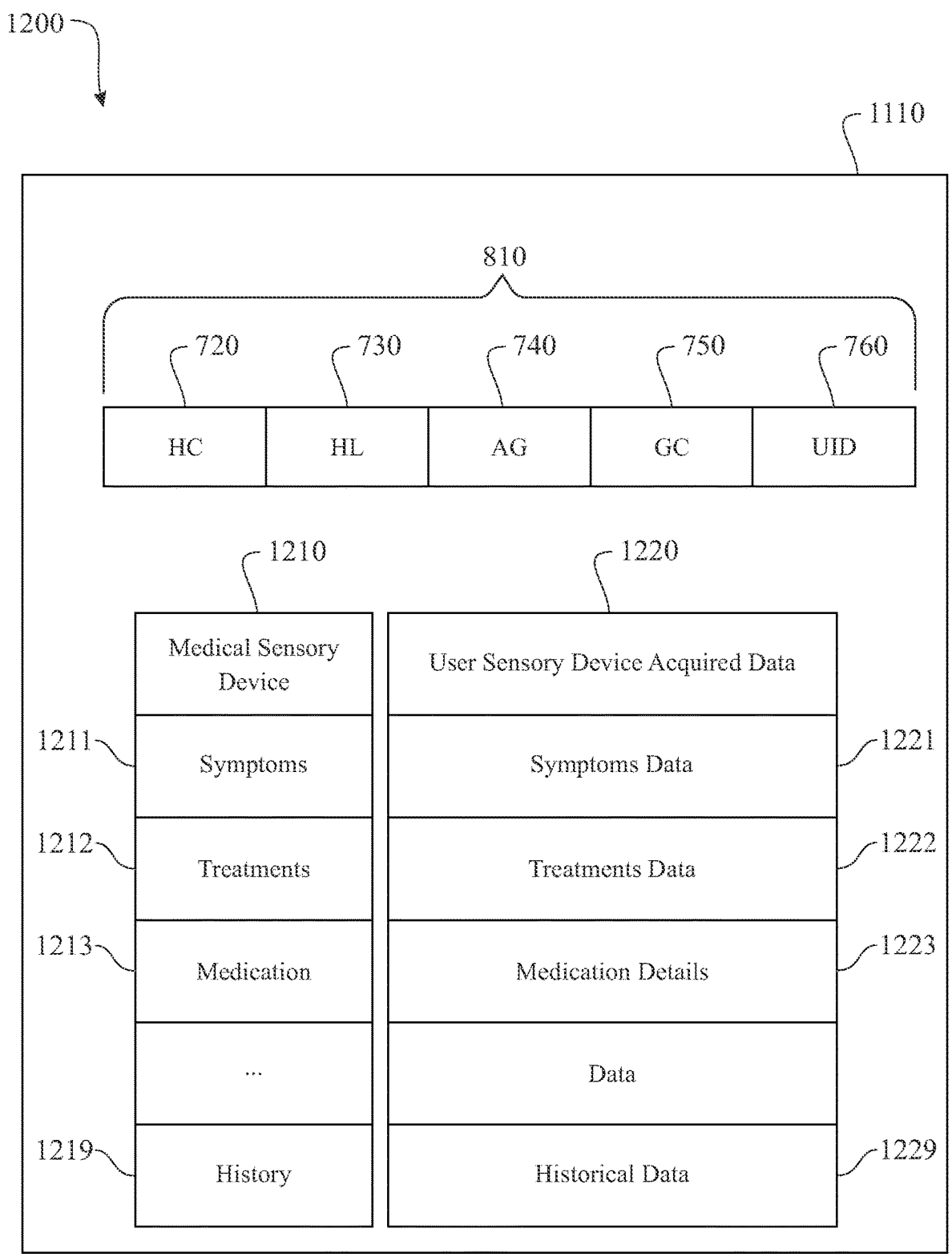
FIG. 12 presents an exemplary block diagram illustrating an arrangement of a Detail Data Packet (DDP)

An exemplary block diagram 1200 of the Detail Data Packet (DDP) 1110 is presented in FIG. 12. The Detail Data Packet (DDP) 1110 includes a header which contains the General Data Packet (GDP) 710. The General Data Packet (GDP) 710 includes one or more user related pieces of information. The User ID Number (UID) 760 is a unique identification number assigned to each Health Hub (HH) 100 by the Central Health Hub (CHH) 1490. The User ID Number (UID) 760 is used to uniquely identify each autonomous Health Hub (HH) 100 within the health hub network. In an example shown in FIG. 12, the General Data Packet (GDP) 710 includes: (a) the Health Code (HC) 720 which is assigned the highest priority level; (b) the Health Level (HL) 730 which is assigned the next lower priority level; (c) the Age Group (AG) 740 which is assigned the next lower Priority Level; and (d) the Gender Code (GC) 750 which is assigned the next lower priority level. The exemplary Detail Data Packet (DDP) 1110 further comprising a medical sensory device category 1210 and its acquired data 1220, a symptoms category 1211 and its acquired symptoms data 1221, a treatments category 1212 and its acquired treatments data 1222, a medication category 1213 and its acquired medication data 1223, and finally, a history category 1219 and its acquired historical data 1229.

Figure 13:
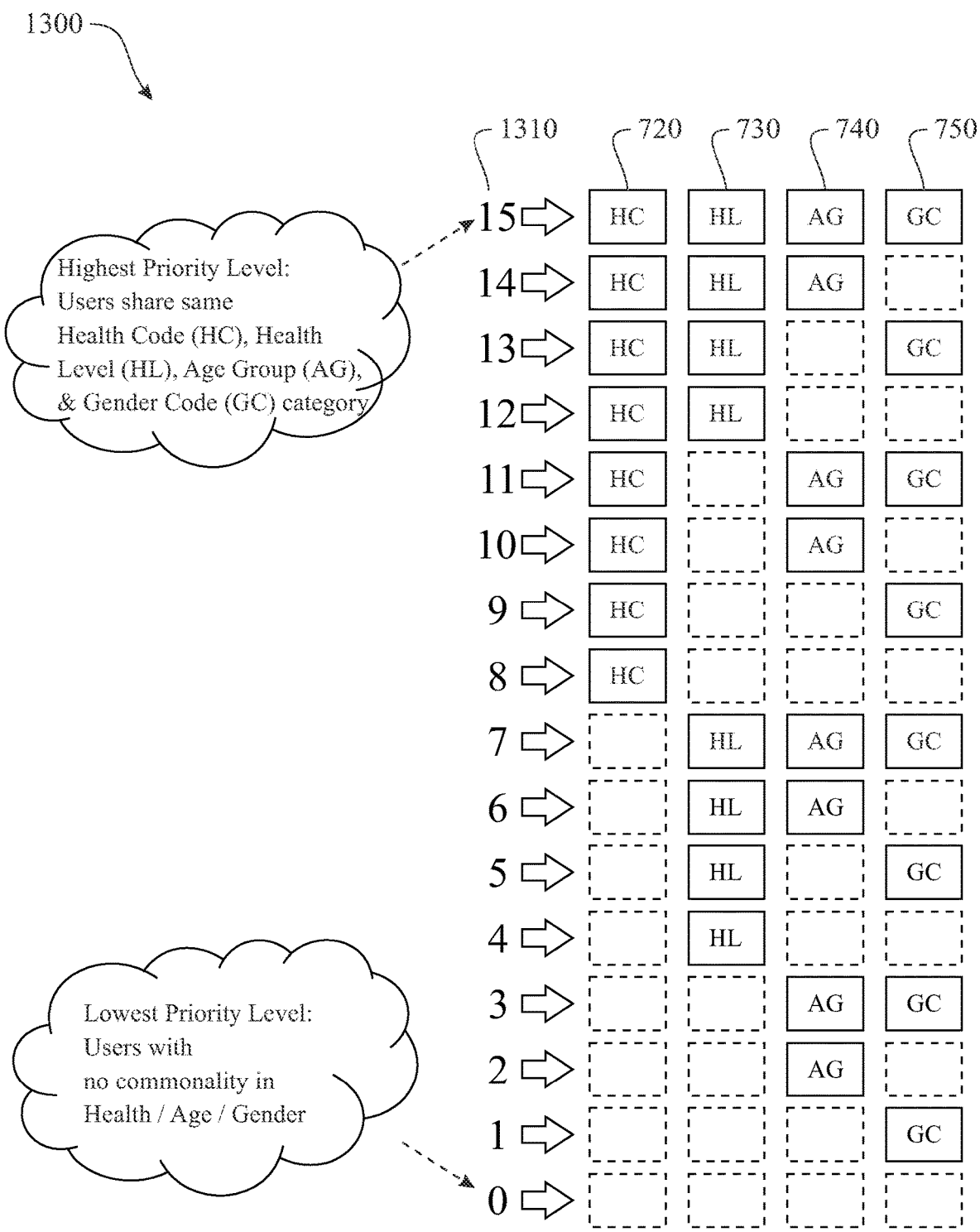
FIG. 13 presents an exemplary schematic diagram of a public group matching based on user General Data Packet (GDP) information, the user General Data Packet (GDP) comprising four (4) group categories.

A process of matching an autonomous Health Hub (HH) 100 to a public health group based on the User/Patient General Data Packet (GDP) 1110 is presented in a schematic diagram detailing step 1300 which is illustrated in FIG. 13. In the sample process shown, the General Data Packets (GDP's) 1110 consist of four (4) programmable (variable) components of: (a) the Health Code (HC) 720 which represents the user health category (such as diabetes, blood pressure, cardiovascular, and so on); (b) the Health Level (HL) 730 which represents the general category related to the severity of the user's health condition within the health category (in one example, a diabetes patient, the Health Level (HL) 730 can represent Diabetes Type-1 or Type-2); (c) the Age Group 740 which represents one or more general age categories of the user (examples of age categories could be in group ages, such as infants, 1 to 5 Years, 6 to 12 Years, 13 to 21 years, . . . 65 years and older); (d) the Gender Code 750 which represents the user's gender affiliation, and (e) in addition a unique User ID Number (UID) 760 which is a unique identification number assigned to each user by the Central Health Hub (CHH) 1490. The above listed components of General Data Packets (GDP) 1110 are utilized to establish a priority system for matching an autonomous Health Hub (HH) 100 of a user to at least one public health group as presented below. In the sample General Data Packet (GDP) 1110 shown in FIG. 13: (a) the Health Code (HC) 720 is assigned the highest priority level 1310, (b) the Health Level (HL) 730 is assigned the next lower priority level, (c) the Age Group (AG) 740 is assigned the next lower priority level 1310, and (d) the Gender Code (GC) 750 is assigned the next lower priority level 1310. A public health group containing current user hub members with similar (matching) all four (4) categories above with the General Data Packet (GDP) 1110 of the current autonomous Health Hub (HH) 100 will be assigned the highest match priority level 1310, which in this sample is 15. A public health group containing user hub members with no similar (matching) categories above with the General Data Packet (GDP) 1110 of the current autonomous Health Hub (HH) 100 will be assigned the lowest match priority level, which, in this sample, is 0. The formation (or demographic) of the entire scope of priority between the autonomous Health Hubs (HH's) 100 within all existing public health groups is demonstrated in FIG. 7.

Figure 14:
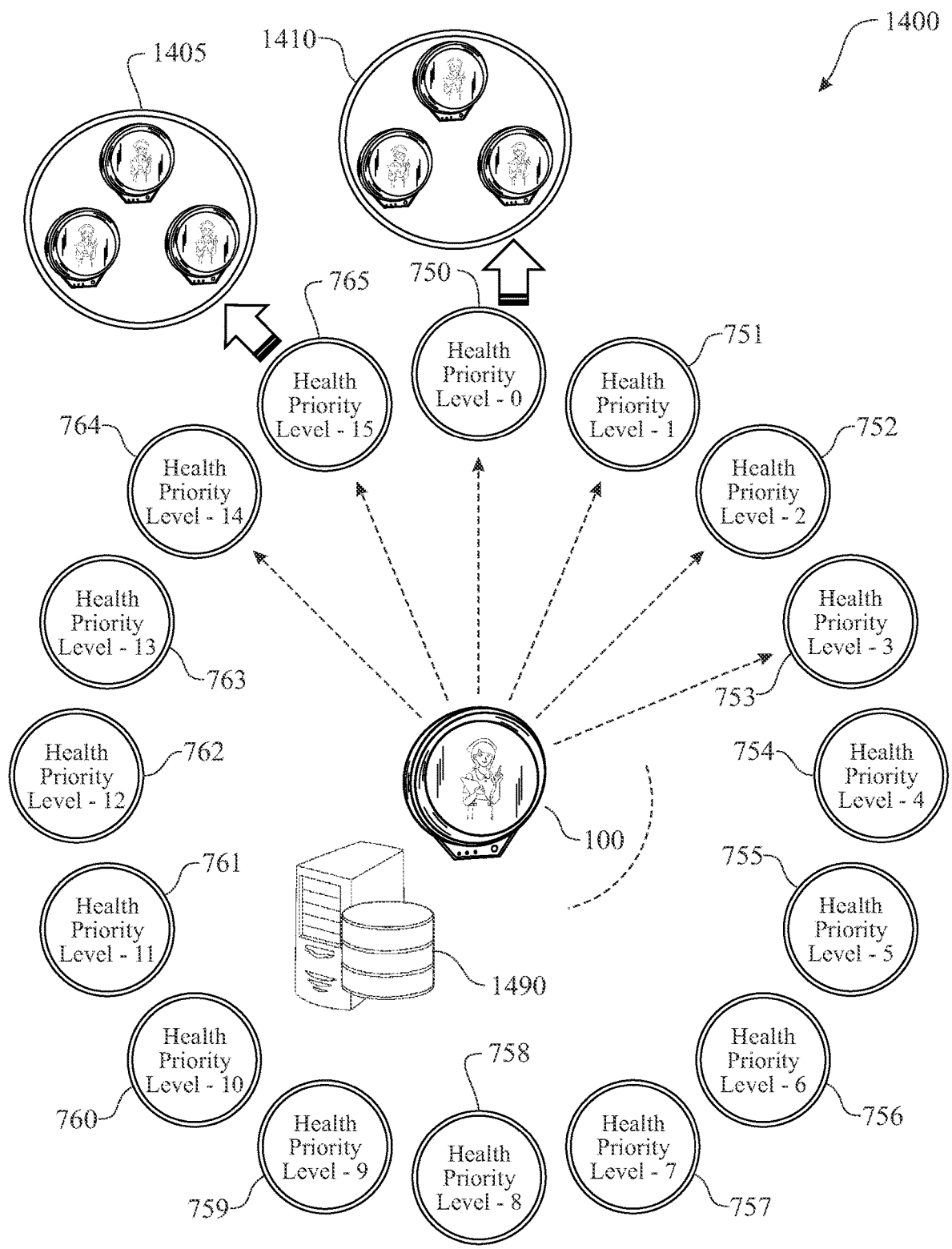
FIG. 14 presents an exemplary schematic diagram of a Public Health Group (PHG) with Health Priority Levels (HPL's) of 0 to 15.

An entire spectrum of public health groups within the health hub network, based on their Health Priority Level (HPL) 1310 for the current autonomous Health Hub (HH) 100 is presented in a schematic diagram representing step 1400, which is illustrated in FIG. 14. The exemplary entire spectrum (represented in schematic form 1400) of public health groups within the health hub network includes sixteen (16) Health Priority Levels (HPL's) (numbered 0 through 15 maintaining consistency with the exemplary case illustrated in FIG. 13). The autonomous Health Hub (HH) 100 communicates with the Central Health Hub (CHH) 1490 to obtain links for various public health groups within the health hub network. In the example shown, the exemplary autonomous Health Hub (HH) 750 is assigned a lowest Health Priority Level (HPL) 1310 of zero (0), which indicates that none of the autonomous Health Hubs (HH's) 100 within this exemplary Public Health Group (PHG) 1410 has any common General Data Packet category codes with the requesting autonomous Health Hub (HH) 100. At the other end of the spectrum, a Public Health Group (PHG) 1405 however is assigned a highest Health Priority Level (HPL) 1310 of fifteen (15), which indicates that the autonomous Health Hubs (HH's) 100 within this Public Health Group (PHG) 1405 have similar common General Data Packet category codes of Health Codes (HC) 720, Health Level (HL) 730, Age Group (AG) 740 and Gender Code (GC) 750.

Figure 15:
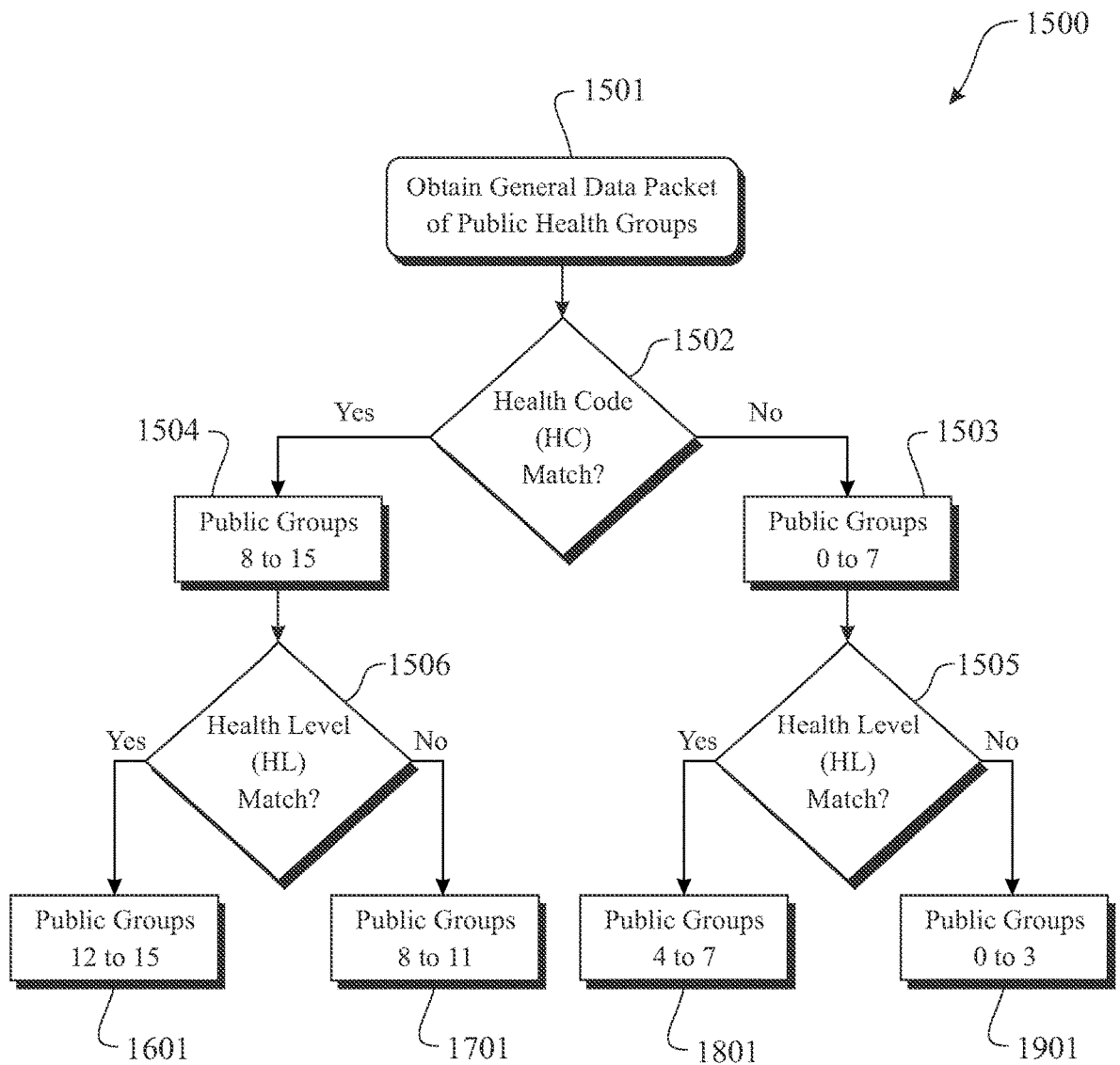
FIG. 15 presents an exemplary flow diagram representing a first level public group selection based on user General Data Packet (GDP), the user General Data Packet (GDP) comprising information associated with four (4) group categories.

A series of exemplary flow diagrams 1500, 1600, 1700, 1800, 1900 present steps to determine priority level matches between the user Health Hub General Data Packet (GCP) and those of other autonomous Health Hubs (HH's) 100 within the Public Health Group (PHG) are presented in FIGS. 15 through 19. In FIG. 15, the process 1500 initiates with a step to access/obtain the General Data Packet (GDP) of All Public Health groups (step 1501). Check to see if the Health Code (HC) of the Public Health Group (PHG) matches the Health Code (HC) of the current autonomous Health Hub (HH) 100 (step 1502). If the Health Code (HC) of the Public Health Group (PHG) does not match the Health Code (HC) of the current autonomous Health Hub (HH) 100 (step 1502), the process assigns a public group priority range of 0 to 7 to the above Public Health Group (PHG) (step 1503) and proceed to step 1505. If the Health Code (HC) of the Public Health Group (PHG) matches the Health Code (HC) of the current autonomous Health Hub (HH) 100 (step 1502), the process assigns a public group priority range of 8 to 15 to the above Public Health Group (PHG) (step 1504) and proceeds to step 1506. Decision step 1505 determines if the Health Level (HL) of the Public Health Group (PHG) matches the Health Level (HL) of the current Health Hub (HH) 100. If the Health Level (HL) of the Public Health Group (PHG) does not match the Health Level (HL) of the current Health Hub (HH) 100 (step 1502), the process assigns a public group priority range of 0 to 3 to the above Public Health Group (PHG) (step 1901). If the Health Level (HL) of the Public Health Group (PHG) matches the Health Level (HL) of the current Health Hub (HH) 100 (step 1505), the process assigns a public group priority range of 4 to 7 to the above Public Health Group (PHG) (step 1801). Decision step 1506 determines if the Health Level (HL) of the Public Health Group (PHG) matches the Health Level (HL) of the current Health Hub (HH) 100. If the Health Level (HL) of the Public Health Group (PHG) does not match the Health Level (HL) of the current autonomous Health Hub (HH) 100 (step 1506), the process assigns a public group priority range of 8 to 11 to the above Public Health Group (PHG) (step 1701). If the Health Code (HC) of the of the Public Health Group (PHG) matches the Health Level (HL) of the current autonomous Health Hub (HH) 100 (step 1506), the process assigns a public group priority range of 12 to 15 to the above Public Health Group (PHG) (step 1601).

Figure 16:
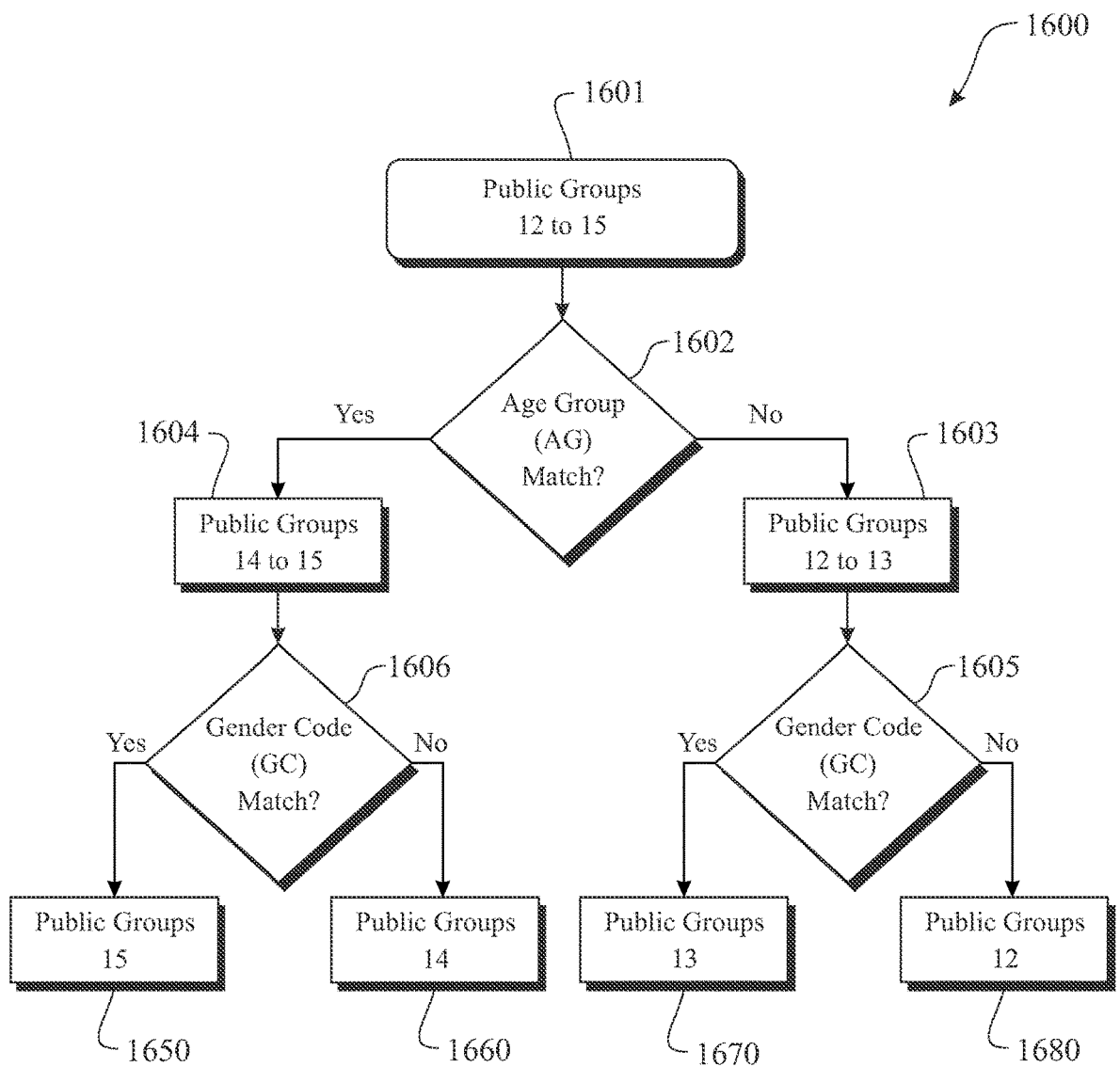
FIG. 16 presents an exemplary flow diagram representing a second level public group selection based on user General Data Packet (GDP), the user General Data Packet (GDP) comprising information associated with four (4) group categories.

The process 1600 accesses/obtains a General Data Packet (GDP) of Public Health Groups (PHG) assigned priority level 12 to 15 (step 1601) as presented in FIG. 16. Decision step 1602 determines if the Age Group (AG) of the Public Health Group (PHG) matches the Age Group (AG) of the current autonomous Health Hub 100. If the Age Group (QG) of the Public Health Group (PHG) does not match the Age Group (AG) of the current autonomous Health Hub 100 (decision step 1602), the process assigns a public group priority range of 12 to 13 to the above Public Health Group (PHG)(step 1603) and proceeds to step 1605. If the Age Group (AG) of the Public Health Group (PHG) matches the Age Group (AG) of the current autonomous Health Hub 100 (decision step 1602), the process assigns a public group priority range of 14 to 15 to the above Public Health Group (PHG) (step 1604) and proceeds to step 1606. At step 1605, the process checks to see if the Gender Code (GC) of the Public Health Group (PHG) matches the Gender Code (GC) of the current autonomous Health Hub (HH) 100. If Gender Code (GC) of the Public Health Group (PHG) does not match the Gender Code (GC) of the current autonomous Health Hub (HH) 100, the process assigns a public group priority of 12 to the above Public Health group 1603 1680. If the Gender Code (GC) matches, the process assigns a public group priority of 13 to the above Public Health Group (PHG) 1603 (step 1670). Decision step 1606 checks to see if the Gender Code (GC) of the Public Health Group (PHG) matches the Gender Code (GC) of the current autonomous Health Hub (HH) 100. If the Gender Code (GC) of the Public Health Group (PHG) does not match the Gender Code (GC) of the current autonomous Health Hub (HH) 100, the process assigns a public group priority of 14 to the above Public Health Group (PHG) 1604 (step 1660). If the Gender Code (GC) of the Public Health Group (PHG) matches the Gender Code (GC) of the current autonomous Health Hub (HH) 100, the process assigns a public group priority of 15 to the above Public Health Group (PHG) 1604 (step 1650).

Figure 17:
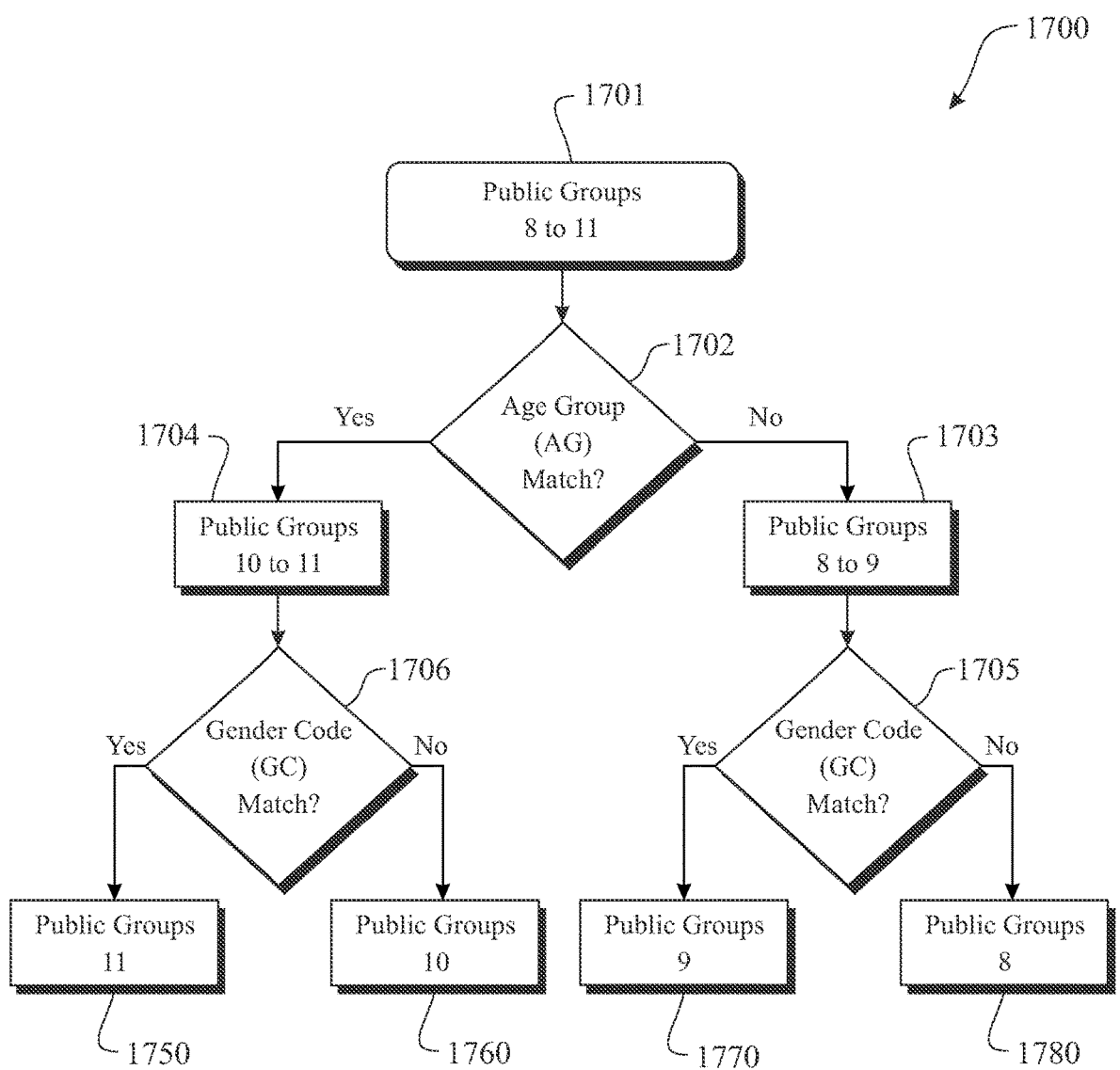
FIG. 17 presents an exemplary flow diagram representing a third level public group selection based on user General Data Packet (GDP), the user General Data Packet (GDP) comprising information associated with four (4) group categories.

The process 1700 accesses/obtains a General Data Packet (GDP) 1701 of Public Health Groups (PHG) assigned a priority level 8 to 11 (step 1701) as presented in FIG. 17. Decision step 1702 determines if the Age Group (AG) of the Public Health Group (PHG) matches the Age Group (AG) of the current autonomous Health Hub (HH) 100. If the Age Group (AG) of the Public Health Group (PHG) 1701 does not match the Age Group (AG) of the current autonomous Health Hub (HH) 100, the process assigns a public group priority a range of 8 to 9 to the above Public Health Group (PHG) 1701 (step 1703) and proceeds to step 1705. If the Age Group (AG) of the Public Health Group (PHG) 1701 matches the Age Group (AG) of the current autonomous Health Hub (HH) 100, the process assigns a public group priority a range of 10 to 11 to the above Public Health Group (PHG) 1701 (step 1704) and proceeds to step 1706. Decision step 1705 determines if the Gender Code (GC) of the Public Health Group (PHG) 1703 matches the Gender Code (GC) of the current autonomous Health Hub (HH) 100. If the Gender Code (GC) of the Public Health Group (PHG) 1703 does not match the Gender Code (GC) of the current autonomous Health Hub (HH) 100, the process assigns a public group priority of 8 to the above Public Health Group 1703 (step 1780). If the Gender Code (GC) of the Public Health Group 1703 matches the Gender Code (GC) of the current autonomous Health Hub (HH) 100, the process assigns a public group priority of 9 to the above Public Health Group (PHG) 1703 (step 1770). Decision step 1706 determines if the Gender Code (GC) of the Public Health Group (PHG) 1704 matches the Gender Code (GC) of the current autonomous Health Hub (HH) 100. If the Gender Code (GC) of the Public Health Group (PHG) 1704 does not match the Gender Code (GC) of the current autonomous Health Hub (HH) 100, the process assigns a public g priority of 10 to the above Public Health Group 1704 (step 1760). Whereas, if the Gender Code (GC) of the Public Health Group (PHG) 1704 matches the Gender Code (GC) of the current autonomous Health Hub (HH) 100, the process assigns a public group priority of 11 to the above Public Health Group (PHG) 1704 (step 1750).

Figure 18:
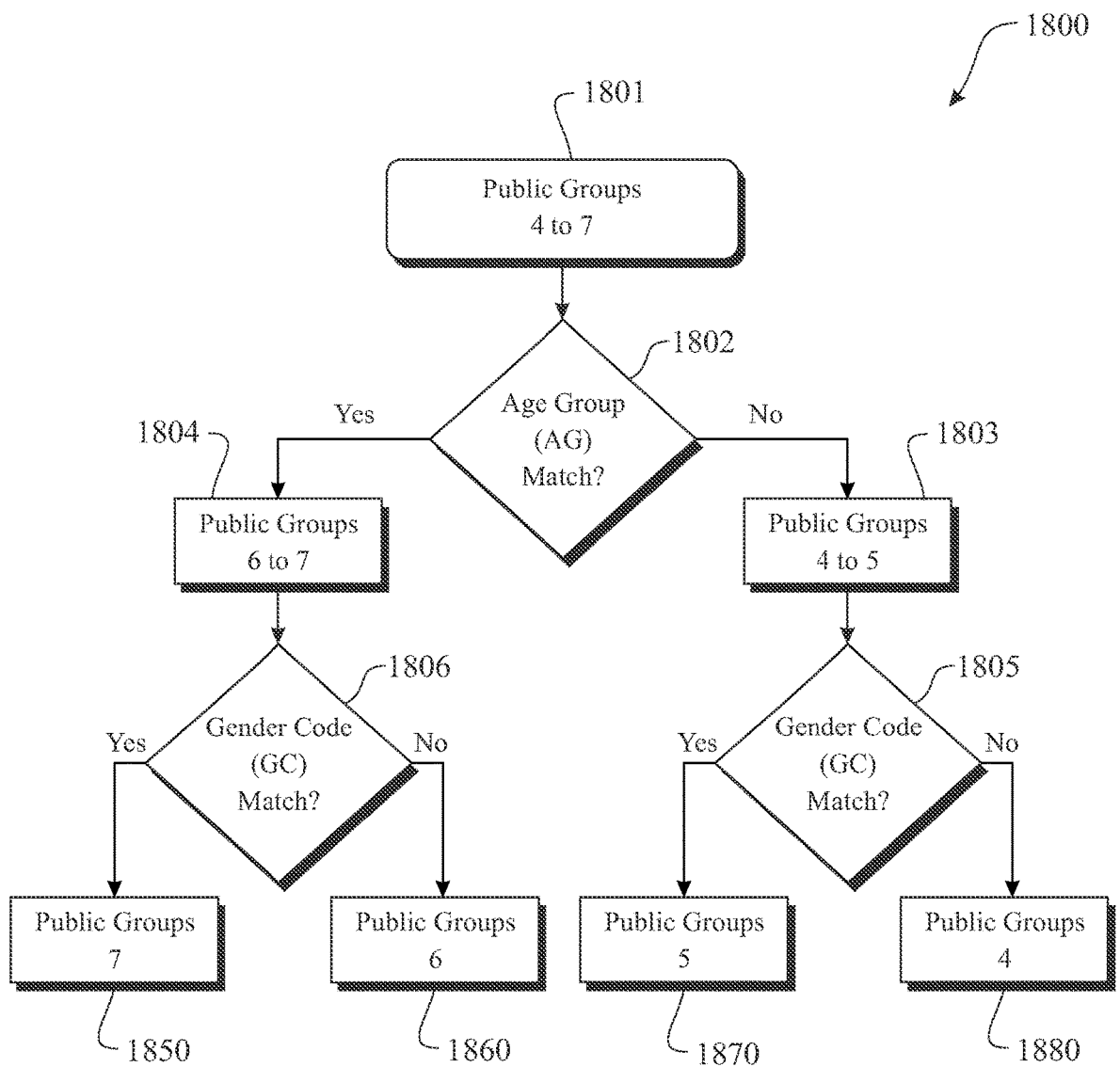
FIG. 18 presents an exemplary flow diagram representing a fourth level public group selection based on user General Data Packet (GDP) information associated with four (4) group categories.
Figure 19:
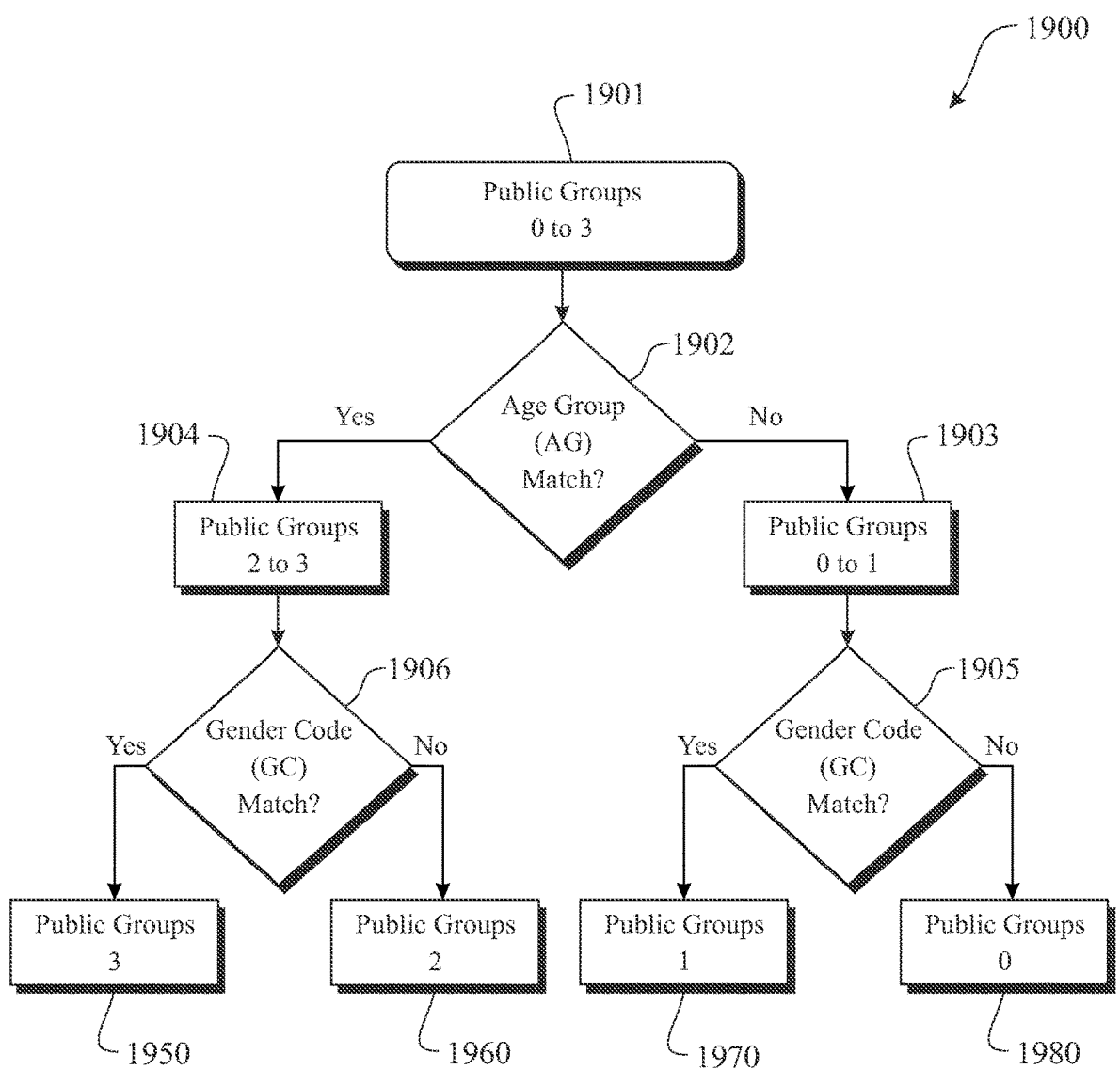
FIG. 19 presents an exemplary flow diagram representing a fifth level public group selection based on the user General Data Packet (GDP), the user General Data Packet (GDP) comprising information associated with four (4) group categories.

The process 1800 accesses/obtains a General Data Packet (GDP) of Public Health Groups (PHG) 1801 assigned a priority level 4 to 7 as presented in FIG. 18. Decision step 1802 determines if the Age Group (AG) of the Public Health Group (PHG) 1801 matches the Age Group (AG) of the current autonomous Health Hub (HH) 100. If the Age Group (AG) of the Public Health Group (PHG) 1801 does not match the ###, the process assigns a public group priority a range of 4 to 5 to the above Public Health Group (PHG) 1801 (step 1803) and proceeds to step 1805. If the Age Group (AG) of the Public Health Group (PHG) 1801 matches the Age Group (AG) of the current autonomous Health Hub (HH) 100, the process assigns a public group priority a range of 6 to 7 to the above Public Health Group (PHG) 1801 (step 1804) and proceeds to decision step 1806. Decision step 1805, determines if the Gender Code (GC) of the Public Health Group (PHG) 1803 matches the Gender Code (GC) of the current autonomous Health Hub (HH) 100. If the Gender Code (GC) of the Public Health Group (PHG) 1803 does not match the Gender Code (GC) of the current autonomous Health Hub (HH) 100, the process assigns a public group priority of 4 to the above Public Health Group 1803 (step 1880). If the Gender Code (GC) of the Public Health Group (PHG) 1803 matches the Gender Code (GC) of the current autonomous Health Hub (HH) 100, the process assigns a public group priority of 5 to the above Public Health Group (PHG) 1803 (step 1870). Decision step 1806 determines if the Gender Code (GC) of the Public Health Group (PHG) 1804 matches the Gender Code (GC) of the current autonomous Health Hub (HH) 100. If the Gender Code (GC) of the Public Health Group (PHG) 1804 does not match the Gender Code (GC) of the current autonomous Health Hub (HH) 100, the process assigns a public group priority of 6 to the above Public Health Group (PHG) 1804 (step 1860). If the Gender Code (GC) of the Public Health Group (PHG) 1804 matches the Gender Code (GC) of the current autonomous Health Hub (HH) 100, the process assigns a public group priority of 7 to the above Public Health Group (PHG) 1804 (step 1850).

The process 1900 accesses/obtains a General Data Packet (GDP) of the Public Health Groups (PHG) 1901 assigned a priority level 0 to 3. Decision step 1902 determines if the Age Group (AG) of the Public Health Group (PHG) 1901 matches the Age Group (AG) of the current autonomous Health Hub (HH) 100. If the Age Group (AG) of the Public Health Group (PHG) 1901 does not match the Age Group (AG) of the current autonomous Health Hub (HH) 100, the process assigns a public group priority range of 0 to 1 to the above Public Health Group (PHG) (step 1903) and proceeds to decision step 1905. If the Age Group (AG) of the Public Health Group (PHG) 1901 matches the Age Group (AG) of the current autonomous Health Hub (HH) 100, the process assigns a public group priority range of 2 to 3 to the above Public Health Group 1901 (step 1902) and proceeds to decision step 1906. Decision step 1905 determines if the Gender Code (GC) of the Public Health Group (PHG) 1901 matches the Gender Code (GC) of the current autonomous Health Hub (HH) 100. If the Gender Code (GC) of the Public Health Group (PHG) 1901 does not match the Gender Code (GC) of the current autonomous Health Hub (HH) 100, the process assigns a public group priority of 0 to the above Public Health Group 1903 (step 1980). If the Gender Code (GC) of the Public Health Group (PHG) 1901 matches the Gender Code (GC) of the current autonomous Health Hub (HH) 100, the process assigns a public group priority of 1 to the above Public Health Group (PHG) 1903 (step 1970). Decision step 1906 determines if the Gender Code (GC) of the Public Health Group (PHG) 1902 matches the Gender Code (GC) of the current autonomous Health Hub (HH) 100. If the Gender Code (GC) of the Public Health Group (PHG) 1902 does not match the Gender Code (GC) of the current autonomous Health Hub (HH) 100, assign public group priority of 2 to the above Public Health group 1960. If the Gender Code (GC) of the Public Health Group (PHG) 1902 matches the Gender Code (GC) of the current autonomous Health Hub (HH) 100, the process assigns a public group priority of 3 to the above Public Health Group (PHG) 1902 (step 1950).

Figure 20:
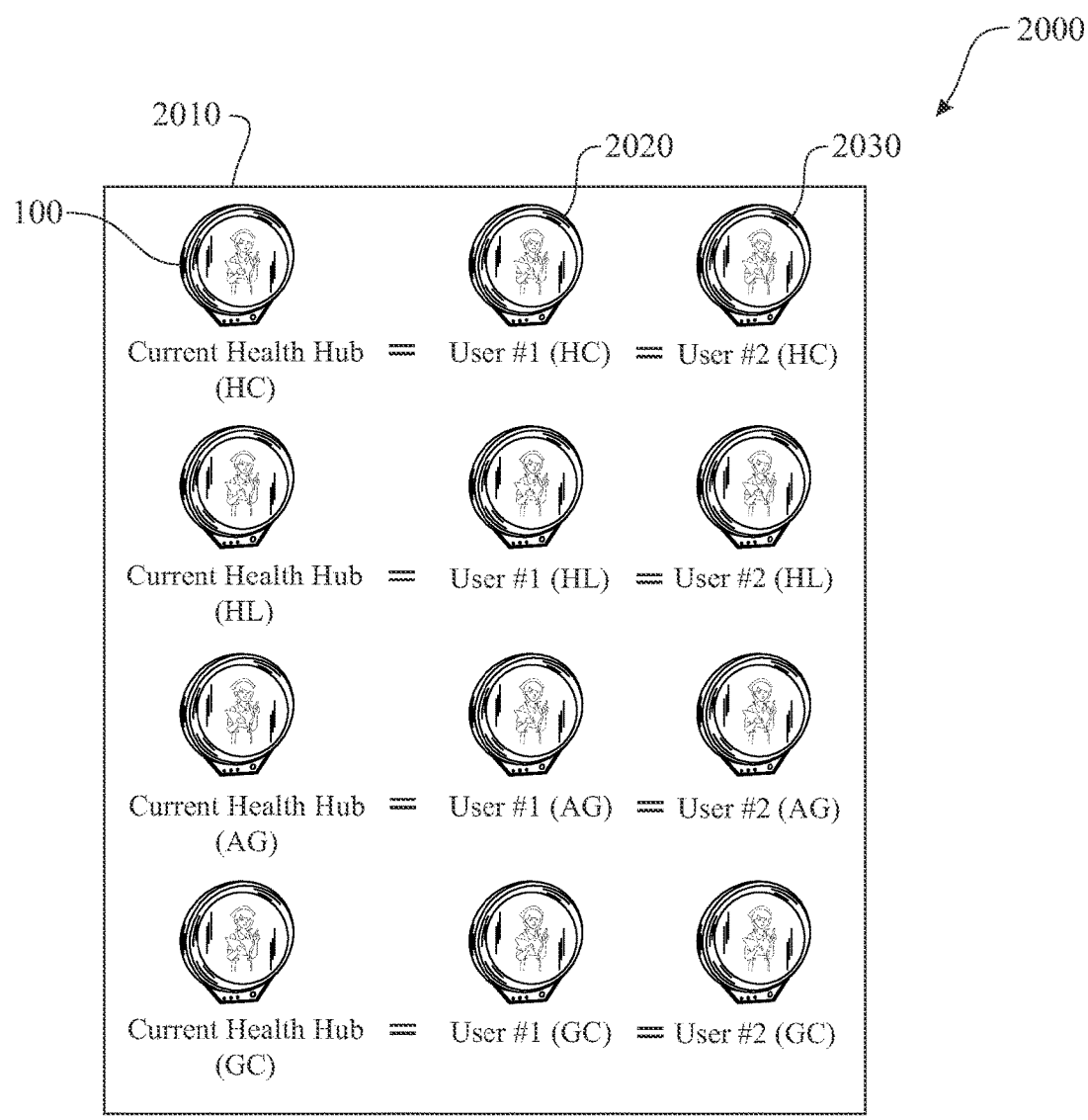
FIG. 20 presents an exemplary schematic diagram introducing Public Group #1, wherein Public Group #1 has a Highest Priority match level with a current Health Hub (HH) originally introduced in FIG. 1.
Figure 20:
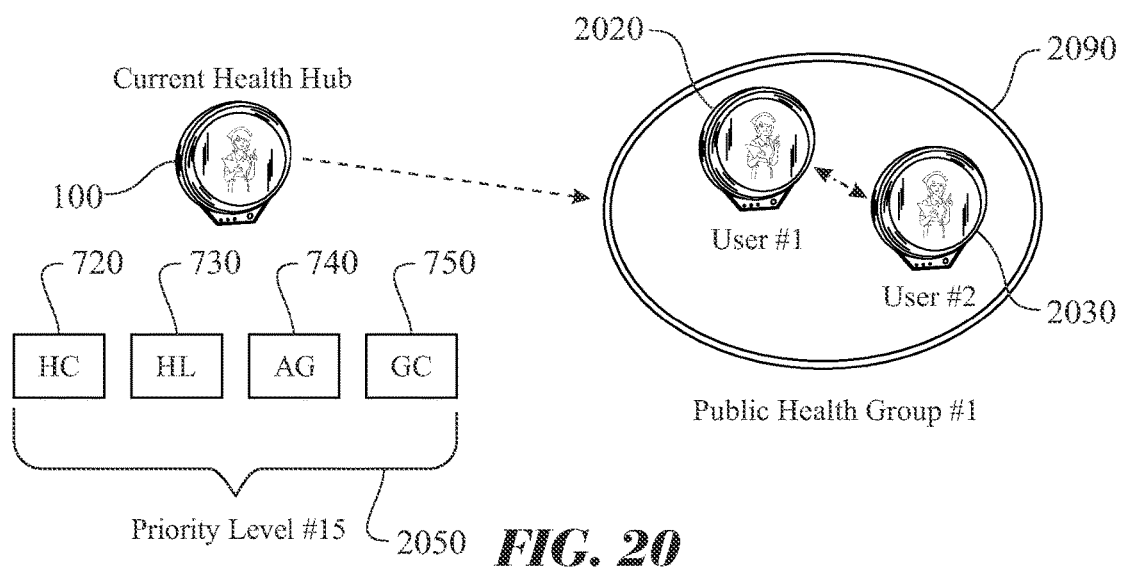

An exemplary configuration of a Public Health group #1 2090 having been assigned a highest matching priority level for the current Health Hub 2000 is presented in FIG. 20. A network 2010 includes a current Health Hub (HH) 100 and members of public health group #1 2090, all having like values in the user selected categories 2050. The current Health Hub (HH) 100 includes a Health Code (HC) 720, a Health Level (HL) 730, an Age Group (AG) 740 and a Gender Code (GC) 750, collectively defining a series of user related categories 2050. In the exemplary public group, both a user #1 and a user #2 share matching categories 1300, including a matching Health Code (HC) 720, a matching Health Level (HL) 730, a matching Age Group (AG) 740 and a matching Gender Code (GC) 750 as the Current autonomous Health Hub (HH) 100. The exemplary Group 2090 includes two member Health Hubs (100), user #1 health hub (HH) 2020 and user #2 health hub (HH) 2030. The highest priority level 15 2050 is assigned to the public group #1 2090 based on the public group matching categories 1300 shown in FIG. 13.

Figure 21:
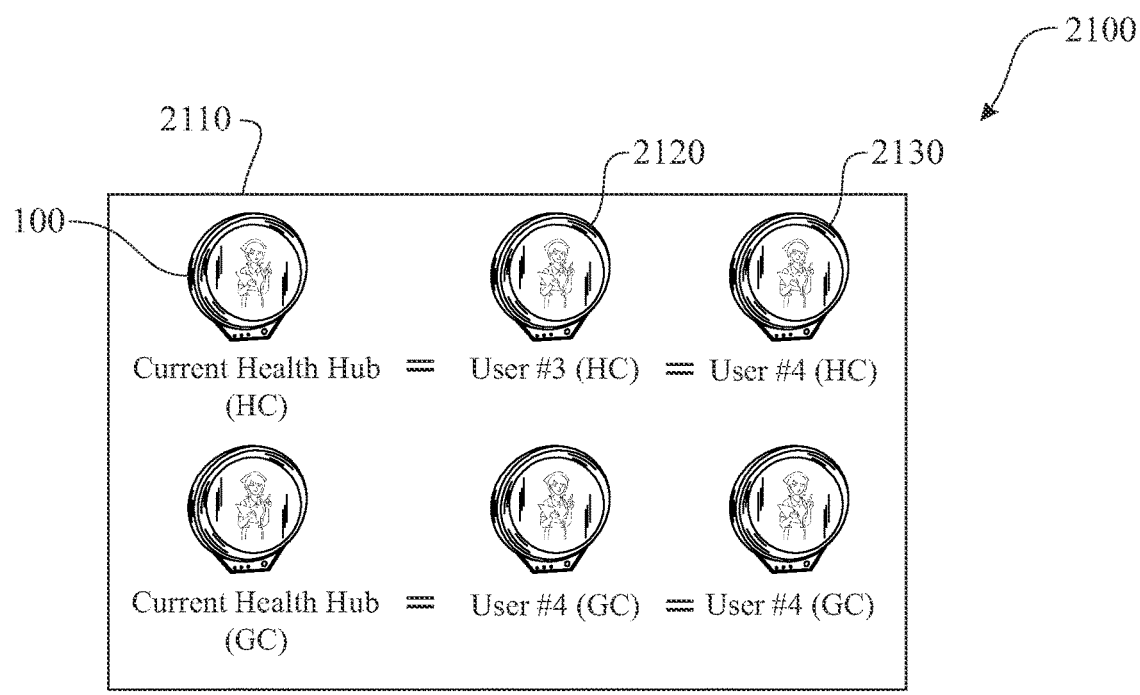
FIG. 21 presents an exemplary schematic diagram introducing Public Group #2, wherein Public Group #2 is provided for users having matching Health Codes (HC's) and Gender Codes (GC's) with the current Health Hub (HH) originally introduced in FIG. 1; (#### Does the health codes match one another or health codes on the HH? ##)
Figure 21:
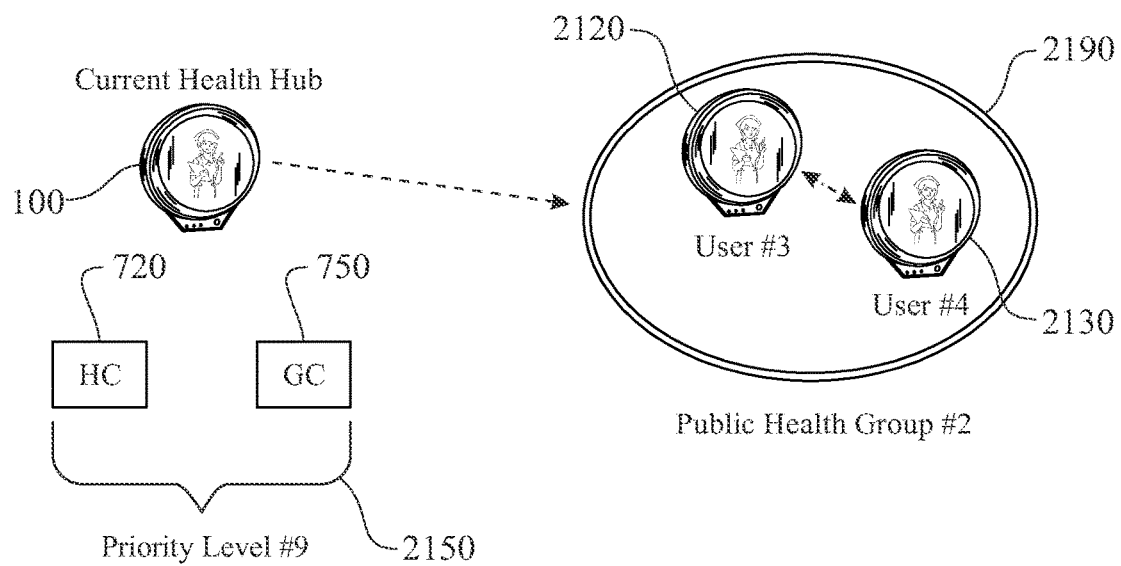
Figure 22:
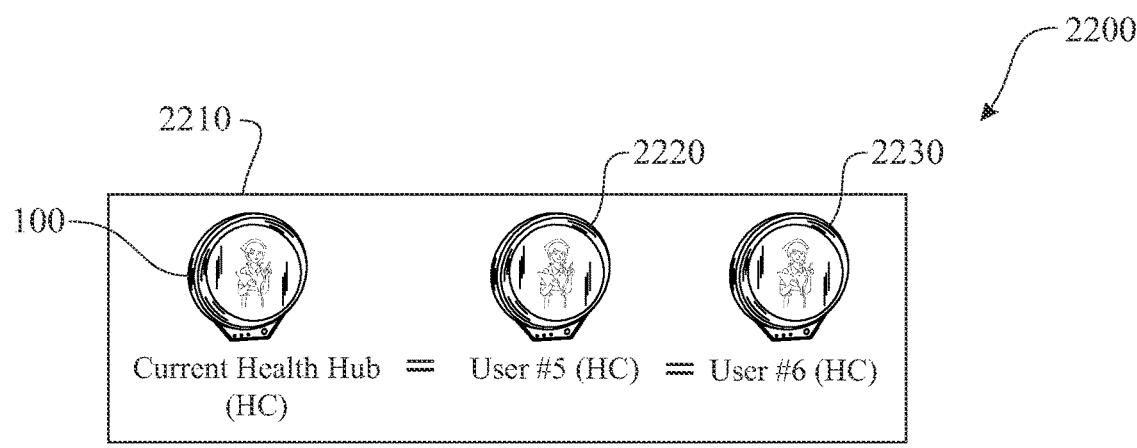
FIG. 22 presents an exemplary schematic diagram introducing Public Group #3 for users having matching Health Codes (HC's) with the current Health Hub (HH) originally introduced in FIG. 1; (#### Does the health codes match one another or health codes on the HH?##)
Figure 22:
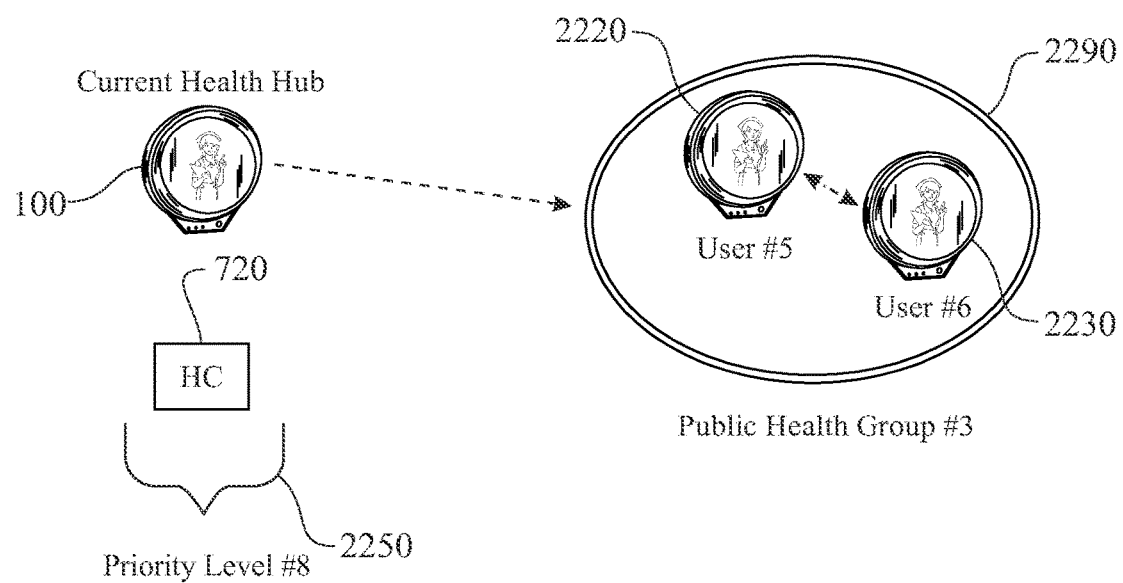

An exemplary configuration 2100 of a Public Health Group (PHG) #2 2190 for users having a Health Code (HC) 720 and a Gender Code (GC) 750 matching the Health Code (HC) 720 and the Gender Code (GC) 750 of the current autonomous Health Hub (HH) 100 is presented in FIG. 21. A network 2110 includes a current Health Hub (HH) 100 and members of public health group #2 2190, all having like values in the user selected categories 2150. The exemplary public group #2 2190 comprising two member Health Hubs (HH's), a third user Health Hub (HH) 2120 being associated with user #3 and the fourth user Health Hub (HH) 2130 being associated with user #4. Both user #3 and user #4 share a matching Health Code (HC) 720 and a matching Gender Code (GC) 750 as the current autonomous Health Hub (HH) 100. A priority level of 9 2150 is assigned to the Public Health Group (PHG) #2 2190 based on the public group matching categories 1300 shown in FIG. 13.

An exemplary configuration 2200 of a Public Health Group (PHG) #3 2290 for users having a matching Health Code (HC) with a current Health Hub (HH) 100. A network 2210 includes a current Health Hub (HH) 100 and members of public health group #3 2290, all having like values in the user selected categories 2050. The exemplary Public Health Group 2290 comprising two member Health Hubs (HH's), a fifth user Health Hub (HH) 2220 being associated with user #5 and a sixth user Health Hub (HH) 2230 being associated with user #6. Both user #5 and user #6 share a matching Health Code (HC) 720 as the current Health Hub (HH) 100. A priority level of 8 2250 is assigned to the Public Health Group (PHG) #3 2290 based on the public group matching categories 1300 shown in FIG. 13.

Figure 23:
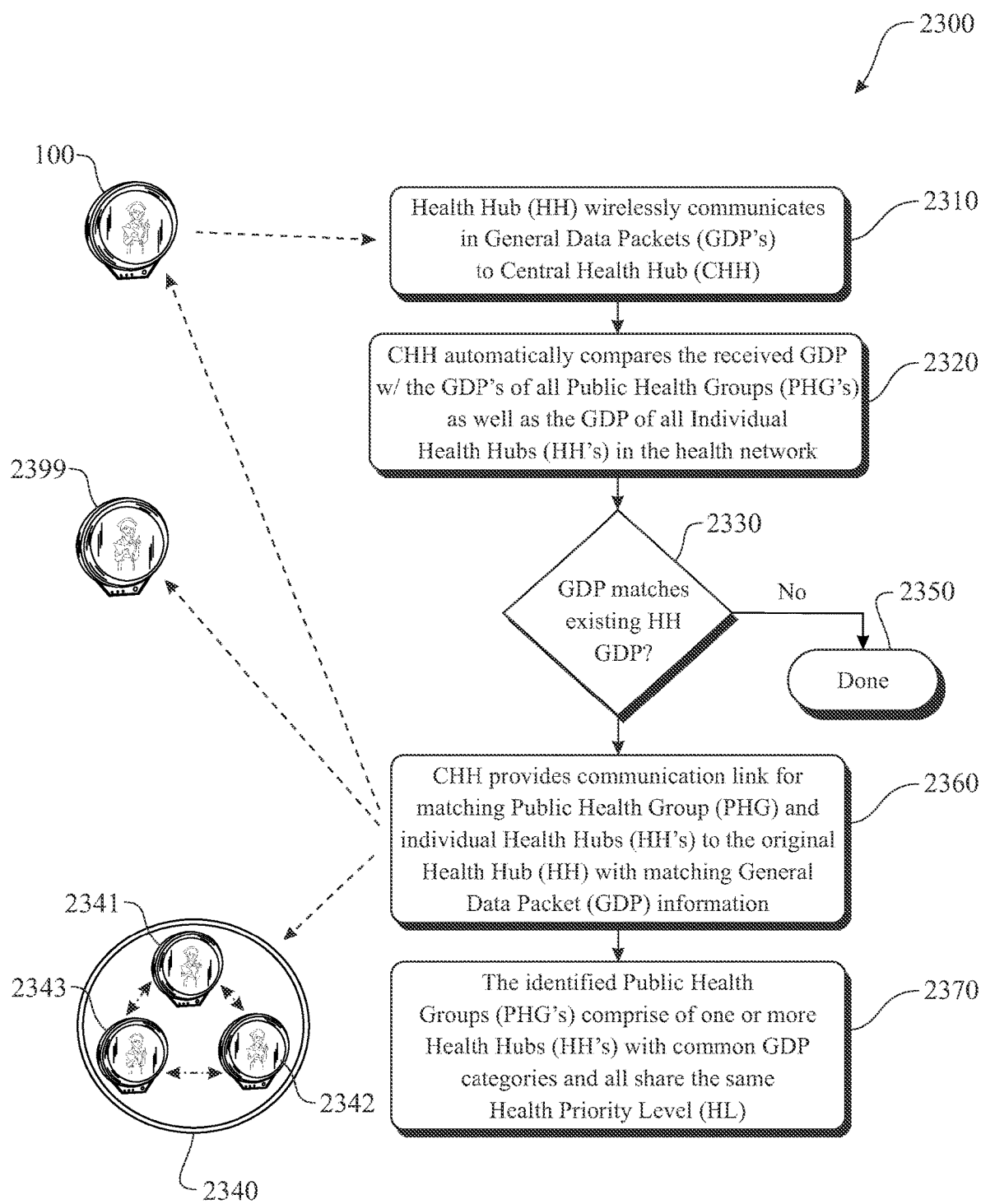
FIG. 23 presents an exemplary flow diagram for identifying matching Public Health Groups.

A flow diagram 2300 describing a process for identify matching Public Health Groups is presented in FIG. 23. The autonomous Health Hub (HH) 100 wirelessly communicates the General Data Packet (GDP) 810 associated therewith to the Central Health Hub (CHH) 1490 (step 2310). The Central Health Hub (CHH) 1490 then analyzes the received General Data Packet (GDP) (step 2320) and compares it to the General Data Packet (GDP) of all Public Health Groups as well as the General Data Packet (GDP) of all individual Health Hubs (HH's) in the Health Network to determine if any of the General Data Packets (GDP's) associated with each of the individual Health Hubs (HH's) matches the General Data Packet (GDP) 810 associated with the autonomous Health Hub (HH) 100 (decision step 2330). If no matching General Data Packets (GDP's) are found, then the matching process is complete (step 2350). An exemplary Public Health Group (PHG) 2340 includes three user's Health Hubs (HH) 2341, 2342, 2343; each having a matching or common General Data Packet (GDP). The exemplary Public Health Group (PHG) 2340 is characterized by the common General Data Packet (GDP). In the event that a General Data Packet (GDP) associated with the Public Health Group (PHG) 2340 or a General Data Packet (GDP) associated with any individual Health Hubs 2399 with matching General Data Packets (GDPs) are identified, then the Central Health Hub (CHH) 1490 communicates the link for the identified Public Health Group (PHG) 2340 and each of the matching individual Health Hubs (HH's) 2399 to the original autonomous Health Hub (HH) 100 (step 2360). This enables the individual Health Hubs 2399 having a General Data Packet (GDP) comprising like categories and sharing the sale health priority level to join the existing Public Health Group (PHG) 2340 or to form a new Public Health Group (PHG), which would include each matching individual Health Hub (HH) 2399 (step 2370).

Figure 24:
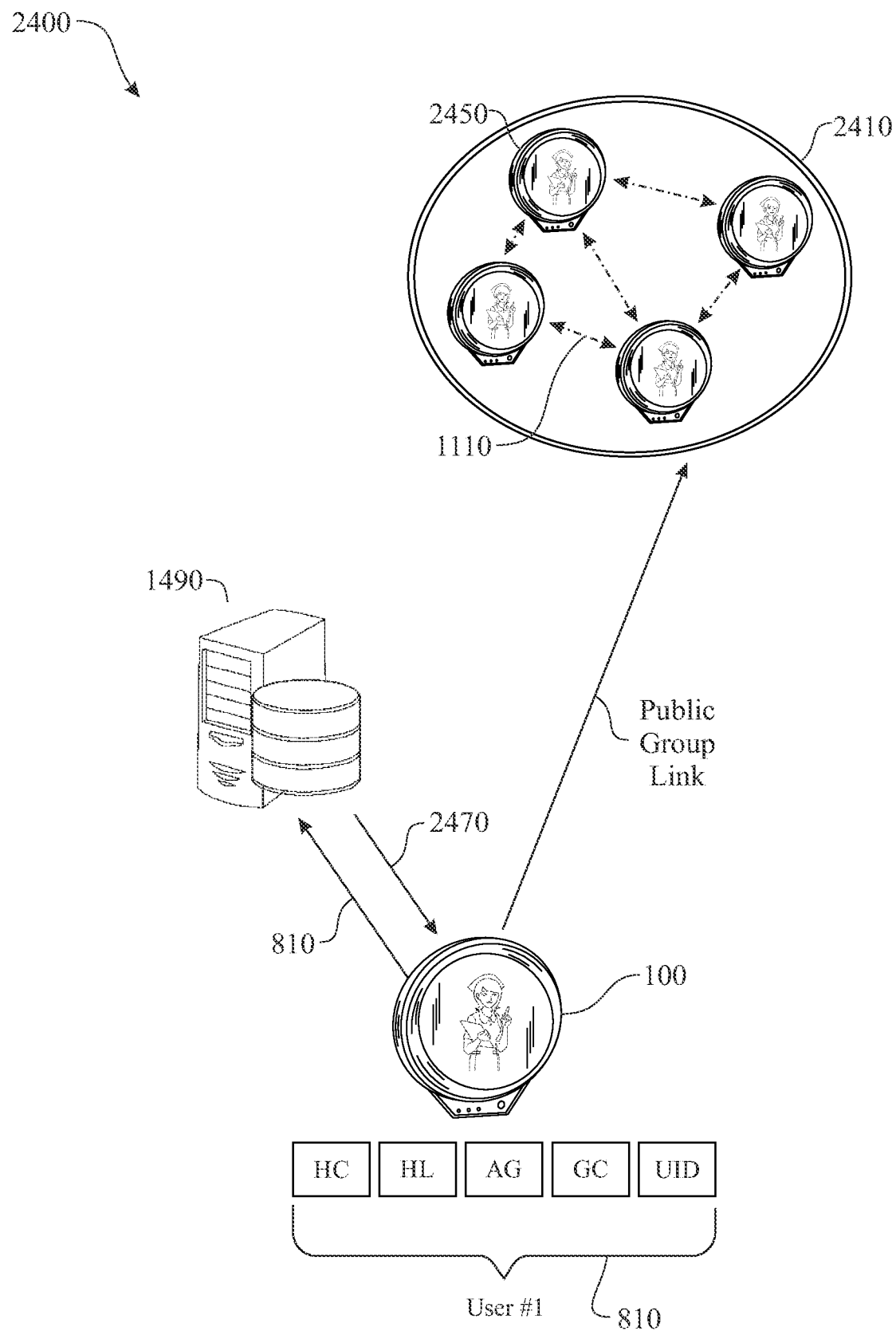
FIG. 24 presents an exemplary schematic diagram where Public Health Hub (HH) Groups are matched to another Health Hub (HH) using a priority level within the General Data Packets (GDP)

An exemplary schematic diagram 2400 illustrating an association between a group of Health Hubs (HH's) 2450 forming a Public Health Group (PHG) 2410 and an autonomous Health Hub (HH) 100 is presented in FIG. 24. The Public Health Group (PHG) 2410 and an autonomous Health Hub (HH) 100 are linked using a priority level within the General Data Packets (GDP's). The exemplary schematic diagram 2400 presents a condition where the General Data Packet 810 of the autonomous Health Hub (HH) 100 is remotely communicated to the Central Health Hub (CHH) 1490. The Central Health Hub (CHH) 1490 analyzes the information contained within the received General Data Packet (GDP) and provides communication link information 2470 for the Public Health Group (PHG) 2410 with the matching health priority levels. The autonomous Health Hub (HH) 100 then utilizes the link 2470 to the Public Health Group (PHG) 2410 to establish communication and interactions with at least one Health Hub 2450 within the Public Health Group (PHG) 2410.

Figure 25:
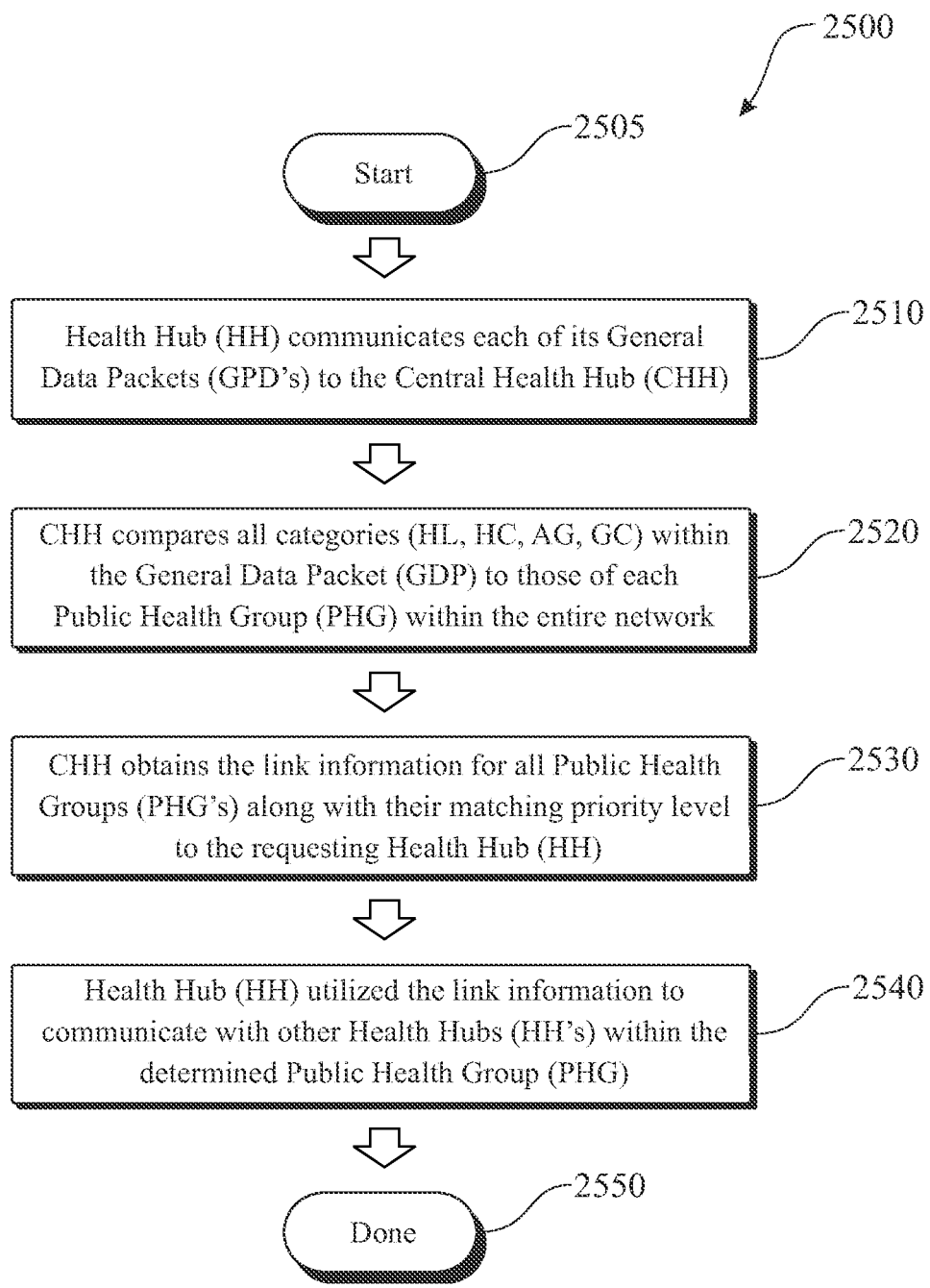
FIG. 25 presents an exemplary flow diagram using the priority level within General Data Packets (GDP) to match Public Health Hub (HH) Groups to another Health Hub (HH)

An exemplary flow diagram 2500, presented in FIG. 25, illustrates how each autonomous Health Hub (HH) 100 communicates the associated General Data Packets (GDP's) 810 to the Central Health Hub (CHH) 1490. The Central Health Hub (CHH) 1490 then compares all categories (HL, HC, AG, GC) within the General Data Packet (GDP) 810 to like categories of each Public Health Group (PHG) within the entire network (step 2520). The Central Health Hub (CHH) 1490 then obtains the link information for all Public Health Groups (PHG's) along with their matching priority level to the requesting Health Hub (step 2530). Finally, the Health Hub (HH) utilizes the link information to communicate with other Health Hubs (HH's) within the determined Public Health Group (PHG) (step 2540). Upon completion, the process terminates (step 2550).

Figure 26:
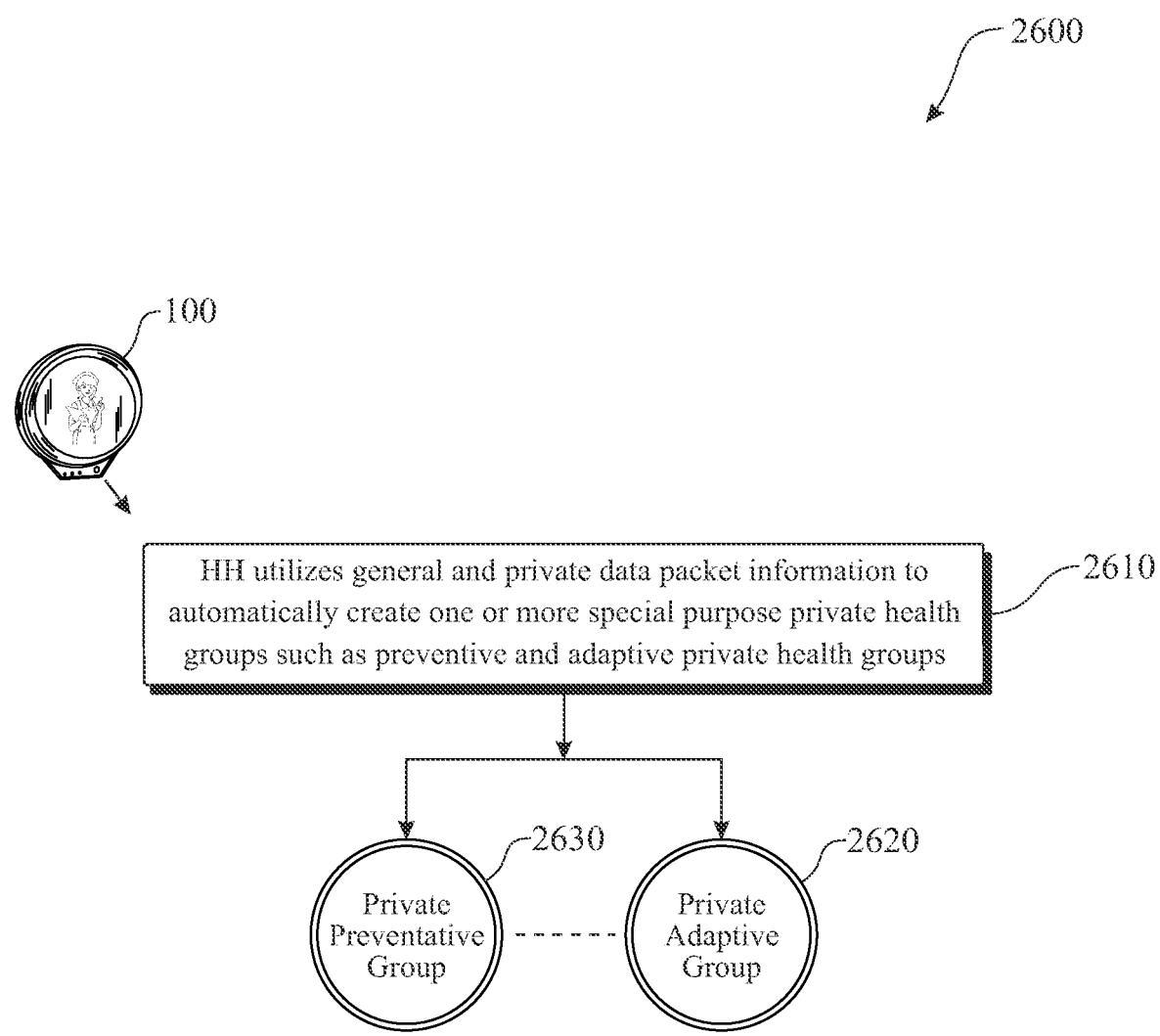
FIG. 26 presents an exemplary flow diagram for forming special purpose private health groups.

An exemplary process 2600 for forming a special purpose private group is presented in FIG. 26. The autonomous Health Hub (HH) 100 utilizes the information in the General Data Packet 810 associated therewith and its Detail Data Packet (DDP) 1110 to automatically create one or more special purpose private health groups (step 2610). Two such exemplary private health groups are a private adaptive health group 2620 and a private preventive health group 2630.

Figure 27:
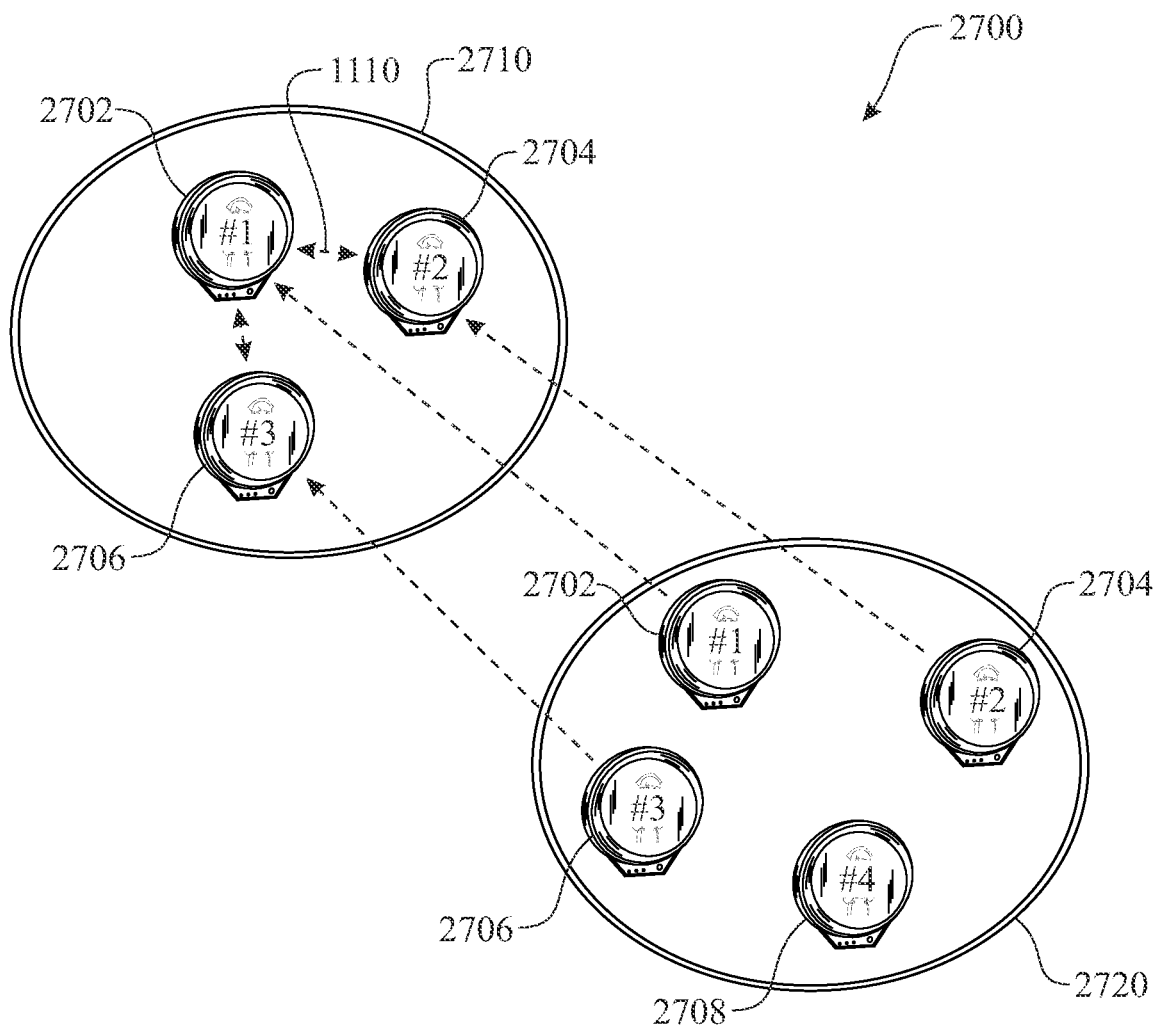
FIG. 27 presents an exemplary schematic diagram illustrating a formation of an adherence/adaptive private health group.

An exemplary process 2700 (shown in a schematic diagram) for forming an adherence private health group is presented in FIG. 27. As the result of having matching General Data Packet (GDP) 810 information, all Health Hubs (HH's) within a Public Health Group (PHG) get assigned to the same exact health priority level by the Central Health Hub (CHH) 1490. Health Hub (HH) #1 2702, Health Hub (HH) #2 2704, Health Hub (HH) #3 2706, and Health Hub (HH) #4 2708 are included in Public Health Group 2720. Health Hub (HH) #1 2702, Health Hub (HH) #2 2704 and Hub (HH) #3 2706 communicate with each other and form a new private health group 2710. In the example shown, all Health Hubs (HH's) 2702, 2704 and 2706 within the private health group 2710 share General Data Packets (GDP's) 810 having similar information, including but not limited to, their Health Code (HC) 720, their Health Level (HL) 730, their Age Group (AG) 740, their Gender Code (GC) 750, and so on. Health Hubs (HH's) 2720, 2704 and 2706 can interactively communicate with each other and coordinate medication scheduling, treatment status, and symptoms with their peers.

Figure 28:
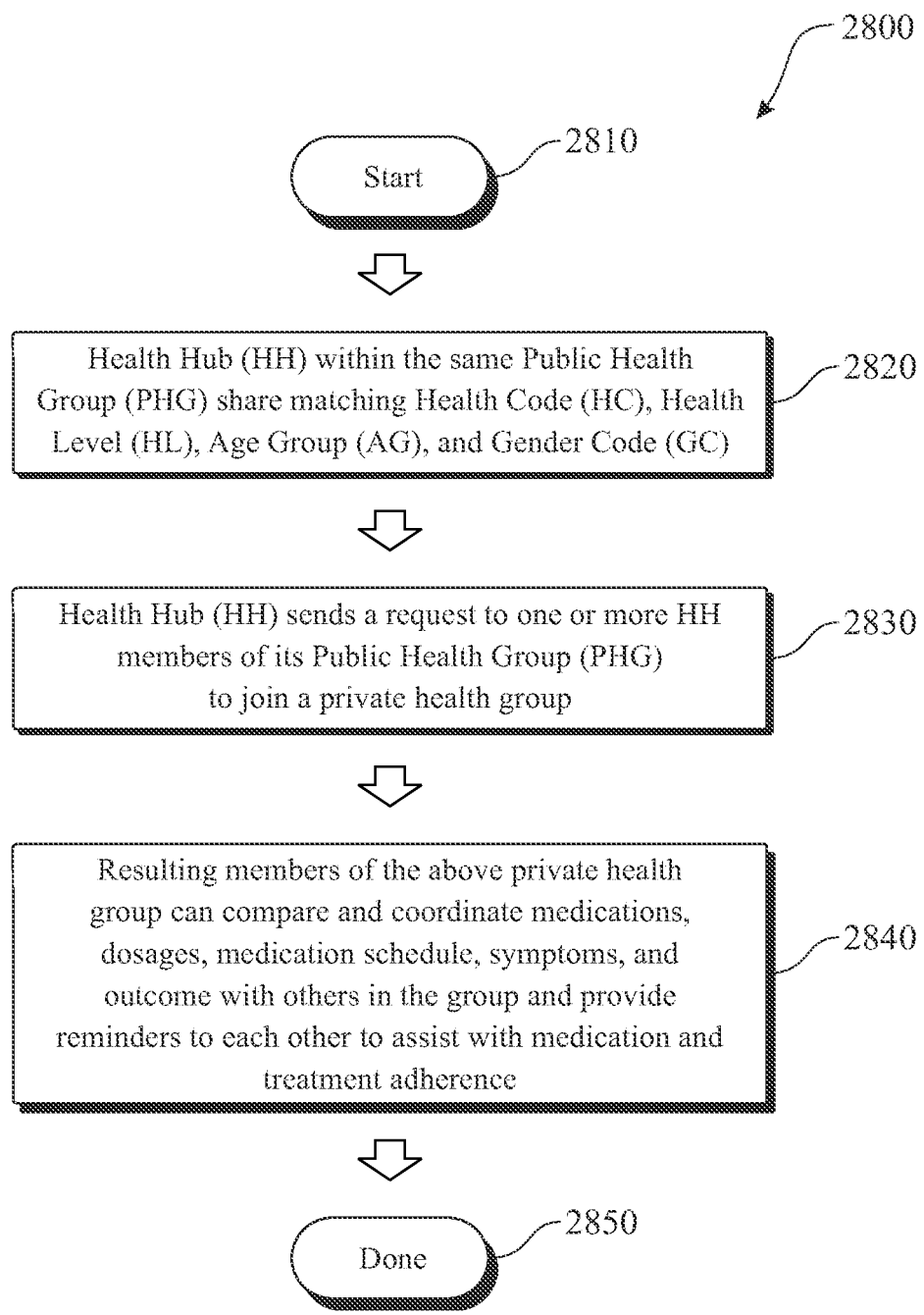
FIG. 28 presents an exemplary flow diagram detailing a process for the formation and function of an adherence private health group.

An exemplary flow diagram 2800 for a formation and function of an adherence private health group is presented in FIG. 28. The Health Hub (HH) within the same Public Health Group (PHG) share a matching Health Code (HC) 720, a matching Health Level (HL) 730, a matching Age Group (AG) 740, and a matching Gender Code (GC) 750 (block 2820). The Health Hub (HH) then sends a request to one or more Health Hub (HH) members of the associated Public Health Group (PHG) to join a Private Health Group (step 2830). Finally, the resulting members of the private health group formed in step 2830 can coordinate medications, dosages, medication schedule, symptoms and outcome with other Health Hubs (HH's) in the group and provide reminders to each other to assist with medication and treatment adherence (step 2840). Upon completion, the process terminates (step 2850).

Figure 29:
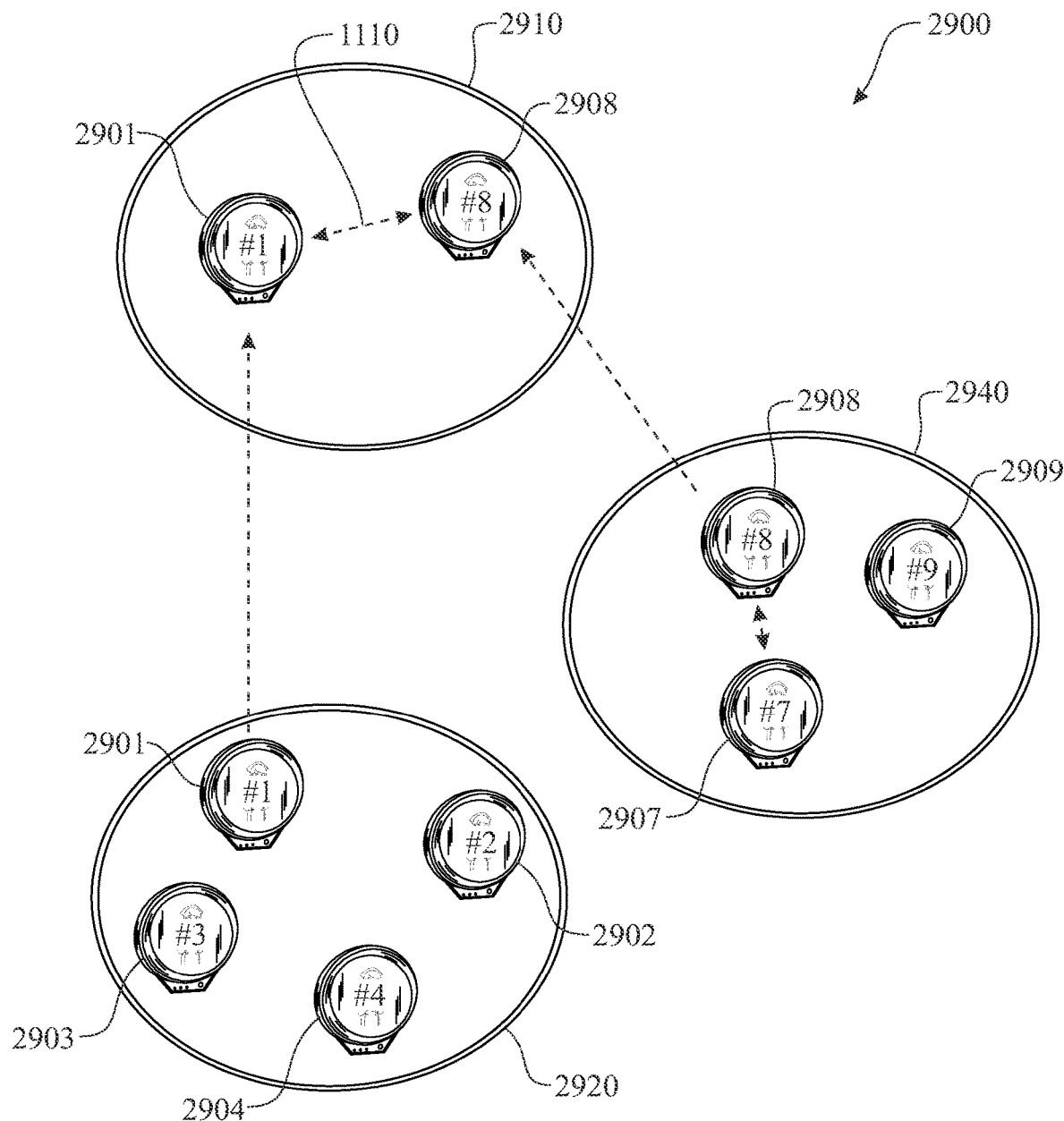
FIG. 29 presents an exemplary schematic diagram illustrating a formation of a preventative/predictive private health group.

An exemplary schematic 2900 illustrating a formation of a preventive/predictive private health group is presented in FIG. 29. As the result of having matching information associated with the General Data Packets (GDP's) 810, Health Hub #1 2901, Health Hub #2 2902, Health Hub #3 2903 and Health Hub #4 2904 are included in a first Public Health Group (PHG) 2920 get assigned to the exact same health priority level by the Central Health Hub (CHH) 1490 in FIG. 14. More specifically, the information associated with each of the General Data Packets (GDP's) 810 of each of the Health Hubs 2901, 2902, 2903, 2904 match one another, the established information includes: the Health Code (HC) 720, the Health Level (HL) 730, the Age Group (AG) 740, the Gender Code (GC) 750, and so on. Similarly, as the result of having matching information associated with each of the General Data Packets (GDP's) 810 associated with Health Hub #7 2907, Health Hub #8 2908, and Health Hub #9 2909 are included in a second Public Health Group 2240 and get assigned to the exact same Health Priority Level (HPL) 1310 by the Central Health Hub (CHH) 1490 in FIG. 14. It is noted that the General Data Packets (GDP's) 810 associated with Health Hub #7 2907, Health Hub #8 2908, and Health Hub #9 2909 share a similar Health Code (HC) 720, a similar Health Level (HL) 730, a similar Age Group (AG) 40, a similar Gender Code (GC) 750, and so on. Furthermore, as shown in the example presented in FIG. 29, the second Public Health Group (PHG) 2940 is assigned a higher Health Level (HL) 730 than the first Public Health Group (PHG) 2920. The exemplary schematic 2900 presents a condition where Health Hub #1 2901 in the first Public Health Group 2920 communicates with Health Hub #8 2908 in the second Public Health Group (PHG) 2940, forming a new private health group 2910. Health Hub #8 2908 belongs to the second Public Health Group (PHG) 2940, which has been assigned a higher priority, and therefore Health Hub #8 2908 maintains a higher Health Priority Level (HPL) 1310 than Health Hub #1 2901. Health Hub #1 2901 can access historical results, diagnosis, progress and lack of, and so on of Health Hub #8 2908 in the newly formed private health group 2910, to better forecast the upcoming progress of Health Hub #1 2901 and take preventive actions to avoid the short comings of Health Hub #8 2908.

Figure 30:
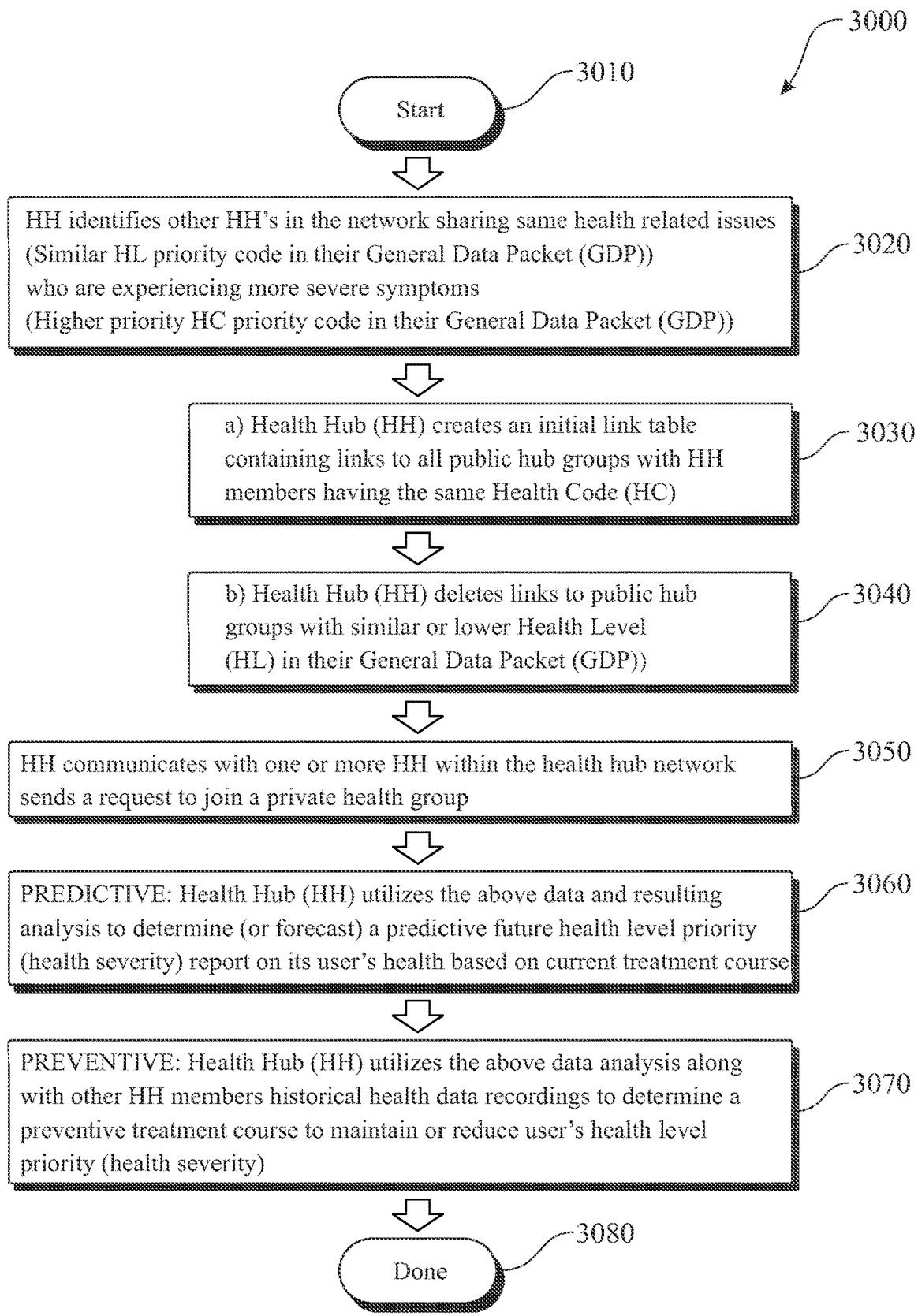
FIG. 30 presents an exemplary flow diagram detailing a process for the formation and function of a preventative/predictive group of Health Hubs (HH's) utilizing a Health Code (HC)

An exemplary flow diagram 3000 detailing steps associated with utilizing the health hub network to provide predictive and/or preventative processes, the exemplary flow diagram 3000 being presented in FIG. 30. The Health Hub (HH) 100 identifies other Health Hubs (HH's) in the Health Hub network sharing the same health related issues (similar Health Level (HL) priority codes in their General Data Packet (GDP)) who are experiencing more severe symptoms (Higher priority Health Code (HC) priority code in their General Data Packet (GDP)) (step 3020). The Health Hub (HH) creates an initial link table containing links to all Public Hub Groups (PHG's) with Health Hub (HH) members having the same Health Code (HC) (step 3030). Otherwise, the Health Hub (HH) deletes links to Public Health Groups (PHG's) with a similar or lower Health Level (HL) in their General Data Packet (GDP) (step 3040). The Health Hub (HH) then communicates with one or more other Health Hubs (HH's) within the health hub network, then sends a request to join a private health group (step 3050). In accordance with a predictive process, the Health Hub (HH) utilizes the above data and resulting analysis to determine (or forecast) a predictive future health level priority (health severity) report on its user's health based upon a current course of treatment (step 3060). In accordance with a preventive process, the Health Hub (HH) utilizes the above data analysis along with other Health Hub HH members historical health data recordings to determine a preventive treatment course to maintain or reduce user's health level priority (health severity) (step 3070). Upon completion, the process terminates (step 3080).

Figure 31:
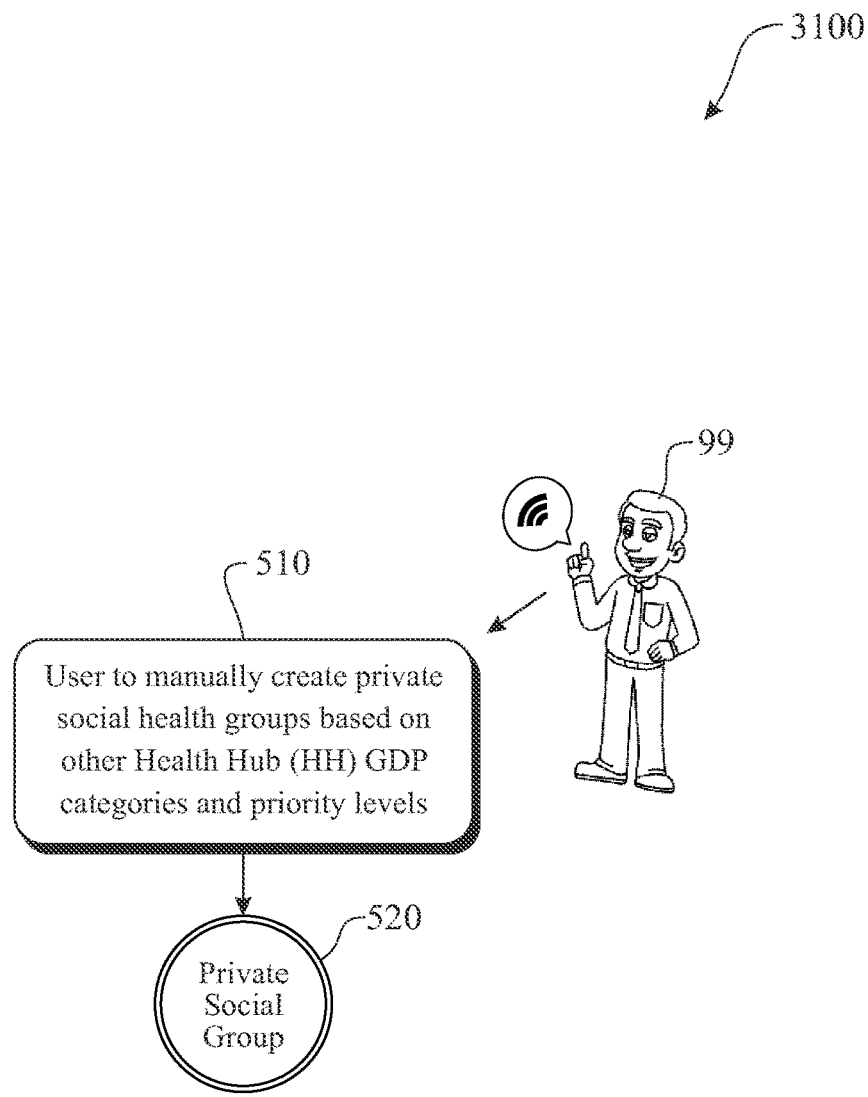
FIG. 31 presents an exemplary flow diagram detailing a process for a creation of a health hub user social health group.

A schematic flow diagram 3100 presenting a process of forming a special user social health group is presented in FIG. 31. The user 99 of the autonomous Health Hub (HH) views the information available within other Health Hub's General Data Package (GDP) 810 and selectively forms one or more user private health groups based on a user's desired category, including any of: Health Code (HC) 720, Health Level (HL) 730, Age Group (AG) 740, Gender Code (GC) 750, and other available categories. The user 99 can manually create a private social health group 520 based upon categories of General Data Packets (GDP's) of other Health Hubs (HH's) 100 (step 510).

Figure 32:
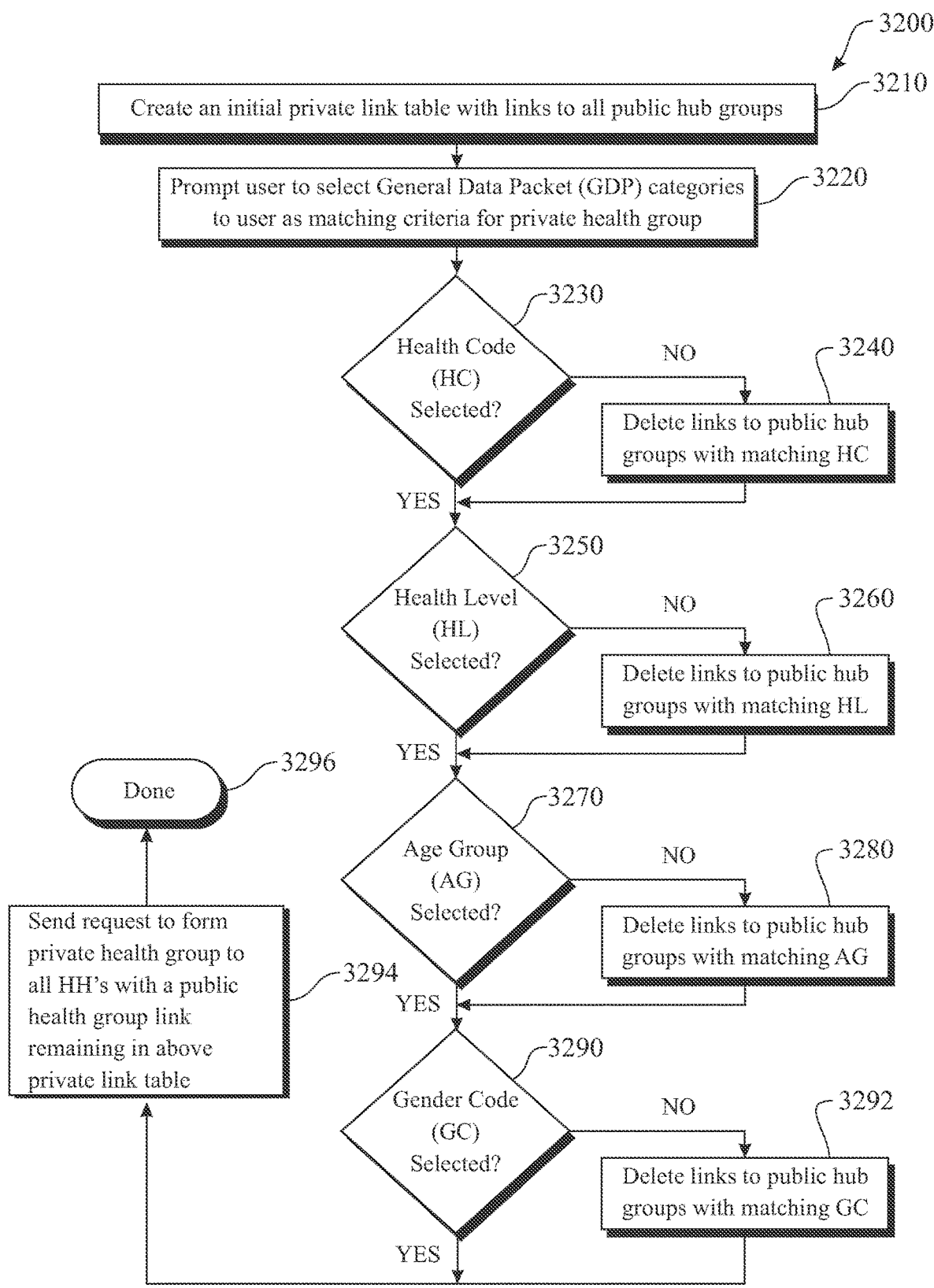
FIG. 32 presents an exemplary flow diagram detailing a process for a manual formation of a private social health group.

An exemplary flow diagram 3200 describing steps of forming a private health group is presented in FIG. 32. An initial private link table with links to all public hub groups is created (step 3210). The user is then prompted to select one or more categories associated with the General Data Packet (GDP) as matching criteria for establishing the private health group (step 3220). Decision step 3230 determines if the Health Code (HC) is selected. In a condition where the Health Code (HC) is selected, the process proceeds with a decision step 3250 pertaining to a Health Level (HL) selection. In a condition where the Health Code (HC) is not selected, the process deletes the links to public hub groups with a matching Health Code (HC) (step 3240). Decision step 3250 determines if the Health Level (HL) is selected. In a condition where the Health Level (HL) is selected, the process proceeds with a decision step 3270 pertaining to an Age Group (AG) selection. In a condition where the Health Level (HL) is not selected, the process deletes the links to the public hub groups with a matching Health Level (HL) (step 3260). In a condition where the Age Group (AG) is selected, then the process proceeds with a decision step 3290 pertaining to a Gender Code (GC) selection. In a condition where the Health Level (HL) is not selected, the process deletes the links to public hub groups with a matching Gender Code GC (step 3280). Finally, in a condition where the Gender Code (GC) is selected 3290, the process proceeds to step 3294 (detailed below). In a condition where the Gender Code (GC) is not selected, the process deletes the links to the public hub groups with a matching Gender Code (GC) (step 3292). Once the above is completed, the process proceeds by sending a request to form a private health group to all Health Hubs (HH's) with a public health group link remaining in the above private link table (step 3294). Upon completion, the process terminates (step 3296).

What is claimed is:

1. A non-transitory computer readable medium storing computer program instructions, the computer program instructions being executable by a processor, the computer program instructions comprising instructions that direct each of the following steps:

a. collecting health profile data about a plurality of network members by obtaining health profile data about each network member via a member health hub associated with each respective network member and conveying the collected health profile data to at least one of a second member health hub and a central health hub using a communication network between the member health hub and the at least one of the second member health hub and the central health hub, each network member having a plurality of established data entries within a plurality of categories, wherein the plurality of categories is a pre-established list of categories;

b. identifying at least one category of a first network member of the plurality of network members utilizing the processor, wherein the processor is a microprocessor that is integrated into at least one of the associated member health hub and the central health hub and creating and storing in memory a first data packet associated with the first network member based on the data entered for a respective category of the at least one category using the processor, the step being replicated to create and store in memory data packets associated with other network members;

c. comparing the first data packet associated with the first network member to data packets associated with other network members using the processor, and determining and setting a priority level for each of the data packets of other network members in relation to the first data packet associated with the first network member using the processor, the priority level being based upon a severity level of the health issues;

d. identifying a grouping of data packets using the processor, defining a first subset of the data packets of all network members using the processor, wherein the first subset of the data packets includes the first data packet;

e. analyzing the first subset of data packets using the processor, determining and diagnosing current health problems of the members of the first subset using the processor, forecasting future health issues of the members of the first subset using the processor, and creating a course of treatment for current and forecasted health issues using the processor;

f. training an-artificial intelligence using steps b, c, d, and e, the artificial intelligence being executable by the processor;

g. using the artificial intelligence to analyze the first subset of data packets, determine and diagnose the current health problems of the network members of the first subset, forecast future health issues of the network members of the first subset, and create a course of treatment for current and forecasted health issues;

h. establishing an interactive conversation between the network member and the member health hub associated with the respective network member;

i. utilizing artificial intelligence to analyze and understand the interactive conversation between inputs from a user and responses from an artificial intelligence virtual assistant to determine and provide triage to the user, wherein the artificial intelligence virtual assistant, employing the artificial intelligence, employs speech to text, text to speech, and natural language processing to obtain user inputs including current health problems of the member, interprets the user inputs, analyzing the current health problems of the member, and responds to the user inputs by using the training of step f to determining a diagnosis of the current health problems of the member and creating a course of treatment for the current health problems of the member, and j. informing the member of the diagnosis of the current health problems of the member and the course of treatment for the current health problems of the member as determined by the artificial intelligence via the virtual assistant.

2. The computer program instructions as recited in claim 1, further comprising additional computer program instructions that defines a second subset of the data packets of all network members using the processor, wherein the second subset of data packets includes the first data packet and at least one other data packet, the at least one other data packet having the same priority level as the first data packet.

3. The computer program instructions as recited in claim 1, further comprising additional computer program instructions, wherein the additional computer program instructions are executed by the processor and accomplishes each of the following additional steps:
  g. analyzing the at least one subset of data packets,
  h. determining and diagnosing the current health problems of the network members of the at least one subset, and
  i. assisting with medication and treatment adherence of current health issues of the members of the said subset.

4. A system that diagnoses and prescribes treatment of network members within a network, the system comprising:
  a first health hub networked to the other health hubs via a wireless communication protocol, wherein the first health hub is located locally or remotely from the other health hubs,
  each of the networked health hubs comprising computer program instructions directing a processor to accomplish steps of:
  a. interacting with a first network member associated with the first health hub;
  b. collecting health profile data describing a state of health of the first network member at the associated first member health hub;
  c. identifying at least one health category of associated with the state of health of the first network member and creating a first data packet based on data entered for the at least one category, wherein the at least one category is selected from a pre-defined group of categories;
  d. creating other data packets associated with all other network members, wherein the other data packets are similar to the first data packet associated with the first network member;
  e. comparing the first data packet associated with the first network member to the other data packets associated with the other network members, and determining and setting a priority level for each of the other data packets in relation to the first data packet, the priority level being based upon a severity level of the health issues;
  f. identifying a grouping of data packets, defining a first subset of the data packets of all network members that includes the first data packet;
  g. utilizing artificial intelligence to analyze and understand an interactive conversation between inputs from a user and responses from an artificial intelligence virtual assistant to determine and provide triage to the user, wherein the artificial intelligence virtual assistant employs speech to text, text to speech, and natural language processing to obtain user inputs, interpret the user inputs, and respond to the user inputs;
  h. using the artificial intelligence to: analyze the first subset of data packets, determine and diagnose the current health problems of the network members of the first subset, forecast future health issues of the network members of the first subset, and create a course of treatment for current and forecasted health issues; and
  i. reporting the course of treatment as determined by the artificial intelligence to the first network member.

5. The system as recited in claim 4, further comprising additional computer program instructions, wherein the additional computer program instructions are executed by the processor and accomplishes a step of the member health hub interacting with the associated network member, wherein interaction provided by the member health hub is accomplished by the processor.

6. The system as recited in claim 5, wherein the speech to text converts user provided spoken words into a text format, the text to speech converts an artificial intelligence generated text responses to an audible, speech response, and the natural language processing provides an analysis and understanding of the user conversation.

7. The system as recited in claim 4, further comprising additional computer program instructions, wherein the additional computer program instructions are executed by the processor and accomplishes a step of utilizing an artificial intelligence virtual assistant animated character to interact with network members, wherein the artificial intelligence virtual assistant animated character is generated by the processor.

8. The system as recited in claim 4, further comprising additional computer program instructions, wherein the additional computer program instructions are executed by the processor and accomplishes a step of accessing and utilizing other available wireless medical devices associated with the network member to collect additional health data regarding the respective network member.

9. The system as recited in claim 4, further comprising additional computer program instructions, wherein the additional computer program instructions are executed by the processor and accomplishes a step of accessing and utilizing other available wireless devices associated with the network member to collect additional health data regarding the respective network member.

10. The system as recited in claim 4, further comprising additional computer program instructions, wherein the additional computer program instructions are executed by the processor and accomplishes a step of utilizing a medical device outside the member health hub of the respective network member to collect detail health data pertaining to the network member associated with the health hub.

11. The system as recited in claim 4, further comprising additional computer program instructions, wherein the additional computer program instructions are executed by the processor and accomplishes steps of:
  defining a second subset of the data packets of all network members, wherein the second subset includes network members having a lower priority compared to the priority of the first network member;
  analyzing the health data of the second subset of the data packets of all network members;
  determining preventative treatment methods for the first network member based upon the analysis of the health data of the second subset of the data packets of all network members; and
  reporting the preventative treatment methods to the first network member.

12. The system as recited in claim 4, further comprising additional computer program instructions, wherein the additional computer program instructions are executed by the processor and accomplishes a step of allowing and facilitating network members to at least one of:
  a) communicate with another network member using the health hub network to communicate between the member health hub and other member health hubs accordingly, and
  b) create a group comprising other network members and communicate the group of other network members by using the health hub network to communicate between the member health hub and other member health hubs accordingly.

13. The system as recited in claim 4, further comprising additional computer program instructions, wherein the additional computer program instructions are executed by the processor and accomplishes steps of:
communicating autonomously between the health hub of the first network member with at least one of the health hubs of other network members using the health hub network to communicate between the first member health hub and other member health hubs accordingly;
forming a grouping of a plurality of network members having at least one common health condition and having a common priority level; and
assisting with adherence of at least one network member of the plurality of network members in taking medications.

14. A health hub apparatus designed and configured to provide interaction with a user to triage, collect health data, form data packets related to a health of a user, determine a severity of a state of health of the user, autonomously communicate with other health hubs within a network, and share the collected information with the other health hubs within the network, analyze the shared information and determine treatment for the user, the apparatus comprising:
  a. a processor;
  b. a memory in signal communication with the processor;
  c. an interface display in signal communication with the processor;
  d. a microphone in signal communication with the processor;
  e. a speaker in signal communication with the processor;
  f. a speech to text and text to speech processing module, the processing module further having a communicator to communicate with a user, the speech to text and text to speech processing module is one of: (a) accomplished by the processor or (b) in signal communication with the processor;
  g. an artificial intelligence module, the intelligence module presenting an animated character to interact with the user, the artificial intelligence module is one of: (a) accomplished by the processor or (b) in signal communication with the processor;
  h. a natural language processing module, the module further having an analyzer for analyzing the user communicated information, the natural language processing module is one of: (a) accomplished by the processor or (b) in signal communication with the processor;
  i. at least one stored health data packets, the data packet containing at least one user health category and at least one severity level of the user's health, each of the at least one stored health data packets being stored in the memory;
  j. a wireless transceiver, the transceiver further having a communication hub, the communication hub being arranged to (a) communicate with other health hubs within a network and (b) share collected health information; and
  k. a health level priority assigner configured to assign a health priority level to the data packet of the user and to data packets of the other health hubs within the network, wherein the health level priority assigner is accomplished by the processor,
  l. a first group creator, wherein the first group creator autonomously forms at least one health group from the other health hubs within the network based on the assigned health priority level, wherein the first group creator is accomplished by the processor,
  m. utilizing artificial intelligence of the artificial intelligence module to analyze and understand an interactive conversation between inputs from a user and responses from an artificial intelligence virtual assistant, employing the artificial intelligence to determine triage for the user and provide triage to the user, wherein the artificial intelligence virtual assistant employs the speech to text module, the text to speech module, and the natural language processing module to obtain user inputs, the artificial intelligence interprets the user inputs, and the artificial intelligence virtual assistant responds to the user inputs, and
  n. a treatment module, the treatment module including a health diagnostics module, a treatment plan module, a preventative treatment module, and a reporting module to report the health diagnosis, the treatment plan, and the preventative treatment plan, wherein the treatment module is accomplished by the processor.

15. The health hub as recited in claim 14, wherein the health hub associated with the user collects health and vital information associated with the user via one or more wireless medical devices.

16. The health hub as recited in claim 14 further comprising a biometric scanning device to securely identify the presence of the user associated with the health hub.

17. The health hub as recited in claim 14, wherein the wireless transceiver of the health hub is configured to pair with one or more mobile devices when the one or more mobile devices are within a close proximity of the health hub.

18. The health hub as recited in claim 14, further comprising a treatment monitor function accomplished by the processor, wherein the treatment monitor function forms an adherence health group, wherein the adherence health group includes the previously identified health groups of network members having the same health issues and the same health severity, wherein the treatment monitor function enables health hubs of the adherence health group to assist one another in adherence with medications and treatments.

19. The health hub as recited in claim 14, further comprising a health forecaster function accomplished by the processor, wherein the health forecaster function identifies health groups including network members having the same health issues but differ in age category, to form forecast health groups for network member health hubs to help forecast the impact of medication usage and treatments in younger users as the younger users age.

20. The health hub as recited in claim 14, further comprising a health priority module, wherein the health priority module is accomplished by the processor, wherein the health priority module determines health priority levels by assigning a unique numeric value to each category of the health data packet, wherein more severe health categories assigned a higher numeric value than the less severe health categories.

21. The health hub as recited in claim 14, wherein the artificial intelligence module includes a function to collect and triage the health information of a user.

\* \* \* \* \*